US012649942B2

US012649942B2

(12) United States Patent (10) Patent No.: US 12,649,942 B2
Ruvkun et al. (45) Date of Patent: Jun. 9, 2026

(54) CAROTENOIDS FOR TREATING OR PREVENTING NAUSEA

(71) Applicant: The General Hospital Corporation, Boston, MA (US)

(72) Inventors: Gary B. Ruvkun, Malden, MA (US); Jothi Amaranath Govindan, Malden, MA (US); Elamparithi Jayamani, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 107 days.

(21) Appl. No.: 17/228,110

(22) Filed: Apr. 12, 2021

(65) Prior Publication Data

US 2021/0230660 A1 Jul. 29, 2021

Related U.S. Application Data

(63) Continuation of application No. 16/409,546, filed on May 10, 2019, now Pat. No. 11,001,870.

(60) Provisional application No. 62/802,398, filed on Feb. 7, 2019.

(51) Int. Cl.
| | |
|---|---|
| *C12P 23/00* | (2006.01) |
| *A61K 31/047* | (2006.01) |
| *A61K 35/66* | (2015.01) |
| *C12N 15/01* | (2006.01) |
| *C12N 15/52* | (2006.01) |

(52) U.S. Cl.
CPC ............ *C12P 23/00* (2013.01); *A61K 31/047* (2013.01); *A61K 35/66* (2013.01); *C12N 15/01* (2013.01); *C12N 15/52* (2013.01)

(58) Field of Classification Search
None
See application file for complete search history.

(56) References Cited

U.S. PATENT DOCUMENTS

| | | | |
|---|---|---|---|
| 6,197,329 | B1 | 3/2001 | Hermelin et al. |
| 7,592,013 | B2 | 9/2009 | Hans et al. |
| 8,637,263 | B1 | 1/2014 | Helton et al. |
| 9,017,662 | B2 | 4/2015 | Rottiers et al. |
| 2004/0091958 | A1 | 5/2004 | Van Ooijen et al. |
| 2005/0260699 | A1 | 11/2005 | Desouza et al. |
| 2009/0175911 | A1 | 7/2009 | Cutting et al. |
| 2009/0197321 | A1 | 8/2009 | Chiou et al. |
| 2009/0263514 | A1 | 10/2009 | Gopinathan |
| 2014/0170700 | A1 | 6/2014 | Umeno et al. |

(Continued)

FOREIGN PATENT DOCUMENTS

| | | |
|---|---|---|
| CN | 106455661 A | 2/2017 |
| JP | 2003504025 A | 2/2003 |
| JP | 2009501547 A | 1/2009 |

(Continued)

OTHER PUBLICATIONS

Heider et al., Appl. Microbiol. Biotechnol. 98: 1223-1235 (2014).*

(Continued)

*Primary Examiner* — Erin M. Bowers
(74) *Attorney, Agent, or Firm* — Nixon Peabody LLP; David S. Resnick; Mark J. FitzGerald

(57) ABSTRACT

Methods and compositions comprising carotenoids for the treatment or prevention of nausea, e.g., chemotherapy-induced nausea and vomiting.

8 Claims, 54 Drawing Sheets

Specification includes a Sequence Listing.

(56) References Cited

U.S. PATENT DOCUMENTS

| | | | | |
|---|---|---|---|---|
| 2015/0196613 | A1 | 7/2015 | Ahmad et al. | |
| 2018/0296582 | A1 | 10/2018 | Von Maltzahn et al. | |

FOREIGN PATENT DOCUMENTS

| | | | | |
|---|---|---|---|---|
| JP | | 2009506095 | A | 2/2009 |
| JP | | 2009159929 | A | 7/2009 |
| JP | | 2017518046 | A | 7/2017 |
| WO | | 2002041833 | A2 | 5/2002 |
| WO | WO 2007/011845 | | * | 1/2007 |
| WO | | 2009134791 | A2 | 11/2009 |
| WO | | 2011125619 | A1 | 10/2011 |
| WO | | 2015177166 | A1 | 11/2015 |
| WO | | 2016/102342 | A1 | 6/2016 |
| WO | | 2017/035526 | A1 | 3/2017 |
| WO | | 2017/187183 | A1 | 11/2017 |
| WO | | 2018169297 | A1 | 9/2018 |
| WO | | 2020162959 | A1 | 8/2020 |

OTHER PUBLICATIONS

Abt et al. "Complete genome sequence of Cellulomonas flavigena type strain (134 T)." Standards in Genomic Sciences 3(1): 15-25 (2010).

Arpin et al. "Bacterial carotenoids, XLVI. C50-Carotenoids, 14. C50-Carotenoids from Arthrobacter glacialis." Acta Chemica Scandinavica. Series B: Organic Chemistry and Biochemistry 29(9): 921-926 (1975).

Autio et al. "Role of AMACR (α-methylacyl-CoA racemase) and MFE-1 (peroxisomal multifunctional enzyme-1) in bile acid synthesis in mice." Biochemical Journal 461(1): 125-135 (2014).

Berdy. "Bioactive microbial metabolites." The Journal of Antibiotics 58(1): 1-26 (2005).

Bolz et al. "A conserved PMK-1/p38 MAPK is required in Caenorhabditis elegans tissue-specific immune response to Yersinia pestis infection." Journal of Biological Chemistry 285(14): 10832-10840 (2010).

Calfon et al. "IRE1 couples endoplasmic reticulum load to secretory capacity by processing the XBP-1 mRNA." Nature 415(6867): 92-96 (2002).

Christian et al. "Vitamin A or β-carotene supplementation reduces symptoms of illness in pregnant and lactating Nepali women." The Journal of Nutrition 130(11): 2675-2682 (2000).

Christopherson et al. "The genome sequences of Cellulomonas fimi and "Cellvibrio gilvus" reveal the cellulolytic strategies of two facultative anaerobes, transfer of "Cellvibrio gilvus" to the genus Cellulomonas, and proposal of Cellulomonas gilvus sp. nov." PloS One 8(1): 1-10 (2013).

Dunbar et al. "C. elegans detects pathogen-induced translational inhibition to activate immune signaling." Cell Host & Microbe 11(4): 375-386 (2012).

Edge et al. "The carotenoids as anti-oxidants—a review." Journal of Photochemistry and Photobiology B: Biology 41 (3): 189-200 (1997).

Felix et al. "The natural history of Caenorhabditis elegans." Current Biology 20(22): R965-R969 (2010).

Fernandes et al. "Carotenoids: A Brief Overview on Its Structure, Biosynthesis, Synthesis, and Applications." Progress in Carotenoid Research: Chapter 1, 16 pages (2018).

Fijan. "Microorganisms with claimed probiotic properties: an overview of recent literature." International Journal of Environmental Research and Public Health 11(5): 4745-4767 (2014).

Fukuoka et al. "Production of dihydroxy C50-carotenoid by Aureobacterium sp. FERM P-18698." Bioscience, Biotechnology, and Biochemistry 68(12): 2646-2648 (2004).

Furubayashi et al. "A highly selective biosynthetic pathway to non-natural C 50 carotenoids assembled from moderately selective enzymes." Nature Communications 6(1): 7534 pp. 1-10 (2015).

Giuffrida et al. "Characterisation of the C50 carotenoids produced by strains of the cheese-ripening bacterium Arthrobacter arilaitensis." International Dairy Journal 55: 10-16 (2016).

Govindan et al. "Lipid signalling couples translational surveillance to systemic detoxification in Caenorhabditis elegans." Nature Cell Biology 17(10): 1294-1303 (2015).

Grant et al. "Intracellular trafficking." WormBook: 1-9 (2006).

Heider et al. "Carotenoid biosynthesis and overproduction in Corynebacterium glutamicum." BMC Microbiology 12 (1): 198 (2012).

Heider et al. "Metabolic engineering for the microbial production of carotenoids and related products with a focus on the rare C50 carotenoids." Applied Microbiology and Biotechnology 98(10): 4355-4368 (2014).

Henke et al. "C50 Carotenoids: Occurrence, Biosynthesis, Glycosylation, and Metabolic Engineering for their Overproduction." Bio-pigmentation and Biotechnological Implementations: Chapter 7, pp. 107-126 (2017).

Henke et al. "Carotenoid production by Corynebacterium: the workhorse of industrial amino acid production as host for production of a broad spectrum of C40 and C50 carotenoids." Intech, Rijeka: 159-173 (2017).

Hornero-Mendez et al. "Involvement of NADPH in the cyclization reaction of carotenoid biosynthesis." Febs Letters 515(1-3): 133-136 (2002).

Hutkins et al. "Prebiotics: why definitions matter." Current Opinion in Biotechnology 37: 1-7 (2016).

Ivanova et al. "Complete genome sequence of Sanguibacter keddieii type strain (ST-74 T)." Standards in Genomic Sciences 1(2): 110-118 (2009).

Kalinowski et al. "The complete Corynebacterium glutamicum ATCC 13032 genome sequence and its impact on the production of L-aspartate-derived amino acids and vitamins." Journal of Biotechnology 104(1-3): 5-25 (2003).

Karrer et al. "Synthesen von Carotinoiden VI. Synthese eines Homologen des β-Carotins mit 15 konjugierten Doppelbindungen: Decapreno-β-carotin." Helvetica Chimica Acta 34(1): 28-33 (1951) [With English Translation].

Klassen. "Phylogenetic and evolutionary patterns in microbial carotenoid biosynthesis are revealed by comparative genomics." PLoS One 5(6): e11257 pp. 1-20 (2010).

Krubasik et al. "Detailed biosynthetic pathway to decaprenoxanthin diglucoside in Corynebacterium glutamicum and Identification of novel intermediates." Archives of Microbiology 176(3): 217-223 (2001).

Krubasik et al. "Expression and functional analysis of a gene cluster involved in the synthesis of decaprenoxanthin reveals the mechanisms for C50 carotenoid formation." European Journal of Biochemistry 268(13): 3702-3708 (2001).

Land et al. "Complete genome sequence of Beutenbergia cavernae type strain (HKI 0122 T)." Standards in Genomic Sciences 1(1): 21-28 (2009).

Lapidus et al. "Complete genome sequence of Brachybacterium faecium type strain (Schefferle 6-10 T)." Standards in Genomic Sciences 1(1): 3-11 (2009).

Li et al. "Genetically engineered biosynthetic pathways for non-natural C 60 carotenoids using C 5-elongases and C 50-cyclases in Escherichia coli." Scientific Reports 9(1): 2982 pp. 1-8 (2019).

Liaaen-Jensen et al., "Bacterial carotenoids XXVII: C50-carotenoids. 3. Structure determination of dehydrogenans-P439," Acta. Chem. Scand. 22: 1171-1186 (1968).

Melo et al. "Inactivation of conserved C. elegans genes engages pathogen-and xenobiotic-associated defenses." Cell 149(2): 452-466 (2012).

Mezzomo et al. "Carotenoids functionality, sources, and processing by supercritical technology: a review." Journal of Chemistry 2016: 3164312 pp. 1-16 (2016).

Milon et al. "Organization of carotenoid-phospholipid bilayer systems. Incorporation of zeaxanthin, astaxanthin, and their C50 homologues into dimyristoylphosphatidylcholine vesicles." Helvetica Chimica Acta 69(1): 12-24 (1986).

(56)          References Cited

OTHER PUBLICATIONS

Monnet et al. "The Arthrobacter arilaitensis Re117 genome sequence reveals its genetic adaptation to the surface of cheese." PloS One 5(11): e15489 pp. 1-14 (2010).

Monteiro-Vitorello et al. "The genome sequence of the gram-positive sugarcane pathogen *Leifsonia xyli* subsp. xyli." Molecular Plant-Microbe Interactions 17(8): 827-836 (2004).

Morohoshi et al. "Genome sequence of Microbacterium testaceum StLB037, an N-acylhomoserine lactone-degrading bacterium isolated from potato leaves." Journal of Bacteriology 193(8): 2072-2073 (2011).

Netzer et al. "Biosynthetic pathway for γ-cyclic sarcinaxanthin in Micrococcus luteus: Heterologous expression and evidence for diverse and multiple catalytic functions of C50 carotenoid cyclases." Journal of Bacteriology 192(21): 5688-5699 (2010).

Nishio et al. "Comparative complete genome sequence analysis of the amino acid replacements responsible for the thermostability of Corynebacterium efficiens." Genome Research 13(7): 1572-1579 (2003).

Niu et al. "Metabolic engineering for the microbial production of isoprenoids: carotenoids and isoprenoid-based biofuels." Synthetic and Systems Biotechnology 2(3): 167-175 (2017).

Norgard et al. "Bacterial carotenoids. 32. C50-carotenoids 6. Carotenoids from Corynebacterium poinsettiae including four new C50-diols." Acta Chemica Scandinavica 24(6): 2183-2197 (1970).

O'Rourke et al. "Genomic clusters, putative pathogen recognition molecules, and antimicrobial genes are induced by infection of C. elegans with M. nematophilum." Genome Research 16(8): 1005-1016 (2006).

PCT International Search Report and Written Opinion in International Appln. No. PCT/US2019/031814, dated Aug. 5, 2019, 14 pages.

Pfander et al. "C45-and C50-carotenoids." Pure and Applied Chemistry 66(10-11): 2369-2374 (1994).

Pilbrow et al. "A novel fatty acid-binding protein-like carotenoid-binding protein from the gonad of the New Zealand sea urchin Evechinus chloroticus." PloS One 9(9): e106465 pp. 1-14 (2014).

Pukall et al. "Complete genome sequence of Jonesia denitrificans type strain (Prevot 55134 T)." Standards in Genomic Sciences 1(3): 262-269 (2009).

Sims et al. "Complete genome sequence of Kytococcus sedentarius type strain (541 T)." Standards in Genomic Sciences 1(1): 12-20 (2009).

Eiyo, Jomyaku Keicho, The Journal of Japanese Society for Parenteral and Enteral Nutrition, vol. 28, No. 2, pp. 627-634 2013 [English Abstract Translation Provided].

Nakaguchi et al. "Preliminary study on conditioning-derived side effects and learned food aversions in cancer chemotherapy," Research reports on hospice/palliative care, Research reports 2011, 2011, pp.

9-20, URL: https://www.hospat.org/assets/templates/hospat/pdf/report_2011/2011-b1.pdf [English Translation Provided].

Sutthiwong et al. "Production of carotenoids by Arthrobacter arilaitensis strains isolated from smear-ripened cheeses." FEMS Microbiology Letters 360(2): 174-181 (2014).

Takarada et al. "Complete genome sequence of the soil actinomycete Kocuria rhizophila." Journal of Bacteriology 190(12): 4139-4146 (2008).

Tao et al. "Genes from a *Dietzia* sp. for synthesis of C40 and C50 β-cyclic carotenoids." Gene 386(1-2): 90-97 (2007).

Tobias et al. "Biosynthesis of novel carotenoid families based on unnatural carbon backbones: a model for diversification of natural product pathways." Biochimica et Biophysica Acta (BBA)— Molecular and Cell Biology of Lipids 1761(2): 235-246 (2006).

Troemel et al. "p38 MAPK regulates expression of immune response genes and contributes to longevity in C. elegans." PLoS Genetics 2(11): 1725-1739 (2006).

Umeno et al. "Evolution of a pathway to novel long-chain carotenoids." Journal of Bacteriology 186(5): 1531-1536 (2004).

Wang et al. "Progress on molecular breeding and metabolic engineering of biosynthesis pathways of C30, C35, C40, C45, C50 carotenoids." Biotechnology Advances 25(3): 211-222 (2007).

Weeks et al. "Structure of the principal carotenoid pigment of Cellulomonas biazotea." Journal of Bacteriology 141(3): 1272-1278 (1980).

Xu et al. "Mutation of the lbp-5 gene alters metabolic output in Caenorhabditis elegans." BMB Reports 47(1): 15-20 (2014).

Yoneda et al. "Compartment-specific perturbation of protein handling activates genes encoding mitochondrial chaperones." Journal of Cell Science 117(18): 4055-4066 (2004).

Taniguchi, et al. "Overexpression of the primary sigma factor gene sigA improved carotenoid production by Corynebacterium glutamicum: application to production of β-carotene and the non-native linear C50 carotenoid bisanhydrobacterioruberin." Metabolic engineering communications 4: 1-11 (2017).

Choi et al. "A study on the anorexia and diet patterns in cancer chemotherapy patients." Journal of Korean Academy of Fundamentals of Nursing 2.1: 19-35 (1995) [English Abstract Provided].

Park et al. "A prospective randomized comparative clinical trial comparing the efficacy between ondansetron and metoclopramide for prevention of nausea and vomiting in patients undergoing fractionated radiotherapy to the abdominal region." Radiation Oncology Journal 19.2: 127-135 (2001) [English Abstract Provided].

Song. "Management of chemotherapy induced nausea and vomiting." The Korean Journal of Medicine 82.5: 532-536 (2012) [English Abstract Provided].

Japanese Pre-Appeal Examination Report in Patent Application No. 2023-090609 with English Translation, dated Dec. 8, 2025, (4 pages).

* cited by examiner

Fluorescence Intensity compared to
*eft-3(q145); pgp-5::gfp* fed on *E. coli* OP50-1

FIG. 1D, continued

Isopentenylpyrophosphate (IPP), C5 crtE ⌐ Dimethylallyl pyrophosphate (DMAPP), C5

Geranyl pyrophosphate (GPP), C10 crtE ⌐ IPP, C5

Farnesylpyrophosphate (FPP), C15 crtE ⌐ IPP, C5

Geranylgeranyl pyrophosphate (GGPP), C20 crtB ⌐ GGPP, C20

Phytoene, C40 crtI

Lycopene, C40 crtEb

Flavuxanthin, C50 crtYe/f

Decaprenoxanthin, C50 eft-3(q145); pgp-5p::gfp

Fed on A. arilaitensis

Fed on E. coli OP50

FIG. 2C

*eft-3(q145); pgp-5p::gfp*

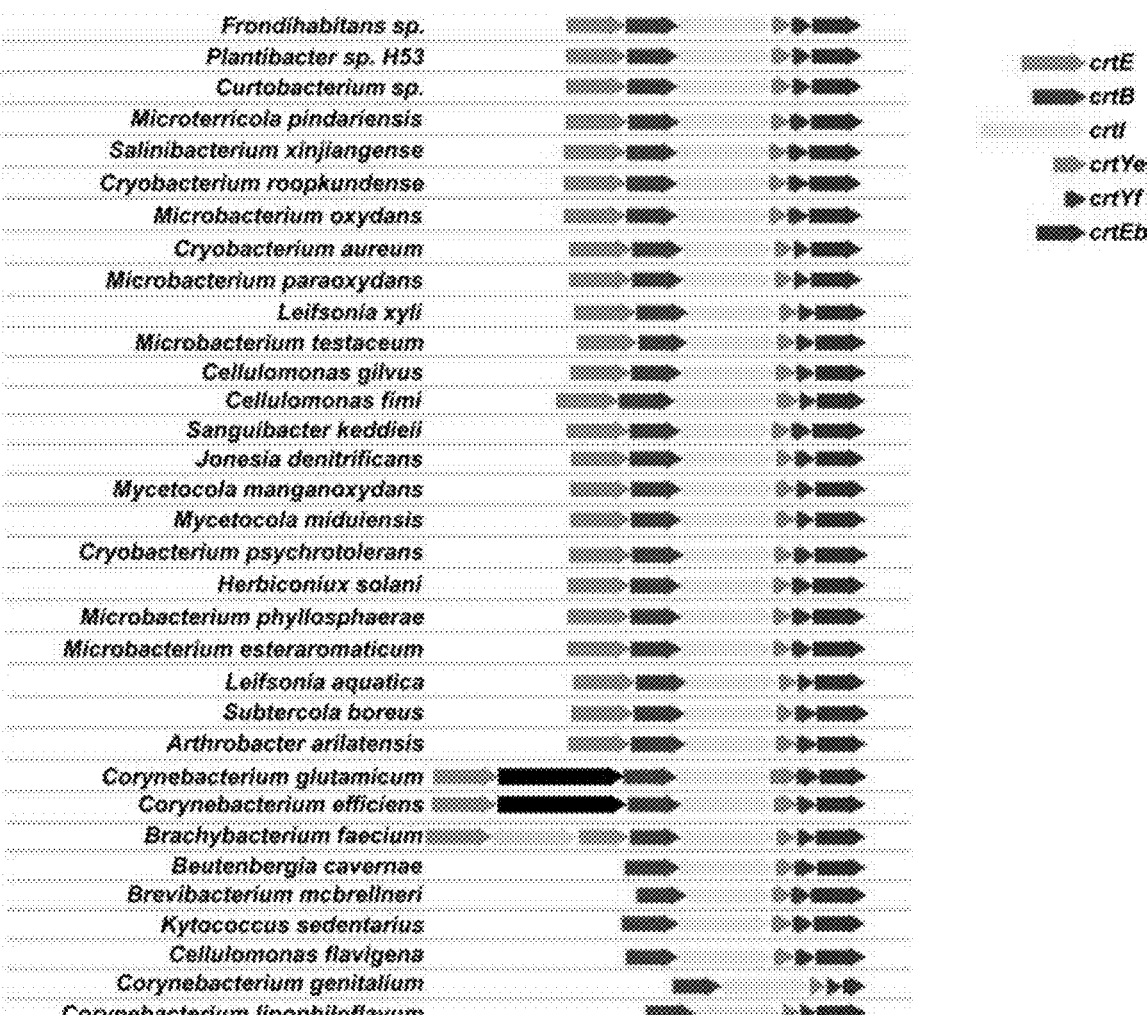
FIG. 7, continued

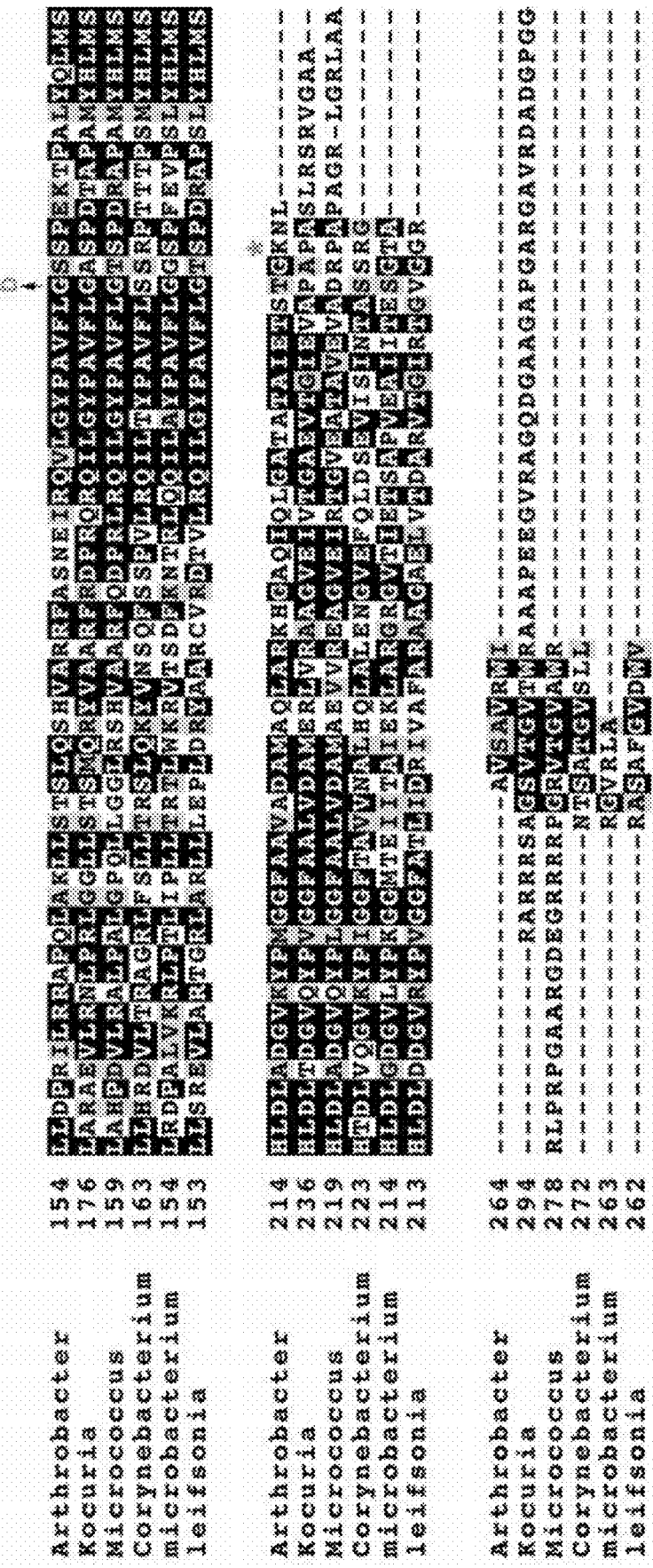
FIG. 8, continued

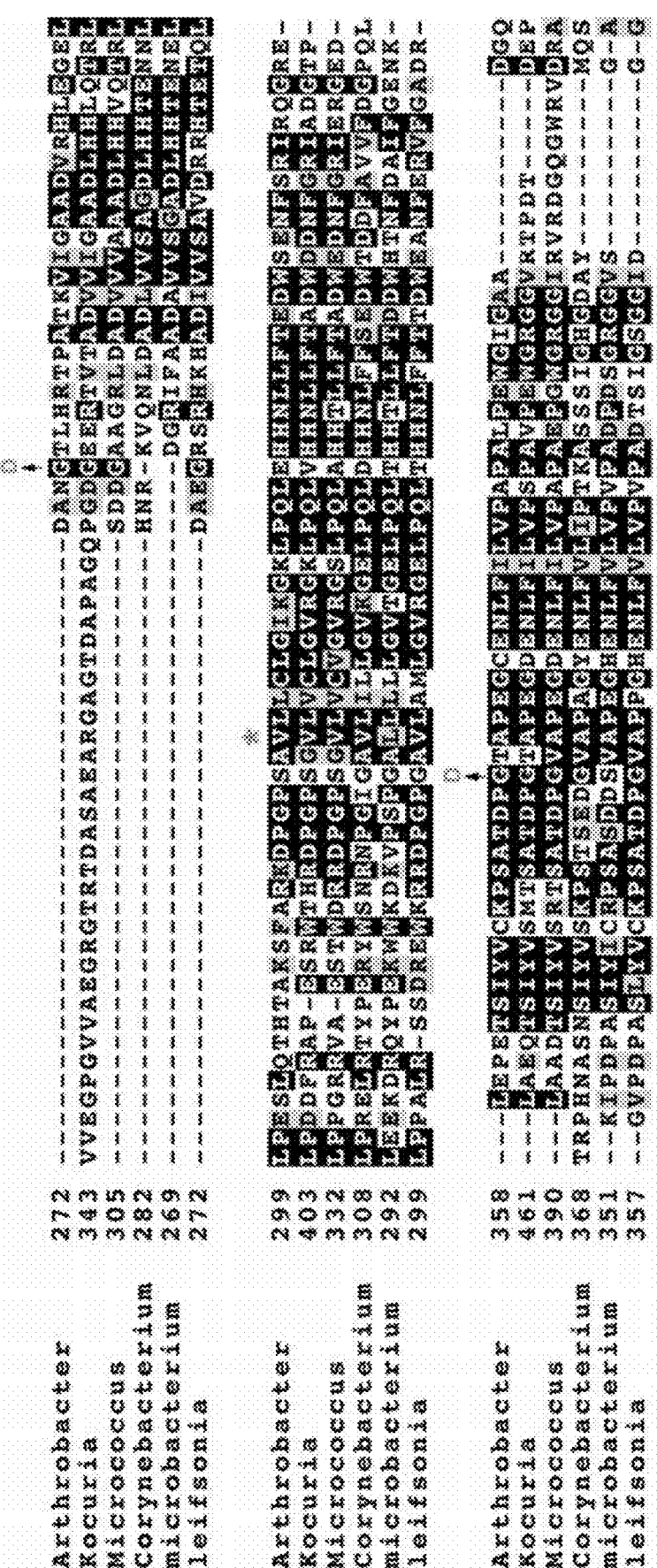
FIG. 8, continued

FIG. 8, continued

CrtB Protein Alignment

*FIG. 9*

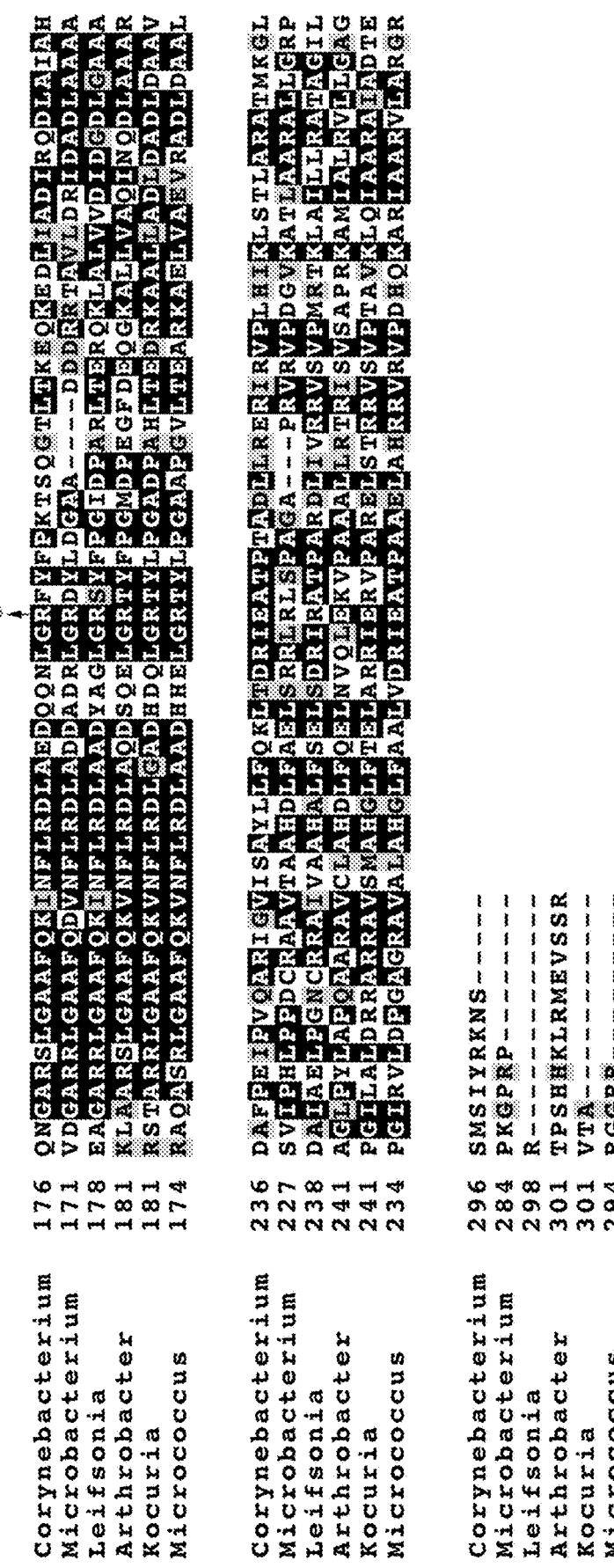
FIG. 9, continued

Grow Kocuria in LB media overnight at 37°C

Centrifuge at 4000 RPM for 15 min

Wash with water

Wash with Acetone

Extract in methanol at 60°C (Multiple rounds)

Filter

Add 2 volumes of 15% NaCl

Mix and add hexane (multiple-rounds)

Remove hexane layer and wash with water at least three times

Evaporate or speed vac to concentrate

*hsp-4p::gfp*

*hsp-6p::gfp*

F35E12.5*p::gfp*

*eft-3(q145); pgp-5p::gfp*

*eft-3(q145); pgp-5p::gfp*

*pgp-5p::gfp*

*pgp-5p::gfp*

FIG. 15B

*pgp-5p::gfp*

*eft-3(q145); pgp-5p::gfp*

CAROTENOIDS FOR TREATING OR PREVENTING NAUSEA

CLAIM OF PRIORITY

This application is a continuation of U.S. application Ser. No. 16/409,546, filed May 10, 2019, which claims the benefit of U.S. Provisional Application Ser. No. 62/802,398, filed on Feb. 7, 2019. The entire contents of the foregoing are incorporated herein by reference.

FEDERALLY SPONSORED RESEARCH OR DEVELOPMENT

This invention was made with Government support under Grant No. AG043184 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Sep. 9, 2019, is named 20190904 29539_0388001_ST25_.txt and is 69,632 bytes in size.

BACKGROUND

Chemotherapy-induced Nausea and Vomiting (CINV) affects 70-80% of patients undergoing chemotherapy and is a leading cause of discontinuation of cancer treatment.

SUMMARY

The present disclosure provides technologies for treatment and/or prevention of certain diseases, disorders, and/or conditions, and furthermore provides technologies for assessing one or more characteristics of agents useful in such treatment and/or prevention.

In some embodiments, provided technologies relate to treatment of nausea and/or vomiting, and in some embodiments relate in particular to induced (e.g., chemotherapy-induced) nausea and/or vomiting. Alternatively, or additionally, in some embodiments, provided technologies relate to treatment or prevention of one or more feeding disorders (e.g., anorexia nervosa).

Nausea and/or vomiting are experienced with a number of diseases and disorders, and furthermore, can result from therapeutic treatments, such as chemotherapy. Regardless of the situation under which nausea and/or vomiting arise, both are generally considered unpleasant and undesirable. Therefore, subjects seek to avoid nausea and/or vomiting; such avoidance can lead, for example, to noncompliance with therapeutic treatments, e.g., when the patient perceives an association between such treatments and experienced nausea and/or vomiting.

The present disclosure appreciates that certain biological pathways involved in surveillance of and/or response to toxins (e.g., toxin detoxification pathways), and particularly certain signaling pathways that transduce detection of translational deficits into induction of detoxification genes are conserved across animal phylogeny may also suppress aberrant human xenobiotic responses; the present disclosure teaches that such agents may have therapeutic potential in the treatment of certain diseases, disorders, or conditions, specifically including, for example, nausea and/or vomiting (e.g., chemotherapy-induced nausea, a major problem in cancer therapy), and/or in feeding disorders such as anorexia nervosa.

The present disclosure thus provides model systems (e.g., *C. elegans*) of characterizing agents for usefulness as therapeutic agents as described herein. Moreover, the present disclosure documents use of such systems to identify and/or characterize certain useful such agents.

Among other things, the present disclosure teaches that certain carotenoid compounds (e.g., certain C50 carotenoid compounds) are useful in the treatment and/or prevention of diseases, disorders and/or conditions such as nausea and/or vomiting (e.g., induced nausea such as chemotherapy-induced nausea) and/or one or more feeding disorders (e.g., anorexia nervosa).

For example, the present disclosure provides that certain carotenoid compounds (e.g., certain C50 carotenoid compounds) inhibit detoxification pathways, including those activated in response to translational deficits induced by toxins and/or by a mutation in a translation component. The present disclosure recognizes that carotenoids are generally well-tolerated by mammals, including humans, and teaches that they are an attractive class of compounds for therapeutic use as described herein (e.g., for the treatment and/or prevention of nausea and/or vomiting, and/or of one or more feeding disorders).

The present disclosure particularly recognizes that certain C50 carotenoid compounds are naturally produced by microbes (as reviewed, for example, by Hencke et al., "C50 Carotenoids: Occurrence, Biosynthesis, Glycosylation, and Metabolic Engineering for their Overproduction", Chapter 5 of *Bio-pigmentation and Biotechnological Implementations*, Ed. Singh, Wiley & Sons, 2017). In some embodiments, delivery of carotenoid compounds (e.g., C50 carotenoid compounds) for therapeutic use as described herein, may be accomplished by administration of a composition that is or comprises a microbe that produces one or more carotenoid compound(s) of interest, or an extract or purified component thereof. In some embodiments, such administration may be of a viable (e.g., microbe), and in certain embodiments may achieve colonization of administered microbe(s) in the recipient (e.g., as part of the recipient's microbiome).

Among other things, the present disclosure appreciates that embodiments involving administration of microbe(s), and particularly of viable (e.g., live) microbe(s) may offer certain advantages, such as, for example, reduced administrations (e.g., reduced frequency of dosing, term of dosing, total number of administered doses, volume and/or concentration of administered doses, and/or combinations thereof, etc), reduced costs, long term efficacy, etc.

Those skilled in the art, reading the present disclosure will appreciate, however, that delivery of carotenoid compounds (e.g., C50 carotenoid compounds) for treatment as described herein is not limited to delivery of microbe(s), or even to extracts and/or components thereof; rather, useful carotenoid compounds (e.g., as described herein) may be prepared in whole or in part by chemical synthesis and/or may be purified from microbial sources (e.g., cultured microbial cells, which may be naturally-occurring and/or genetically or otherwise engineered cells).

Those skilled in the art will further appreciate that any of a variety of delivery routes and/or forms may be utilized to administer compositions that deliver (e.g., that are or comprise microbe(s) and/or extract(s) or component(s) thereof and/or one or more pure carotenoid compound(s) as described herein) useful carotenoid compounds as described herein. In many embodiments, compositions are administered orally (e.g., via a pill, tablet, capsule, powder, lozenge, syrup, elixir, etc). In some embodiments, oral administration is via a nutritional source such as a food or drink.

One challenge associated with development of useful treatments for nausea and/or vomiting has been a lack of an animal model. The present disclosure documents that *Caenorhabditis elegans* can provide an effective model for nausea and/or vomiting. Among other things, the present disclosure provides that *C. elegans* can be useful to characterize (e.g., to screen) agents to assess their impact on and/or usefulness in treating nausea and/or vomiting. For example, microbial toxins and virulence factors often target translation machinery. *C. elegans* responds to translational deficits (e.g., as may result from exposure to toxins and/or from mutation of a translation component) by induction of detoxification and defense response genes. In accordance with the present disclosure, agents that inhibit this induction can be useful in treatment of nausea and/or vomiting, and assessment of such inhibition can be useful to characterizing (e.g., screening) such agents.

Still further, the present disclosure demonstrates that certain carotenoid compounds (e.g., certain C50 carotenoid compounds) can inhibit the *C. elegans* translation deficit surveillance and response pathways (e.g., the *C. elegans* xenobiotic detoxification response to a translational deficit); such carotenoid compounds may be useful in accordance with the present disclosure in therapeutic applications, such as to treat nausea and/or vomiting. For example, the present disclosure specifically documents that a C50 carotenoid compound produced by *Kocuria rhizophila* inhibits *C. elegans* translation deficit surveillance and response pathways. Among other things, the present disclosure describes a genetic analysis, that identifies the biosynthetic pathway for this carotenoid as mediating inhibition of the *C. elegans* translational toxin defense response. Furthermore, the present disclosure documents that *K. rhizophila* extracts (i) recapitulate suppression of the *C. elegans* xenobiotic detoxification response to a translational deficit; and (ii) restore the ability of *K. rhizophila* carotenoid mutants to inhibit such detoxification response to defects in translation.

Additionally, the present disclosure documents that other carotenoid compounds (e.g., C50 carotenoid compounds produced by other bacterial species) also inhibit the *C. elegans* translation deficit surveillance and response pathways (e.g., the *C. elegans* xenobiotic detoxification response to a translational deficit). For example, the present disclosure documents that *C. glutamicum*, which produces the produces the C50 carotenoid decaprenoxanthin, also inhibits *C. elegans* detoxification responses, and furthermore that *C. glutamicum* carotenoid biosynthesis mutants are defective in this inhibition.

Still further, the present disclosure documents that yet another bacterial species *Arthrobacter arilaitensis*, which also produces a C50 carotenoid (specifically, decaprenoxanthin), also inhibits *C. elegans* detoxification responses.

Without wishing to be bound by any particular theory, the present disclosure proposes that carotenoid compounds as described herein (e.g., C50 carotenoid compounds) suppress induction of xenobiotic detoxification by inhibiting a *C. elegans* bile acid signaling pathway that transduces detection of translational deficits into induction of detoxification genes. Suppression of translational surveillance by carotenoid compounds (e.g., C50 carotenoid compounds) as documented herein disables drug detoxification responses so that the potency of translational inhibitory drugs is enhanced. Thus, in some embodiments, carotenoid compounds useful in accordance with the present disclosure may be characterized by their ability to increase potency of translational inhibitory drugs. For example, in some embodiments, a useful carotenoid compound is characterized in that, when such carotenoid compound is contacted with *C. elegans* in the presence of a translational inhibitory drug, one or more features of that translational inhibitory drug's impact on the *C. elegans* is enhanced relative to that observed under otherwise comparable conditions (e.g., presence of the same translational inhibitory drug at the same concentration, etc.) absent the carotenoid compound.

The present disclosure also demonstrates that certain carotenoid compounds (e.g., certain C50 carotenoid compounds) inhibit coupling of translational surveillance to food aversion behaviors in *C. elegans* that are normally induced by translational inhibitory drugs. Thus, in some embodiments, carotenoid compounds useful in accordance with the present disclosure may be characterized by their impact on *C. elegans* food aversion behaviors in the presence of relevant toxins. For example, in some embodiments, a useful carotenoid compound may be characterized in that, when such compound is contacted with *C. elegans* in the presence of a toxin targeting protein translation, one or more features of that toxin's impact on *C. elegans* food avoidance behavior is altered relative to that observed under otherwise comparable conditions (e.g., presence of the same toxin at the same concentration, etc.) absent the carotenoid compound. In some embodiments, agents (e.g., carotenoid compounds such as C50 carotenoid compounds) shown to impact food aversion behavior as described herein may be particularly useful in treatment of one or more food aversion disorders such as, for example, anorexia nervosa.

Thus, provided herein are methods for the treatment of nausea and/or vomiting, or for the reduction of food aversion, in a subject. The methods include administering to a subject in need thereof a therapeutically effective amount of a C50 carotenoid compound. In some embodiments, the subject has or is at risk of developing nausea and/or vomiting associated with chemotherapy or radiation, e.g., chemotherapy-induced nausea and vomiting (CINV) or radiation-induced nausea and vomiting (RINV).

In some embodiments, the subject has or is at risk of developing post-operative nausea and vomiting (PONV).

In some embodiments, the C50 carotenoid compound is selected from the group consisting of decaprenoxanthin, C50-astaxanthin, C50-β-carotene, C50-carotene (n=3) (16, 16-diisopentenylphytoene), C50-zeaxanthin, C50-caloxanthin, C50-nostoxanthin sarcinaxanthin, sarprenoxanthin, acyclic C50 carotenoid bacterioruberin, C50-canthaxanthin, C50-lycopene, C50-phytoene, and combinations thereof. In some embodiments, the C50 carotenoid compound is decaprenoxanthin.

In some embodiments, the step of administering comprises administering a composition that is or comprises (i) a C50-carotenoid-compound-synthesizing microbe or component thereof, (ii) an extract from a C50-carotenoid-compound-synthesizing microbe, (iii) an extracted carotenoid compound, or (iv) a combination thereof. In some embodiments, the C50-carotenoid-compound-synthesizing microbe is viable or alive. In some embodiments, the step of administering comprises administering a sufficient amount of the microbe to colonize the subject's microbiome. In some embodiments, the composition comprises or is prepared from a culture of the microbe. In some embodiments, the microbe is a strain that is found in nature. In some embodiments, the microbe is an engineered microbe. In some embodiments, the engineered microbe comprises a genetic alteration relative to an otherwise comparable reference microbe so that it produces the C50 carotenoid compound at an absolute or relative level different from that of the reference microbe.

In some embodiments, the step of administering comprises administering a composition that comprises or delivers a synthesized C50 carotenoid compound. In some embodiments, the C50-carotenoid-compound-synthesizing microbe is selected from the group consisting of *Kocuria rhizophila, Corynebacterium glutamicum, Arthrobacter arilaitensis*, and combinations thereof.

Also provided herein are therapeutic compositions for oral delivery comprising a therapeutically effective amount of a C50 carotenoid compound, and a pharmaceutically acceptable carrier.

In some embodiments, the composition comprises a microbe that synthesizes the C50 carotenoid compound. In some embodiments, the microbe is a cultured microbe. In some embodiments, the microbe is an engineered microbe. In some embodiments, the engineered microbe comprises a genetic alteration relative to an otherwise comparable reference microbe so that it produces the C50 carotenoid compound at an absolute or relative level different from that of the reference microbe. In some embodiments, the microbe is living or viable. In some embodiments, the microbe has been killed. In some embodiments, the microbe is selected from the group consisting of *Kocuria rhizophila, Corynebacterium glutamicum, Arthrobacter arilaitensis*, and combinations thereof.

In some embodiments, the C50 carotenoid compound is at least 20% w/w of the composition.

In some embodiments, the C50 carotenoid compound is purified.

In some embodiments, the C50 carotenoid compound has a chemical structure found in nature.

In some embodiments, the C50 carotenoid compound is an analog of a reference C50 carotenoid compound found in nature.

In some embodiments, the C50 carotenoid compound is selected from the group consisting of decaprenoxanthin, C50-astaxanthin, C50-β-carotene, C50-carotene (n=3) (16,16-diisopentenylphytoene), C50-zeaxanthin, C50-caloxanthin, C50-nostoxanthin sarcinaxanthin, sarprenoxanthin, acyclic C50 carotenoid bacterioruberin, C50-canthaxanthin, C50-lycopene, C50-phytoene, and combinations thereof. In some embodiments, the C50 carotenoid compound is decaprenoxanthin.

In some embodiments, the therapeutic composition is a liquid, syrup, tablet, troche, gummy, capsule, powder, gel, or film.

Further, provided herein are methods for manufacturing the therapeutic compositions. For example, the method can include the steps of combining a pharmaceutically acceptable carrier with a C50 carotenoid compound; and formulating the combination into the therapeutic composition.

In some embodiments, the step of combining comprises combining the pharmaceutically acceptable carrier with a microbe that synthesizes the C50 carotenoid compound.

In some embodiments, the step of combining comprises combining the pharmaceutically acceptable carrier with a chemically synthesized C50 carotenoid compound.

Also provided herein are methods for the treatment of nausea and/or vomiting, or for the reduction of food aversion, in a subject, comprising a step of administering to a subject in need thereof: (i) a C50-carotenoid-compound-synthesizing microbe or component thereof, (ii) a C50- carotenoid-compound-synthesizing microbe extract, or (iii) an extracted C50-carotenoid compound, or (iv) a combination thereof.

In some embodiments, the subject has or is at risk of developing nausea and/or and vomiting associated with chemotherapy or radiation.

In some embodiments, the subject has or is at risk of developing chemotherapy-induced nausea and vomiting (CINV) or radiation-induced nausea and vomiting (RINV). In some embodiments, the subject has or is at risk of developing post-operative nausea and vomiting (PONV).

In some embodiments, the C50 carotenoid compound-synthesizing microbe is selected from the group consisting of *Kocuria rhizophila, Corynebacterium glutamicum, Arthrobacter arilaitensis*, and combinations thereof.

Additionally, provided herein is the use of a C50 carotenoid compound for treating nausea and/or vomiting, or for reducing food aversion, in a subject in need thereof, and a C50 carotenoid compound for use in treating nausea and/or vomiting or for reducing food aversion in a subject in need thereof.

Also provided is the use of a C50-carotenoid-compound-synthesizing microbe for treating nausea and/or vomiting or for reducing food aversion, and a C50-carotenoid-compound-synthesizing microbe for use in treating nausea and/or vomiting or for reducing food aversion, in a subject in need thereof.

In some embodiments, the C50 carotenoid compound-synthesizing microbe is selected from the group consisting of *Kocuria rhizophila, Corynebacterium glutamicum, Arthrobacter arilaitensis*, and combinations thereof.

Also provided herein are methods for assessing a carotenoid compound for anti-nausea and/or anti-emesis activity. The methods include the steps of (i) contacting a system with the carotenoid compound; and (ii) determining whether the carotenoid compound altered a feature of the system, wherein the feature is associated with nausea and/or vomiting.

In some embodiments, the step of determining comprises comparing the feature before and after performance of the step of contacting.

In some embodiments, the step of determining comprises comparing the feature after the step of contacting with a comparable reference.

In some embodiments, the comparable reference is a historical reference.

In some embodiments, the comparable reference is a negative control reference.

In some embodiments, the comparable reference is a positive control reference.

In some embodiments, the system is or comprises *C. elegans*.

In some embodiments, the feature is a level of food aversion.

In some embodiments, the feature is level or activity of a nucleic acid or protein, or form thereof.

In some embodiments, the feature is or comprises an aspect of a xenobiotic detoxification response.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of embodiments of the invention will be apparent from the following detailed description and figures, and from the claims.

DESCRIPTION OF DRAWINGS

FIGS. 2A-G
A) pgp-5p::gfp induction was significantly reduced in eft-3(q145); pgp-5p::gfp animals fed on *C. glutamicum* wildtype, while mutants in *C. glutamicum* ΔcrtEb, ΔcrtI, ΔcrtY, and ΔcrtB did not suppress GFP induction.
B) A quantification of pgp-5p::gfp expression in eft-3 (q145); pgp-5p::gfp animals fed on *C. glutamicum* wildtype, ΔcrtEb, ΔcrtI, ΔcrtY, and ΔcrtB mutants. Unpaired t-test, ****$P<0.0001$. Mean±s.d is shown. The number of animals analyzed per condition is shown above each bar. ns, was not significant compared to eft-3(q145); pgp-5p::gfp fed on *E. coli* OP50.
C) pgp-5p::gfp induction was significantly reduced in eft-3(q145); pgp-5p::gfp animals fed on *A. arilaitensis* wildtype.
D) A TLC of a *K. rhizophila* extract showing orange pigments.
E) An HPLC of a *K. rhizophila* extract showing absorbance of orange pigments. The inset shows the elution times and absorbance of different peaks from the extract.
F) 750 μg/ml of a *K. rhizophila* extract inhibited pgp-5p::gfp in eft-3(q145); pgp-5p::gfp animals.
G) A quantification of pgp-5p::gfp expression in eft-3 (q145); pgp-5p::gfp animals fed on *K. rhizophila* wildtype, *K. rhizophila* crtEb(e17), *K. rhizophila* crtI(e10), and *K. rhizophila* crtEb(e6) containing either a control extract or an *K. rhizophila* extract.

Figure 1A:
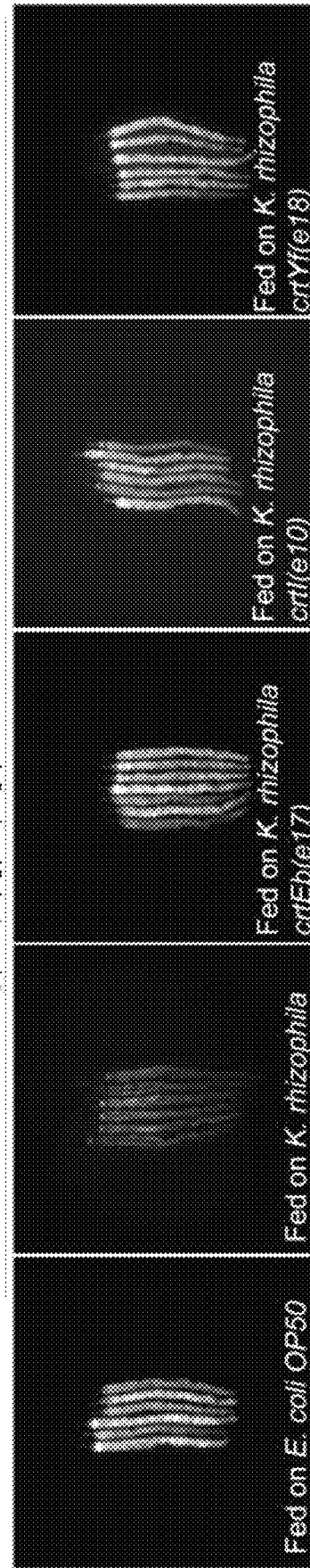
FIGS. 1A-E.
A) pgp-5p::gfp induction was significantly reduced in eft-3(q145); pgp-5p::gfp animals fed on *K. rhizophila* wildtype, while mutants in *K. rhizophila* crtEb(e17), *K. rhizophila* crtI(e10), and *K. rhizophila* crtYe(e2) did not suppress GFP induction.
B) *K. rhizophila* feeding reduced pgp-5p::gfp induction in eft-3(q145); pgp-5p::gfp animals significantly, while in *K. rhizophila* mutants, pgp-5p::gfp expression was not affected. Unpaired t-test, **$P<0.01$. Mean±s.d is shown. The number of animals analyzed per condition is shown above each bar. ns, was not significant compared to eft-3(q145); pgp-5p::gfp fed on *E. coli* OP50.
C) A discoloration phenotype of *K. rhizophila* mutants.
D) A diagrammatic representation of mutations in carotenoid cluster in the *K. rhizophila*.
E) A putative C50 carotenoid biosynthetic pathway in *K. rhizophila*.

C) A discoloration phenotype of observed from *C. gluta-micum* wildtype, ΔcrtEb, ΔcrtI, ΔcrtY, and ΔcrtB mutants.

FIG. 7

An operon structure of bacteria that contain putative gene cluster that might produce decaprenoxanthin.

FIG. 8

An alignment of CrtI protein in different genera. Amino acid conservation across sequences found in different genera is shown.

FIG. 9

An alignment of CrtB protein in different genera. Amino acid conservation across sequences found in different genera is shown.

FIG. 10

An alignment of CrtEb protein in different genera. Amino acid conservation across sequences found in different genera is shown.

FIG. 11

One exemplary biochemical isolation of decaprenoxanthin containing extract from *K. rhizophila.*

FIGS. 12A-B-C

A spectrophotometric analysis of methanolic extracts from *K. rhizophila* wildtype, crtI(e10) and crtb(e6) (12A); wildtype, crtEb(e17) and crtYf(e18) (12B); and wildtype, crtEb(e17) and crtYe(e22) (12C).

FIGS. 13A-E

A) *K. rhizophila* did not induce hsp-4p::gfp.

B) *K. rhizophila* wildtype as well as crtEb(e17) or crtI (e10) mutants did not induce hsp-6p::gfp.

C) *K. rhizophila* wildtype, as well as crtEb(e17), crtI (e10), crtYf(e2) or crtYe(e22) mutants, induced clec-60p::gfp.

D) *K. rhizophila* wildtype, as well as crtEb(e17) or crtI(e10) mutants, did not induce F35E12.5p::gfp.

E) *K. rhizophila* feeding induced suppression of pgp-5p:: gfp in eft-3(q145); pgp-5p::gfp animals was reversible.

FIGS. 14A-D.

A) N-acetyl cysteine, ascorbic acid, trolox or Resveratrol did not suppress pgp-5p::gfp in eft-3(q145); pgp-5p:: gfp animals.

B) beta-carotene or Astaxanthin did not suppress pgp-5p:: gfp in eft-3(q145); pgp-5p::gfp animals.

C) *E. coli* expressing either zeaxanthin, neurosporene, violaxanthin, delta-carotene, or alpha-carotene did not suppress pgp-5p::gfp in eft-3(q145); pgp-5p::gfp animals.

D) pgp-5p::gfp induction in response to 10 μg/ml and 20 μg/ml of hygromycin was significantly reduced in animals fed on *K. rhizophila* wildtype. pgp-5p::gfp induction in response to 50 mg/ml hygromycin in normal in both animals fed on *E. coli* OP50 as well as on *K. rhizophila* wildtype.

FIGS. 15A-E

A) pgp-5p::gfp induction in response to 2.5 μg/ml or 6.25 μg/ml of emetine was significantly reduced in animals fed on *K. rhizophila* wildtype. However, in animals treated with 12.5 μg/ml of emetine, pgp-5p::gfp induction in response was partially reduced in animals fed on *K. rhizophila.* In animals treated with 25 μg/ml of emetine, induction of pgp-5p::gfp was normal both animals treated with either *E. coli* OP50 or *K. rhizophila* wildtype.

B) pgp-5p::gfp induction in response to 6.25 μg/ml of emetine was significantly reduced in animals fed on *K.*

*rhizophila* wildtype, while mutants in *K. rhizophila* crtEb(e17) or *K. rhizophila* crtI(e10) did not suppress the GFP induction.

C) pgp-5p::gfp induction in response to 1 mM of cisplatin was significantly reduced in animals fed on *K. rhizophila* wildtype, while mutants in *K. rhizophila* crtEb (e17), crtYe(e22) or crtI(e10) did not suppress the GFP induction.

D) Carotenoids by themselves were not toxic to the worms in the absence of hygromycin.

E) Animals fed on control extract or *K. rhizophila* extract were sensitive to Antimycin.

FIGS. 16A-C

A) ZK892.4 and C24A3.4 proteins share sequence similarity.

B) Inactivation of ZK892.4 RNAi or C24A3.4 RNAi did not suppress pgp-5p::gfp induction in eft-3(q145); pgp-5p::gfp animals, while double RNAi of ZK892.4 and C24A3.4 suppressed the gfp induction.

C) RNAi of chc-1, fcho-1, or lbp-5 did not induce pgp-5p::gfp.

DEFINITIONS

Administration: As used herein, the term "administration" typically refers to the administration of a composition to a subject or system to achieve delivery of an agent to the subject or system. In some embodiments, the agent is, or is included in, the composition; in some embodiments, the agent is generated through metabolism of the composition or one or more components thereof. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intra-gastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In many embodiments provided by the present disclosure, administration is oral administration. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Carotenoid compound: As used herein, the term "carotenoid compound" refers to compounds that are members of the structurally diverse class of naturally-occurring carotenoid pigments, and structural analogs thereof. In nature, carotenoid compounds are typically synthesized from isoprenoid pathway intermediates. Carotenoids can be acyclic or cyclic, and may or may not contain oxygen, so that the term "carotenoids", in some embodiments, can include both carotenes and xanthophylls. Many carotenoids have strong light absorbing properties. In general, carotenoids are hydrocarbon compounds having a conjugated polyene carbon skeleton formally derived from the five-carbon compound isopentenyl pyrophosphate. In some embodiments, carotenoid compounds may be triterpenes (C30 diapocarotenoids), tetraterpenes (C40 carotenoids), or other compounds that are, for example, C35, C50, C60, C70, C80 in length or other lengths. In some embodiments, a carotenoid may have a length in excess of C200. More than 1000 different carotenoids have been identified in nature. Carotenoids include but are not limited to: antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. For example, carotenoids include oxygenated derivatives. Further, included carotenoid compounds include ester (e.g., glycoside ester, fatty acid ester) and sulfate derivatives (e.g., esterified xanthophylls).

Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, an inventive carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the selected carotenoid is one or more C50 carotenoid compounds.

Carotenoid biosynthesis polypeptide: The term "carotenoid biosynthesis polypeptide" refers to any polypeptide that is involved in the synthesis of one or more carotenoids. To mention but a few, these carotenoid biosynthesis polypeptides include, for example, polypeptides of phytoene synthase, phytoene dehydrogenase (or desaturase), lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, and acyl CoA:diacyglycerol acyltransferase.

Carotenoid-Compound-Synthesizing Microbe: As used herein, the phrase "carotenoid-compound-synthesizing microbe" refers to a microbe (e.g., algae, fungi, bacteria) that synthesizes one or more carotenoid compounds. In some embodiments, a carotenoid-compound-synthesizing microbe may naturally synthesize one or more carotenoids compounds. In some embodiments, a carotenoid-compound-synthesizing microbe includes a carotenogenic modification. In some embodiments, a carotenoid-compound-synthesizing compound may be genetically modified (e.g., to have one or more genetic alterations) so that it synthesizes one or more carotenoids at an absolute or relative level different from that of an otherwise comparable reference microbe that has not been so genetically modified (i.e., does not contain the genetic alteration(s)). For example, in some embodiments, a carotenoid-compound-synthesizing microbe has been genetically engineered to synthesize at least one carotenoid compound not synthesized by the microbe absent the genetic engineering. Alternatively, in some embodiments, a carotenoid-compound-synthesizing microbe may have been genetically engineered so that its synthesis of one or more particular carotenoid compounds may be at a higher level relative to the microbe absent the genetic engineering. In some embodiments, a higher level may be assessed in reference to a threshold level; in some embodiments, a higher level may be assessed in reference to another compound (e.g., another carotenoid compound) also produced by the microbe (prior to the genetic engineering). In some particular embodiments, a carotenoid-compound-synthesizing microbe may have been genetically modified to add or increase expression of one or more genes encoding a carotenoid biosynthesis polypeptide. Alternatively, or additionally, in some embodiments, a carotenoid-compound-synthesizing microbe may have been genetically modified to increase carbon flow through a carotenoid biosynthesis pathway (e.g., by reducing carbon diversion into one or more other biosynthesis or metabolic pathways). In some embodiments, a carotenoid-compound-synthesizing microbe may synthesize one or more carotenoid compounds having a particular number of carbon units. For example, in some embodiments, a carotenoid-compound-synthesizing microbe may synthesize (naturally or as a result of genetic modifications) one or more C50 carotenoid compounds; such a microbe may be referred to as a C50-synthesizing microbe.

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Dosage form: Those skilled in the art will appreciate that the term "dosage form" may be used to refer to a physically discrete unit of an agent (e.g., a therapeutic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population.

Engineered: In general, the term "engineered" refers to the aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: as used herein, refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Improve, increase, inhibit or reduce: As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. In some embodiments, an isolated substance or entity may be enriched; in some embodiments, an isolated substance or entity may be pure. In some embodiments, isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "enriched", "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. Those skilled in the art are aware of a variety of technologies for isolating (e.g., enriching or purifying) substances or agents (e.g., using one or more of fractionation, extraction, precipitation, or other separation).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue, capsules, powders, etc. In some embodiments, an active agent may be or comprise a cell or population of cells (e.g., a culture, for example of a carotenoid-compound-synthesizing microbe); in some embodiments, an active agent may be or comprise an extract or component of a cell or population (e.g., culture) of cells. In some embodiments, an active agent may be or comprise an isolated, purified, or pure compound. In some embodiments, an active agent may have been synthesized in vitro (e.g., via chemical and/or enzymatic synthesis). In some embodiments, an active agent may be or comprise a natural product (whether isolated from its natural source or synthesized in vitro).

Pharmaceutically acceptable: As used herein, the term "pharmaceutically acceptable" which, for example, may be used in reference to a carrier, diluent, or excipient used to formulate a pharmaceutical composition as disclosed herein, means that the carrier, diluent, or excipient is compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be is "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete, for example, when onset of a disease, disorder or condition has been delayed for a predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Risk: as will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Subject: As used herein, the term "subject" refers to an individual to which a provided treatment is administered. In some embodiments, a subject is mammal, e.g., a mammal that experiences or is susceptible to a disease, disorder, or condition as described herein; in some embodiments, a subject is a human or non-human veterinary subject, e.g., an ape, cat dog, monkey, or pig. In some embodiments, a subject is a human. In some embodiments, a patient is suffering from or susceptible to one or more diseases, disorders or conditions as described herein. In some embodiments, a patient displays one or more symptoms of a one or more diseases, disorders or conditions as described herein. In some embodiments, a patient has been diagnosed with one or more diseases, disorders or conditions as described herein. In some embodiments, the disorder or condition is or includes nausea and/or vomiting, and/or one or more food aversion disorders. In some embodiments, a subject is suffering from or susceptible to cancer, or presence of one or more tumors. In some embodiments, the subject is receiving or has received certain therapy to diagnose and/or to treat a disease, disorder, or condition. In some embodiments, a subject has received a therapy (e.g., chemotherapy, radiation, and/or surgery) that induces nausea and/or vomiting.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

The nematode *Caenorhabditis elegans* surveils for deficits in essential cellular activities caused, for example, by microbial toxins, and responds by activating a cellular surveillance-activated detoxification and defenses (cSADD) response (Melo and Ruvkun, 2012). The abundant RNAs and proteins of the ribosome and other proteins that mediate the translation of mRNA to proteins can be targets of microbial toxins and virulence factors. The activity of these translational components is monitored, and decrements in protein synthesis caused by toxins or mutations can be detected. Detection of decrements is coupled via a signal transduction cascade to activate xenobiotic detoxification and behavioral responses, such as food aversion via p38MAPK, bZIP/ZIP-2 transcription factor and bile acid like biosynthetic pathways (Melo and Ruvkun, 2012; Dunbar et al., 2012; Govindan et al., 2015). By monitoring decrements in core cellular functions rather than the molecular structure of an unknown toxin, *C. elegans* can detect unanticipated pathogens and toxins. Many components of this signaling cascade, for example, MAP kinase and bile acid biosynthetic pathway, are conserved across animals; the present disclosure appreciates that a cSADD system of toxin surveillance and response may apply to animals other than *C. elegans*, and furthermore teaches that *C. elegans* may be useful as a model system to characterize agents that modulate this system and may be useful in certain therapeutic applications as described herein.

The present disclosure further appreciates that an animal defensive strategy analogous or homologous to the *C. elegans* cSADD system is likely to drive evolution of bacterial countermeasures to thwart these defense responses; there are many examples of such evolutionary arms races between host and pathogen. The present disclosure also appreciates that commensal bacteria may also seek to silence such animal defense responses to establish a benign or symbiotic relationship.

The present disclosure further appreciates that microbes (e.g., bacteria) synthesize various chemical compounds that have significant biological activities, including compounds that target the ribosome and/or associated translation factors (Berdy et al., 2005); such microbes have proven to be productive sources of drug or candidate drug compounds. The present disclosure (i) teaches useful therapeutic applications of agents that can inhibit certain detoxification pathways; (ii) provides a system for assessing one or more characteristics of agents relative to inhibition of such detoxification pathways; and (iii) identifies potential sources of such agents (e.g., microbes such as bacteria, which in some embodiments may be commensal microbes).

For example, the present disclosure provides that certain bacterial strains (e.g., those that produce certain carotenoid compounds, and in particular certain C50 carotenoid compounds) can be good sources of agents (e.g., certain useful carotenoid compounds) useful in accordance with the present disclosure. Furthermore, the present disclosure provides technologies for assessing one or more relevant characteristics of such agents.

In a microbial suppression screen of diverse bacteria for activities that abrogate activation of xenobiotic detoxification genes in *C. elegans* with a genetically-induced deficit in translation, a potent activity was identified from wild type *K. rhizophila* (Govindan et al., 2015). Genetic analysis of *K. rhizophila* was used to demonstrate that C50 carotenoid compounds can suppress the *C. elegans* translational toxin defense response.

Figure 1B:
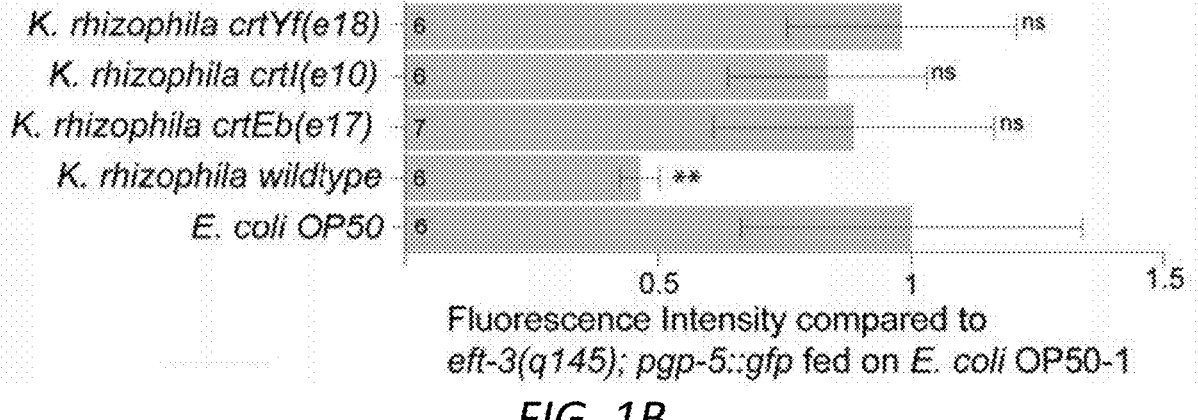
Figure 1C:
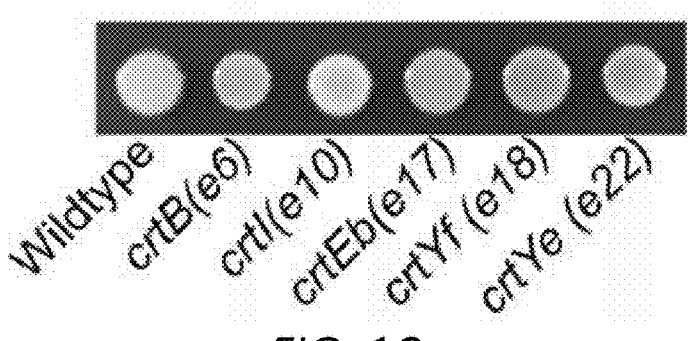

As shown herein, *K. rhizophila*, which produces the C50 carotenoid compound decaprenoxanthin, inhibited the *C. elegans* cSADD translational and DNA damage toxin defense response. Mutants in the *K. rhizophila* C50 carotenoid biosynthetic pathway failed to inhibit this *C. elegans* xenobiotic detoxification response (FIG. 1A-C). Extracts of *K. rhizophila* suppressed this *C. elegans* xenobiotic detoxification response and also restored the ability of *K. rhizophila* carotenoid mutants to achieve such suppression (FIGS. 2B&C). *K. rhizophila* extracts also suppressed induction of *C. elegans* xenobiotic detoxification pathways in response to toxins that target translation (FIG. 3A, FIG. 15C). *K. rhizophila* C50 carotenoid compound(s) also suppressed responses to RNA interference inactivation of other genes, such as a core ribosomal protein or aminocyl tRNA synthetase, that are required for protein synthesis. A C50 carotenoid from *C. glutamicum* also inhibited the induction of *C. elegans* xenobiotic detoxification pathways in response to translation deficit, showing that C50 carotenoid regulation of the *C. elegans* surveillance was not limited to one particular strain of bacteria.

The present disclosure teaches that certain carotenoid compounds (e.g., certain C50 carotenoid compounds) are useful in various therapeutic applications, in particular including treatment of nausea and/or vomiting (specifically including induced nausea and/or vomiting such as chemotherapy-induced nausea and/or vomiting). Carotenoids have been most studied in photosynthetic bacteria and plants in which carotenoids are auxiliary light absorbing components in photosynthesis (Edge et al., 1997). In photosynthetic chlorophyll clusters, carotenoids can absorb and transduce light energy to photosynthetic electron transport systems, which then generate a pH gradient as reduction potential energy of photon-pumped electrons causes physical movements of multiple iron sulfur and heme proteins to move protons across the lipid bilayer. What is common among photosynthetic bacteria is a strong absorbance in the visible light wavelengths and lipid solubility of these pigments. These bacteria are highly colored because carotenoids are highly abundant and have conjugated double bond systems that delocalize electrons to extraordinarily large resonance-stabilized potential wells, with orbital transitions at much lower energy than standard biochemical bonds. Carotenoids are also known antioxidants in photosynthesis. As shown herein, however, the antioxidant activity of carotenoids does not explain the suppression of animal drug detoxification responses because other antioxidants could not suppress *C. elegans* surveillance.

C50 carotenoid compounds may affect animal surveillance of translational components by a simple change in membrane fluidity. As shown herein, C50 carotenoid compounds suppressed induction of the *C. elegans* xenobiotic detoxification response by inhibiting a bile acid biosynthetic pathway. Although bile acids were traditionally thought to be emulsifiers of fat aiding in digestion, several recent studies have found bile acids to be signaling molecules that are important in metabolism as well as immune pathways. Bile acid signaling may be involved in CINV or induction of drug detoxification response in humans. The lipid solubility and abundance of carotenoids may contribute to their anti-bile acid signaling function in *C. elegans* surveillance of translational and DNA damage response.

A cSADD response may not only induce xenobiotic detoxification but also food aversion behaviors. Aversion to food is an appropriate animal response because many toxins originate from bacterial pathogens that can be associated with or cause the rotting of food. Aversion to foods that are associated with the induction of xenobiotic detoxification and bacterial immunity pathways is likely to be an animal program derived from this evolutionary history. The present disclosure provides an insight that the Chemotherapy-induced Nausea and Vomiting (CINV) response in humans may be related to these xenobiotic aversion programs. Interestingly, cisplatin, which is used to block DNA replication in cancer patients, has high emetogenic potential. Emetine, which is an antibiotic that targets eukaryotic protein synthesis, is also highly emetogenic, as the name itself implies. These two drugs were not only able to induce xenobiotic detoxification response in *C. elegans* but also induced a strong food aversion. The pgp-5 ABC transporter gene was strongly induced by toxins that cause DNA damage, and also by the chemically very distinct toxins that inhibit translation (but not by a wide range of toxins that target other pathways such as the mitochondria or ER) (Govindan et al., 2015). Thus, the present disclosure teaches that *C. elegans* food aversion is a good model for studying mechanisms underlying human CINV.

Serotonergic pathways are involved in both *C. elegans* food aversion as well as human CINV (Melo and Ruvkun, 2012). Liver drug detoxification and elimination are a key concern in cancer chemotherapy; amplification of ABC transporters, which eliminate drugs faster, are frequently observed in drug resistant cancer patients. A *K. rhizophila* carotenoid extract caused hypersensitivity to xenobiotics that target protein translation, and also to xenobiotics that cause DNA damage by suppressing induction of drug detoxification pathways. Also, *K. rhizophila* C50 carotenoid compounds suppressed the food aversion induced by emetogenic toxins, emetine or cisplatin.

C50 carotenoid compounds, e.g., decaprenoxanthin, C50-astaxanthin, C50-β-carotene, C50-carotene (n=3) (16,16-diisopentenylphytoene), C50-zeaxanthin, C50-caloxanthin, C50-nostoxanthin sarcinaxanthin, sarprenoxanthin, acyclic C50 carotenoid bacterioruberin, C50-canthaxanthin, C50-lycopene, C50-phytoene, can be used in accordance with the present disclosure as a therapy for treating and/or reducing risk of nausea and/or vomiting, e.g., induced nausea and/or vomiting such as CINV, RINV, etc. Alternatively, or additionally, the present disclosure provides that such C50 carotenoid compounds may be useful as a therapy for treating and/or reducing risk of one or more food aversion disorders (e.g., anorexia nervosa). Still further, the present disclosure provides systems for assessing one or more characteristics of agents relevant to usefulness as a therapy as described herein (i.e., for treating and/or reducing risk of nausea and/or vomiting, and/or one or more food aversion disorders), and also demonstrates that useful such agents include compounds produced by certain microbes (e.g., bacteria), including certain commensal microbes. Using such systems, the present disclosure documents usefulness of certain carotenoid compounds (e.g., C50 carotenoid compounds), including those produced by various bacterial strains (e.g., synthesized by bacterial enzymes). Those skilled in the art, reading the present disclosure, will appreciate that various other compounds (including various other carotenoid compounds) are produced by microbes and/or can be (and/or have been) manufactured by chemical synthesis and assessed for activities such as those embodied in systems exemplified therein. Those of ordinary skill in the art, reading the present disclosure, therefore appreciate that the provides a variety of chemical agents, specifically including carotenoid compounds and exemplified by C50 carotenoids, that are amenable to assessment as described herein and/or are useful as therapeutic agents as described herein.

Methods of Treatment

Methods provided by the present disclosure include methods for the treatment of certain diseases, disorders and conditions. In some embodiments, relevant diseases, disorders and conditions may be or include nausea and/or vomiting, and/or certain food aversion disorders. In some embodiments, nausea and/or vomiting that can be treated as described herein may be associated with one or more of motion sickness, sea sickness, pregnancy (e.g., morning sickness or hyperemesis gravidarum), pain, emotional stress, gallbladder disease, heart attack, concussion or brain injury (e.g., brain tumor), overeating, gallbladder disease, infection, ulcers, gastroparesis, bowel obstruction, appendicitis, infection (e.g., viral infection) etc.

In some embodiments, nausea and/or vomiting that can be treated as described herein may be induced nausea and/or vomiting, e.g., as induced by ingestion or other exposure to toxins (e.g., food poisoning, drug-induced nausea and/or vomiting, drunkenness, etc). In some embodiments, induced nausea and/or vomiting that can be treated as described herein may be nausea and/or vomiting associated with chemotherapy or radiation. In some embodiments, induced nausea and/or vomiting that can be treated as described herein may be CINV or radiation-induced nausea and vomiting (RINV); at least three types of emesis are commonly associated with the use of chemotherapeutic agents, i.e. acute emesis, delayed emesis and anticipatory emesis. In some embodiments, induced nausea and/or vomiting that can be treated as described herein may be or include, e.g., post-operative nausea and vomiting (PONV).

Generally, methods of treatment provided by the present disclosure involve administering a therapeutically effective amount of a carotenoid compound as described herein to a subject who is in need of, or who has been determined to be in need of, such treatment.

In some embodiments, methods of treatment provided herein are prophylactic or preventative, e.g., may be administered to subjects prior to display of significant symptoms and/or to exposure to a particular expected inducement (e.g., to chemotherapy, radiotherapy, surgery, or other treatment (e.g., pharmacological treatment) that is associated with nausea and/or vomiting.

In some embodiments, methods of treatment provided herein are therapeutic, e.g., may be administered to subjects after development of significant symptoms of nausea and/or vomiting (e.g., during or after at least one episode of nausea or vomiting.

In preferred embodiments, provided methods of treatment are administered to a subject that is a mammal, e.g., a mammal that experiences a disease, disorder, or condition as described herein; in some embodiments, a subject is a human or non-human veterinary subject, e.g., an ape, cat dog, monkey, or pig.

In many embodiments, "treatment" involves ameliorating at least one symptom of a disease, disorder, or condition associated with nausea. Often, nausea results in food aversion, loss of appetite and/or reduced caloric intake, and potentially weight loss; in some embodiments, administration of a therapeutically effective amount of a carotenoid compound described herein can result in a reduction in nausea, vomiting, and/or food aversion. Alternatively or additionally, in some embodiments, administration of a therapeutically effective amount of a carotenoid compound as described herein may achieve a restoration of appetite and/or a return or approach to normal caloric intake, a reduction, cessation, or slowing of weight loss, an increase in weight/weight gain, and/or a reduction in the frequency, duration, or severity of present or future episodes of nausea, vomiting, food aversion, and/or loss of appetite.

In some embodiments, the methods can include administration of a therapeutically effective amount of a carotenoid compound before, during (e.g., concurrently with), or after administration of a treatment that is expected to be associated with nausea and/or vomiting, e.g., a subject who is about to undergo chemotherapy, radiotherapy or other treatment that is associated with nausea and vomiting.

In some embodiments, subjects who receive treatment as described herein may be receiving and/or may have received other treatment (e.g., chemotherapeutic, radiotherapeutic, surgical, etc), for example that may induce vomiting or that may be intended to treat one or more symptoms or features of a disease disorder or condition as described herein, so that provide carotenoid therapy is administered in combination with such other therapy to treat the relevant disease, disorder, or condition.

Carotenoid Compositions

Among other things, the present disclosure provides compositions that comprise or otherwise deliver carotenoid compound(s) (e.g., C50 carotenoid compounds) to subjects suffering from or susceptible to one or more diseases, disorders, or conditions as described herein.

Those skilled in the art are aware that more than 750 carotenoid compounds have been previously identified. Carotenoids are generally classified by number of 5-carbon isoprenoid units, resulting in different lengths of their carbon backbone. See, e.g., Henke et al., (2017). *C50 Carotenoids: Occurrence, Biosynthesis, Glycosylation, and Metabolic Engineering for their Overproduction*. In, Bio-pigmentation and Biotechnological Implementations, pp. 107-126. doi: 10.1002/9781119166191.ch5; Fernandes, *Introductory Chapter: Carotenoids—A Brief Overview on Its Structure, Biosynthesis, Synthesis, and Applications*. In Progress in Carotenoid Research. (2018) doi:10.5772/intechopen.79542; Mezzomo et al., (2016) *Carotenoids Functionality, Sources, and Processing by Supercritical Technology: A Review* in *J. Chemistry* Volume 2016:1.

In some embodiments, carotenoid compounds useful in accordance with the present disclosure have a relatively long isoprene backbone, for example having a length within a range of about 45 to about 60 carbon atoms. In some embodiments, useful carotenoid compounds as described herein may have an isoprene backbone that is 50 carbons long, i.e., may be C50 carotenoid compounds, e.g., deca-prenoxanthin, or other C50 carotenoids, e.g., C50-astaxan-thin (also called decaprenoastaxanthin; see Milon et al., Helv. Chim. Acta 69, 12-24 (1986); Furubayashi et al., Nat Commun. 2015; 6: 7534) or C50-β-carotene (also called decapreno-β-carotene) (see, e.g., Karrer et al., Helv. Chim. Acta 34, 28-33 (1951); Furubayashi et al., Nat Commun. 2015; 6: 7534); 16,16'-diisopentenylphytoene (Umeno et al., J Bacteriol, 186, 1531-1536 (2004)); C50-carotene (n=3) (16,16-diisopentenylphytoene), C50-zeaxanthin, C50-caloxanthin, and C50-nostoxanthin (US20140170700); sarcinaxanthin, sarprenoxanthin, acyclic C50 carotenoid bacterioruberin, C50-canthaxanthin, C50-lycopene, C50-phytoene (Li et al., Scientific Reports volume 9, Article number: 2982 (2019)). See also Pfander, Pure and Applied Chemistry, 66(10-11):2369-2374 (1994).

Those skilled in the art are aware of a variety of tech-nologies for producing carotenoid compounds. See, for example, Mezzomo et al., (2016) *Carotenoids Functionality, Sources, and Processing by Supercritical Technology: A Review* in *J. Chemistry* Volume 2016:1. In some embodi-ments, carotenoid compounds may be isolated from an organism (e.g., a plant or microbe) that has produced it. In some such embodiments, such plant or microbe may have been developed and/or cultivated by man. In some embodi-ments, a plant or microbe may be a natural plant or microbe.

In some embodiments, a plant or microbe may be an engineered plant or microbe (e.g., a plant or microbe engi-neered to be a carotenoid-compound-synthesizing plant or microbe as described herein).

Those skilled in the art are aware of various plant and/or microbe sources that have been or can be engineered to be carotenoid-compound-synthesizing plants or microbes as described herein. See, for example, WO2016/102342.

In some embodiments, a carotenoid compound may be isolated from a plant or microbial source (e.g., from a cultivar or culture thereof). Those skilled in the art are aware of a variety of technologies for processing plant and/or microbial cells or tissues, for example, to prepare extracts thereof and/or to isolate components thereof and/or com-pounds therefrom.

Alternatively, or additionally, in some embodiments, a carotenoid compound may be partly or wholly prepared in vitro (e.g., by chemical and/or enzymatic synthesis, or a combination thereof), and may optionally be further isolated and/or purified as is known in the art.

A variety of technologies are known in the art that can be used to prepare extracts of cells or organisms that produce relevant carotenoid compounds, and/or to isolate extracts, components, or compounds therefrom, or to process (e.g., to isolate and/or purify one or more carotenoid compounds from) in vitro carotenoid synthesis systems. To give but a few examples, such technologies may include, for example, one or more of organic extraction, vacuum concentration, chromatography, and so on.

Those skilled in the art are aware that various lower order (shorter carbon chain) carotenoids such as α-carotene, β-carotene, γ-carotene, δ-carotene, ε-carotene, lutein, zeax-anthin, canthaxanthin, fucoxanthin, astaxanthin, antherax-anthin, and violaxanthin are synthesized by modification of the ends of lycopene through cyclization or oxidation. Higher order (more carbon atoms) carotenoids can be pre-pared, e.g., using in vitro methods or in vivo or ex vivo methods (e.g., via natural or genetically modified organ-isms). For example, C50 carotenoids can be synthesized in vitro by the addition of two dimethylallyl pyrophosphate (DMAPP) molecules to C(2) and C(2') of the respective C40 carotenoid, or extracted from an organism (e.g., wild-type or engineered) that synthesizes the C50 carotenoid (e.g., a C50-carotenoid-compound-synthesizing microbe). See, e.g., Milon et al., Helv. Chim. Acta 69, 12-24 (1986); Karrer et al., Helv. Chim. Acta 34, 28-33 (1951); Furubayashi et al., Nat Commun. 2015; 6: 7534; Tobias and Arnold, Biochim Biophys Acta. 2006 February; 1761(2):235-46; Henke et al., (Jun. 14, 2017). *Carotenoid Production by Corynebacte-rium: The Workhorse of Industrial Amino Acid Production as Host for Production of a Broad Spectrum of C40 and C50 Carotenoids, Carotenoids*, Dragan J. Cvetkovic and Goran S. Nikolic, Intech Open, DOI: 10.5772/67631. Available from: intechopen.com/books/carotenoids/carotenoid-pro-duction-by-*Corynebacterium*-the-workhorse-of-industrial-amino-acid-production-as-host-f, Henke et al., (2017). *C50 Carotenoids: Occurrence, Biosynthesis, Glycosylation, and Metabolic Engineering for their Overproduction*. In, Bio-pigmentation and Biotechnological Implementations, pp. 107-126. doi:10.1002/9781119166191.ch5; Fernandes, *Introductory Chapter: Carotenoids—A Brief Overview on Its Structure, Biosynthesis, Synthesis, and Applications*. In Progress in Carotenoid Research. (2018) doi:10.5772/in-techopen.79542; Heider et al., Appl Microbiol Biot 2014; 98(10):4355e68; Wang et al., Biotechnol Adv 2007; 25(3): 211e22; Niu et al., Synthetic and Systems Biotechnology 2 (2017) 167e175; Li et al., Scientific Reports volume 9, Article number: 2982 (2019); US20050260699; US20140170700; US20040091958; US20090197321; and others.

In some embodiments, one or more carotenoid com-pounds for use in accordance with the present disclosure can be provided as purified, or substantially purified, molecules, or as less purified (e.g., enriched) extracts of an organism that produces a carotenoid.

In some embodiments, a preparation that is or comprises one or more carotenoid compounds is incorporated into or otherwise used to generate a pharmaceutical composition as described herein, that, when administered to a subject, delivers a carotenoid compound thereto.

In some embodiments, a carotenoid preparation or caro-tenoid composition (e.g., a pharmaceutical composition that comprises or delivers a carotenoid compound) comprises at least 20%, 30%, 40%, 50%, 60%, 70%, 80%, 90%, 95%, 97%, or 99% w/w carotenoid compounds.

In some embodiments, compositions for use in accor-dance with the present disclosure are pharmaceutical com-positions, e.g., for oral administration. Pharmaceutical com-positions typically include an active agent (e.g., a carotenoid compound, such as a C50 carotenoid compound, or a source thereof), and a pharmaceutically acceptable carrier. Certain exemplary pharmaceutically acceptable carriers include, for instance saline, solvents, dispersion media, coatings, anti-bacterial and antifungal agents, isotonic and absorption delaying agents, and the like, compatible with pharmaceu-tical administration.

In some embodiments, a pharmaceutical composition for use in accordance with the present disclosure may include and/or may be administered in conjunction with, one or more supplementary active compounds; in certain embodi-ments, such supplementary active agents can include ginger, curcumin, probiotics (e,g, probiotic strains of one or more of the following genera: *Lactobacillus, Bizdobacterium, Sac-charomyces, Enterococcus, Streptococcus, Pediococcus, Leuconostoc, Bacillus*, and/or *Escherichia coli* (see Fijan, Int J Environ Res Public Health. 2014 May; 11(5): 4745-4767); prebiotics (nondigestible food ingredients that help support growth of probiotic bacteria, e.g., fructans such as fructooligosaccharides (FOS) and inulins, galactans such as galactooligosaccharides (GOS), dietary fibers such as resistant starch, pectin, beta-glucans, and xylooligosaccharides (Hutkins et al., Curr Opin Biotechnol. 2016 February; 37: 1-7)) and combinations thereof.

Pharmaceutical compositions are typically formulated to be compatible with its intended route of administration. Examples of routes of administration include oral administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). Oral compositions generally include an inert diluent or an edible carrier. To give but a few examples, in some embodiments, an oral formulation may be or comprise a syrup, a liquid, a tablet, a troche, a gummy, a capsule, e.g., gelatin capsules, a powder, a gel, a film, etc.

In some embodiments, pharmaceutically compatible binding agents, and/or adjuvant materials can be included as part of a pharmaceutical composition. In some particular embodiments, a pharmaceutical composition can contain, e.g., any one or more of the following inactive ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In some embodiments, the compositions can be taken as-is or sprinkled onto or mixed into a food or liquid (such as water).

In some embodiments, a carotenoid composition that may be administered to subjects as described herein may be or comprise an ingestible item (e.g., a food or drink) that comprises (e.g., is supplemented with one or more carotenoids. In some embodiments, a useful composition may contain one or more carotenoid compounds at a level higher than that at which the carotenoid compound is found in components thereof, and/or higher than normally present in the relevant foods or beverages, e.g., to provide a level of carotenoids that is sufficient to provide a therapeutic effect as described herein.

In some embodiments, a food can be or comprise one or more of bars, candies, baked goods, cereals, salty snacks, pastas, chocolates, and other solid foods, as well as liquid or semi-solid foods including yogurt, soups and stews, and beverages such as smoothies, shakes, juices, and other carbonated or non-carbonated beverages. In some embodiments, foods are provided with carotenoids already included therein; in some embodiments, foods are prepared by a subject by mixing in carotenoids.

Compositions can be included in a kit, container, pack, or dispenser, together with instructions for administration or for use in a method described herein.

Those skilled in the art, reading the present disclosure, will appreciate that, in some embodiments, a carotenoid composition as described herein may be or comprise one or more cells, tissues, or organisms (e.g., plant or microbe cells, tissues, or organisms) that produce (e.g., have produced, and/or are producing) a relevant compound. In some embodiments, such cells, tissues, or organisms may have previously produced the relevant carotenoid; in some embodiments, such cells, tissues or organism are producing the carotenoid compound(s).

In some embodiments, carotenoid compositions may include cells, tissues, and/or organisms that have been killed (e.g., heat killed). Alternatively, in some embodiments, carotenoid compositions may include cells, tissues, and/or organisms that are viable or alive.

In some embodiments, methods of treatment as described herein involve administering one or more viable or living carotenoid-compound-synthesizing cells, tissues, or organisms. In some such embodiments, the cells, tissues, or organisms are microbial cells and are administered according to a regimen that achieves population of the subject's microbiome with administered cells.

In some embodiments, a carotenoid composition as described herein comprises and/or is formulated through use of one or more cell cultures and/or supernatants or pellets thereof, and/or a powder formed therefrom.

Those skilled in the art will appreciate that, in some embodiments, technologies for preparing carotenoid compositions and/or preparations, and/or for preparing one or more carotenoid compositions (and particularly for preparing pharmaceutical compositions) may include one or more steps of assessing or characterizing a compound, preparation, or composition, e.g., as part of quality control. In some embodiments, if an assayed material does not meet pre-determined specifications for the relevant assessment, it is discarded. In some embodiments, if such assayed material does meet the pre-determined specifications, then it continues to be processed as described herein.

Methods of Identifying and/or Characterizing

Among other things, the present disclosure provides systems that permit assessment of one or more agent characteristics relevant for usefulness as described herein. In some embodiments, technologies for identifying and/or characterizing agents as described herein may involve comparisons with an appropriate reference (e.g., with a positive control references and/or with a negative control reference). In some embodiments, a reference may be or comprise a historical reference; in some embodiments, a reference may be or comprise a contemporaneous reference.

In some embodiments, provided technologies may be useful for screening test agents, e.g., that may be or comprise one or more polypeptides, peptides, inorganic or organic large or small molecules, or compositions that include or deliver them, in order to identify agents useful in methods as described herein. Alternatively, or additionally, in some embodiments, provided technologies may be useful to characterize one or more agents, for example, during development and/or commercialization of such agent, or a pharmaceutically acceptable composition thereof.

As used herein, "small molecule" refers to small organic or inorganic molecules of molecular weight below about 3,000 Daltons. In general, small molecules may have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

Those skilled in the art will appreciate that in some embodiments, and particularly in screening embodiments, provided technologies may be utilized to identify (e.g., to screen) and/or characterize a plurality of agents. In some embodiments, such plurality is or comprises reasonably comparable agents (e.g., one or more particular small molecule compounds and a plurality of analogs thereof); in some embodiments, a plurality of agents is or comprises a plurality of natural products (e.g., carotenoid compounds such as C50 carotenoid compounds) and/or one or more analogs thereof. In some embodiments, a plurality of agents is or comprises a combinatorial library of small molecule compounds. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

In some embodiments, provided technologies may be used to screen and/or assess a plurality of agents that cover a variety of functions such as charge, aromaticity, hydrogen bonding, flexibility, size, length of side chain, hydrophobicity, and rigidity.

In some embodiments, libraries screened as described herein can comprise a variety of types of test compounds. In some embodiments, a given library can comprise a set of structurally related or unrelated test compounds. In some particular embodiments, a library may comprise a set of peptides or peptidomimetic molecules. In some embodiments, a library may comprise carotenoid compounds, e.g., a naturally-occurring or synthetic carotenoid, e.g., a C35, C40, C45, C50, C55, or C60 carotenoid.

In some embodiments, provided technologies are utilized to assess a set of agents related to one another by systematically alteration of the structure of a first agent; in some such examples, the first agent may be or comprise a compound of known activity (e.g., a carotenoid compound such as a C50 carotenoid compound).

In some embodiments, technologies provided herein utilize or generate correlations between structural features and presence or absence (or level) of biological activity of interest—i.e., structure-function relationships. In some instances, structure-function relationships may be defined empirically; in some embodiments, structure-function relationships may be defined through utilization of computer modeling and/or analysis prediction methodologies.

In some embodiments, a food aversion assay as described herein is used. In some embodiments, a test sample is, or is derived from (e.g., a sample taken from) an in vivo model of a disorder as described herein. For example, a test compound is applied to a test sample comprising one or more *C. elegans* organisms, and one or more effects of the test compound is evaluated. For example, the ability of a test compound to counteract food aversion in the presence of a chemotherapeutic agent or other nausea-inducing stimulus can be tested. Alternatively, effects on a reporter gene, e.g., ABC transporter gene fusion pgp-5p::gfp, can be evaluated by detecting alterations in GFP fluorescence. As one of skill in the art will appreciate, other reporters could readily be used.

In some embodiments, a compound can be screened by a method described herein to determine whether it can reduce nausea (e.g., have anti-nausea activity), vomiting (e.g., have anti-emesis activity), and/or food aversion in a system (e.g., an animal model, e.g., *C. elegans*). In some embodiments, a compound that is determined to reduce nausea (e.g., have anti-nausea activity), vomiting (e.g., have anti-emesis activity), and/or food aversion in a system (e.g., an animal model, e.g., *C. elegans*) can be considered a candidate compound. A candidate compound that has been screened e.g., in a system having features associated with nausea, vomiting, and/or food aversion, e.g., an in vivo model of a disease, disorder, or condition associated with nausea and/or vomiting, e.g., *C. elegans*, and determined to have a desirable effect on nausea, vomiting, and/or food aversion can be considered a candidate therapeutic agent. In some embodiments, a candidate therapeutic agent can be tested in a larger animal model or in a clinical setting. Candidate therapeutic agents, once screened in a clinical setting, can be therapeutic agents. Candidate compounds, candidate therapeutic agents, and therapeutic agents can be optionally optimized and/or derivatized, and formulated with physiologically acceptable excipients to form pharmaceutical compositions.

A compound can be assessed by a method described herein to determine whether it can reduce nausea (e.g., have anti-nausea activity), vomiting (e.g., have anti-emesis activity), and/or food aversion in a system (e.g., an animal model, e.g., *C. elegans*). In some embodiments, the present disclosure provides a method for assessing a compound (e.g., a carotenoid) to determine its ability to reduce nausea (e.g., anti-nausea activity), vomiting (e.g., anti-emesis activity), and/or food aversion in a system (e.g., an animal model, e.g., *C. elegans*). In some embodiments, a method of assessing a compound to determine its ability to reduce nausea (e.g., anti-nausea activity), vomiting (e.g., anti-emesis activity), and/or food aversion in a system (e.g., an animal model, e.g., *C. elegans*) is part of an assay (e.g., a release test, a stability test, an efficacy test, etc.) performed for approval or maintenance of approval from a regulatory body (e.g., United States Food and Drug Administration, European Medicines Agency, etc.). In some embodiments, a method of assessing a compound (e.g., a carotenoid) to determine its ability to reduce nausea (e.g., anti-nausea activity), vomiting (e.g., anti-emesis activity), and/or food aversion in a system (e.g., an animal model, e.g., *C. elegans*) is part of a method of manufacture. In some embodiments, an assessment can be performed as part of a method of screening. In some embodiments, a system can be an animal system. In some embodiments, an animal system is a model system, e.g., *C. elegans*, cats, dogs, apes, or pigs.

Assessed compounds determined to reduce nausea (e.g., have anti-nausea activity), vomiting (e.g., have anti-emesis activity), and/or food aversion in a system (e.g., an animal model, e.g., *C. elegans*) can be systematically altered, e.g., using rational design, to optimize binding affinity, avidity, specificity, or another parameter. Such optimization can also be screened and/or assessed using the methods described herein. In some embodiments, a method includes screening a first library of compounds using one or more steps known in the art and/or described herein, e.g., identifying one or more hits in a library, subjecting hits to systematic structural alteration to create a second library of compounds structurally related to a hit, screening a second library using the methods described herein, or a combination thereof. Thus, in one embodiment, a method includes screening a first library of compounds using one or more steps known in the art and/or described herein, e.g., identifying one or more hits in a library, subjecting hits to systematic structural alteration to create a second library of compounds structurally related to a hit, screening a second library using the methods described herein, or a combination thereof.

An assessed compound determined to reduce nausea (e.g., have anti-nausea activity), vomiting (e.g., have anti-emesis activity), and/or food aversion in a system (e.g., an animal model, e.g., *C. elegans*) can be considered a candidate therapeutic compounds useful in reducing nausea, vomiting, and/or food aversion as described herein. A variety of techniques useful for determining the structures of compounds can be used in methods described herein, e.g., NMR, mass spectrometry, gas chromatography equipped with electron capture detectors, fluorescence and absorption spectroscopy. The present disclosure provides the insight that compounds determined to reduce nausea (e.g., have anti-nausea activity), vomiting (e.g., have anti-emesis activity), and/or food aversion in a system (e.g., by the methods described herein) can be used in method of treatment, prevention, or delay of development or progression of a disease, disorder and/or condition described herein. The present disclosure provides the insight that compounds determined to reduce nausea (e.g., have anti-nausea activity), vomiting (e.g., have anti-emesis activity), and/or food aversion in a system (e.g., by the methods described herein) can be used in method of treating nausea, vomiting, and/or a food version described herein.

An assessed compound determined to reduce nausea (e.g., have anti-nausea activity), vomiting (e.g., have anti-emesis activity), and/or food aversion in a system (e.g., *C. elegans*) can be assessed in a second system (e.g., a large animal, e.g., ape, monkey, cat, dog, pig, etc.). An animal can be monitored for a change in due to presence of a compound, e.g., for reduced nausea or food aversion. In some embodiments, a system is a human, e.g., a human with CINV or RINV, and a parameter is reduced severity, frequency, or duration of nausea, vomiting, and/or food aversion.

EXAMPLES

Embodiments provided herein are exemplified in the following examples, which do not limit the scope of the disclosure or claims.

Materials and Methods

The following materials and methods were used in the Examples below.

Strains

N2 Bristol was the wildtype strain used.

The following strains and mutant alleles were used:

SJ4100 [zcIs13[hsp-6::GFP],

WE5172 [ajIs1(pgp-5::gfp)X],

JG16 [eft-3(q145)/hT2[bli-4(e937) let-?(q782) qIs48](I; III); ajIs1(pgp-5::gfp)X], JG20 [ajIs1(pgp-5::gfp); agEX(pvha-6::mcherry::zip-2+ myo-2::gfp)], AY101 [acls101[F35E12.5P::GFP+rol-6(su1006)]

SJ4005 [zcIs4 [hsp-4::GFP] V],

SJ4100 (zcIs13[hsp-6::GFP])

Growth and Handling of Microbes Used:

16S ribosomal sequence was amplified using specific primers and sequenced to identify the microbes. LB media as well as plates was used for culturing *Kocuria rhizophila, Arthrobacter arilaitensis* and *Corynebacterium glutamicum* and its mutants. 500 ml of overnight culture was seeded onto SK media plates and incubated at room temperature for 2 days before initiating the experiments. For experiments involving *Kocuria rhizophila* wildtype and mutants, *Arthro-*

*bacter arilaitensis*, and *Corynebacterium glutamicum* wildtype and as well as mutants, synchronized L1-larval stage animals grown until L4-larval stage or day one of adulthood in *E. coli* OP50 seeded plates and was washed in M9 buffer at least five times before transferring to the appropriate bacterial food.

Drug Treatments:

Hygromycin diluted in M9 solution to the desired concentration was added onto *E. coli* OP50 bacteria containing NGM plates. Stock solution of emetine or cisplatin was diluted in M9 and the desired concentration was added onto *E. coli* OP50 bacteria containing NGM plates. 750 μg/ml of *K. rhizophila* extracts was added onto *E. coli* OP50 bacteria containing NGM plates containing appropriate concentrations of hygromycin or cisplatin or emetine. For the xeno-biotic experiments, synchronized L1-stage animals were dropped onto the drug containing plates and scored 4 days later.

RNAi Assays:

For RNAi assays synchronized L1 larval stage animals of the appropriate genotype were fed with appropriate RNAi clones until they reach day one of adulthood. Subsequently, the RNAi-treated animals were washed in M9 at least five times to remove the *E. coli* bacteria and transferred to *K. rhizophila* seeded plates or *E. coli* OP50 seeded plates.

Microscopy

Nematodes were mounted onto agar pads and images were acquired using a Zeiss AXIO Imager Z1 microscope fitted with a Zeiss AxioCam HRm camera and Axiovision 4.6 (Zeiss) software. All the fluorescence images shown within the same figure panel were collected together using the same exposure time. Images were converted to 8-bit image, thresholded and quantified using ImageJ. Student's t test was used determine statistical significance. Low-magnification bright-field and GFP fluorescence images were acquired using a Zeiss AxioZoom V16, equipped with a Hammamatsu Orca flash 4.0 digital camera, and using Axiovision ZEN software.

Multiple Alignment of Protein Sequences

Multiple alignments were performed using Clustal Omega software.

*K. rhizophila* EMS Mutagenesis Screen

Mutagenesis was performed by treatment of overnight culture of *K. rhizophila* in PBS solution with 50 mM EMS for 45 minutes at 37° C. Serial dilutions of the mutagenized *K. rhizophila* cultures were plated onto LB media plates and ~2000 mutagenized bacterial colonies were picked and grown in LB solution. 500 ml of overnight culture was seeded onto SK media plates and incubated at room temperature for two days before initiating the experiments. Synchronized L1-larval stage in eft-3(q145); pgp-5p::gfp animals grown until L4-larval stage or day one of adulthood in *E. coli* OP50 seeded plates and was washed in M9 buffer at least five times before transferring to the *K. rhizophila* mutant bacterial food. The plates were visually screened after 24 hours for GFP induction.

Identification of EMS Induced Mutations by Whole Genome Sequencing

Genomic DNA extraction, library prep, Illumina MiniSeq sequencing and bioinformatics were all performed by The Sequencing Center located at Fort Collins, Colorado.

Isolation of *K. rhizophila* Carotenoids

Carotenoid isolation from *K. rhizophila* was isolated as described (Giuffrida et al., 2016) with the following modifications. *K. rhizophila* cultures grown in LB solution was washed with equal volume of water after centrifugation at 4000 RPM for 15 min. After centrifugation to remove water, equal volume of acetone was added and centrifuged again at 4000 RPM for 15 min. After removal of acetone, the bacterial pellets were extracted with methanol at 65° C. in water bath after wrapping the samples with aluminum foil to protect from light. The samples were extracted with metha-nol multiple times until all the cells were bleached. The supernatant was filtered with Whatman filter paper No1. Two-volumes of 15% sodium chloride was added to the methanol extract and after mixing equal volume of hexane was added. The yellow carotenoids were separated from the methanol-salt mix and accumulated in the hexane fraction. The hexane fraction was removed and washed at least three times with water. The hexane fraction was evaporated and the resultant carotenoid pellet was dissolved in methanol.

High Performance Liquid Chromatography

Crude methanolic extracts were separated over an Agilent Eclipse Plus C18 4.6×250 mm column with a 5-micron particle size using an Agilent 1200 HPLC equipped with a diode array detector, autosampler, column oven, solvent degasser, and binary pump. The mobile phases were (A) water vs. (B) methanol at a flow rate of 2 mL/min. The column was preequilibrated at 40° C. with 90% B prior to sample injection. Following injection, the column was washed isocratically for 5 min at 90% B before ramping to 100% B over 5 min. Eluate absorbance spectra were moni-tored from 300-700 nm.

Pull Down Experiments with Rat Liver

To identify carotenoid binding proteins, the protocol from Pilbrow et al., 2014 was used with the following modifica-tions. Protein extracts were obtained by chopping ~10 grams of adult rat liver into tiny pieces and homogenizing using Tissue—in T-PER tissue protein extraction reagent contain-ing Roche protease inhibitors. Delipidation of the extract was done using methanol-chloroform. ~10 mg of *K. rhizo-phila* carotenoids were incubated with 1 gram of protein extract for one hour at 22° C. Unbound carotenoids were removed by size-exclusion chromatography using Bio-spin P-6 (6K MWCO). The carotenoid bound protein extract was subjected to DEAE anion-exchange sepharose resin column pre-equilibrated with anion-exchange buffer A (0.05M diba-sic sodium phosphate, pH 8.0) at 4° C. The sample was allowed to flow through the column by gravity and the column was washed with anion-exchange buffer A. Proteins were eluted with 0.5M NaCl in 0.5 ml volumes. The yellow fractions were pooled, dialyzed to remove salts and concen-trated using Vivaspin centrifugal concentrator columns. The yellow fractions were separated on 4-12% Native PAGE and the yellow-orange band visible was excised and mass spec-trometry was conducted for identifying proteins.

Putative "Decaprenoxanthin" Carotenoid Biosynthetic Clus-ter from Microbes

Putative carotenoid biosynthetic cluster of *Leifsonia xyli* (Lxx15630, Lxx15620, Lxx15610, Lxx15600, Lxx15590, and Lxx15580) (Monteiro-Vitorello et al., 2004), *Microbac-terium testaceum* (MTES_3133, MTES_3132, MTES_3131, MTES_3130, MTES_3129, and MTES_3128) (Morohoshi et al., 2011), *Cellvibrio gilvus* (Celgi_1516, Celgi_1515, Celgi_1514, Celgi_1513, Celgi_1512, and Celgi_1511) (Christopherson et al., 2013), *Cellulomonas fimi* (Celf_3171, Celf_3170, Celf_3169, Celf_3168, Celf_3167, and Celf_3166) (Christopherson et al., 2013), *Sanguibacter keddieii* (Sked_12750, Sked_12760, Sked_12770, Sked_12780, Sked_12790, and Sked_12800) (Ivanova et al., 2009), *Jonesia denitrificans* (Jden_0342, Jden_0341, Jden_0340, Jden_0339, Jden_0338, and Jden_0337) (Pukall et al., 2009), *Mycetocola manganoxydans* (D9V29_RS08865, D9V29_RS08870, D9V29_RS08875, D9V29_RS08880, D9V29_RS08885, and D9V29_RS08890), *Mycetocola miduiensis* (BM197_RS02470, BM197_RS02475, BM197_RS02480, BM197_RS02485, BM197_RS02490, and BM197_RS02495), *Cryobacterium psychrotolerans* (BLQ39_RS02180, BLQ39_RS02185, BLQ39_RS02190, BLQ39_RS02195, BLQ39_RS02200, and BLQ39_RS02205), *Subtercola boreus* (B7R21_RS02695, B7R21_RS02700, B7R21_RS02705, B7R21_RS02710, B7R21_RS02715, and B7R21_RS02720), *Herbiconiux solani* (HSO01S_RS07000, HSO01S_RS07005, HSO01S_RS07010, HSO01S_RS07015, HSO01S_RS07020, and HSO01S_RS07025), *Microbacte-rium phyllosphaerae* (D3H67_RS09120, D3H67_RS09125, D3H67_RS09130, D3H67_RS09135, D3H67_RS09140, and D3H67_RS09145), *Leifsonia aquatica* (N136_RS22055, N136_RS22060, N136_RS22065, N136_RS22070, N136_RS22075, and N136_RS22080), *Microbacterium esteraromaticum* (B4U78_RS09520, B4U78_RS09525, B4U78_RS09530, B4U78_RS09535, B4U78_RS09540, and B4U78_RS09545),

*Plantibacter* sp. H53 (A4X17_RS18565, A4X17_RS18570, A4X17_RS18575, A4X17_RS18580, A4X17_RS18585, and A4X17_RS18590), *Curtobacterium* sp. (ASF23_RS14315, ASF23_RS14320, ASF23_RS14325, ASF23_RS14330, ASF23_RS14335, and ASF23_RS14340), *Microterri-cola pindariensis* (GY24_RS04745, GY24_RS04750, GY24_RS04755, GY24_RS04760, GY24_RS04765, and GY24_RS04770), *Frondihabitans* sp. (EDF46_RS08000, EDF46_RS08005, EDF46_RS08010, EDF46_RS08015, EDF46_RS08020, and EDF46_RS08025), *Salinibacte-rium xinjiangense* (SAMN06296378_0676, SAMN06296378_0677, SAMN06296378_0678, SAMN06296378_0679, SAMN06296378_0680, and SAMN06296378_0681), *Agromyces* sp. (AVP42_RS01110, AVP42_RS01115, AVP42_RS01120, AVP42_RS01125, AVP42_RS01130, and AVP42_RS01135), *Microbacte-rium barkeri* (MBR4_RS00310, MBR4_RS00315, MBR4_RS00320, MBR4_RS00325, MBR4_RS00330, and MBR4_RS00335), *Arthrobacter koreensis* (BN2404_RS04370, BN2404_RS04375, BN2404_RS04380, BN2404_RS04385, BN2404_RS04390, and BN2404_RS04395), *Cryobac-terium roopkundense* (GY21_RS00565, GY21_RS00570, GY21_RS00575, GY21_RS00580, GY21_RS00585, and GY21_RS00590), *Microbacte-rium oxydans* (RN51_RS07325, RN51_RS07330, RN51_RS07335, RN51_RS07340, RN51_RS07345, and RN51_RS07350), *Arthrobacter luteolus* (AL3_RS02570, AL3_RS02575, AL3_RS02580, AL3_RS02585, AL3_RS02590, and AL3_RS02595), *Cryobacterium aureum* (CJ028_RS03575, CJ028_RS03580, CJ028_RS03585, CJ028_RS03590, CJ028_RS03595, and CJ028_RS03600), *Curtobacte-rium ammoniigenes* (CAM01S_RS13455, CAM01S_RS13460, CAM01S_RS13465, CAM01S_RS13470, CAM01S_RS13475, and CAM01S_RS13480), *Oerskovia enterophila* (OJAG_RS08920, OJAG_RS08925, OJAG_RS08930, OJAG_RS08935, OJAG_RS08940, and OJAG_RS08945), *Microbacterium paraoxydans* (SAMN04489809_1122, SAMN04489809_1123, SAMN04489809_1124, SAMN04489809_1125, SAMN04489809_1126, and SAMN04489809_1127), *Agromyces subbeticus* (H521_RS21795, H521_RS21800, H521_RS0106365, H521_RS0106370, H521_RS21805, and H521_RS0106380), *Arthrobacter crystallopoietes* (D477_RS18370, D477_RS18375, D477_RS18380, D477_RS18385, and D477_RS18390, D477_RS18395), *Georgenia satyanarayanai* (DSZ44_RS04745, DSZ44_RS04750, DSZ44_RS04755, DSZ44_RS04760, DSZ44_RS04765, and DSZ44_RS04770), *Microbacterium trichothecenolyticum* (RS82_RS03115, RS82_RS03120, RS82_RS03125, RS82_RS03130, RS82_RS03135, and RS82_RS03140), *Arthrobacter woluwensis* (C6401_RS03950, C6401_RS03955, C6401_RS03960, C6401_RS03965, C6401_RS03970, and C6401_RS03975), *Promicromonospora kroppenstedtii* (PROKR_RS13815, PROKR_RS13820, PROKR_RS13825, PROKR_RS13830, PROKR_RS13835, and PROKR_RS13840), *Cellulomonas cellasea* (Q760_RS04595, Q760_RS04600, Q760_RS04605, Q760_RS18340, Q760_RS04615, and Q760_RS04620), *Agromyces cerinus* (BUR99_RS12060, BUR99_RS12065, BUR99_RS12070, BUR99_RS12075, BUR99_RS12080, and BUR99_RS12085), *Agreia pratensis* (B9Y86_RS06900, B9Y86_RS06905, B9Y86_RS06910, B9Y86_RS06915, B9Y86_RS06920 and B9Y86_RS06925), *Microbacterium laevanformans* (OR221_3062, OR221_3063, OR221_3064, OR221_3065, OR221_3066, and OR221_3067), *Arthrobacter stackebrandtii* (CVV67_17780, CVV67_17785, CVV67_17790, CVV67_17795, CVV67_17800, and CVV67_17805), *Paeniglutamicibacter gangotriensis* (ADIAG_RS03760, ADIAG_RS03765, ADIAG_RS03770, ADIAG_RS03775, ADIAG_RS03780, and ADIAG_RS03785), *Microbacterium trichothecenolyticum* (RS82_RS03115, RS82_RS03120, RS82_RS03125, RS82_RS03130, RS82_RS03135, and RS82_RS03140), *Arthrobacter livingstonensis* (CVV68_RS19330, CVV68_RS19335, CVV68_RS19340, CVV68_RS19345, CVV68_RS19350, and CVV68_RS19355), *Demequina lutea* (AOP76_RS09030, AOP76_RS09035, AOP76_RS09040, AOP76_RS09045, AOP76_RS09050, and AOP76_RS09055), *Zhihengliuella halotolerans* (CUR88_RS12685, CUR88_RS12690, CUR88_RS12695, CUR88_RS12700, CUR88_RS12705, and CUR88_RS12710), *Paeniglutamicibacter antarcticus* (BN2261_RS08280, BN2261_RS08285, BN2261_RS08290, BN2261_RS08295, BN2261_RS08300, and BN2261_RS08305), *Janibacter melonis* (EEW87_RS00715, EEW87_RS00720, EEW87_RS00725, EEW87_RS00730, EEW87_RS00735, and EEW87_RS00740), *Microbacterium arborescens* (DOU46_RS02280, DOU46_RS02285, DOU46_RS02290, DOU46_RS02295, DOU46_RS02300, and DOU46_RS02305), *Agreia pratensis* (B9Y86_RS06900, B9Y86_RS06905, B9Y86_RS06910, B9Y86_RS06915, B9Y86_RS06920, and B9Y86_RS06925), *Agreia bicolorata* (TZ00_RS04480, TZ00_RS04485, TZ00_RS19215, TZ00_RS04495, TZ00_RS04500, and TZ00_RS04505), *Arthrobacter psychrochitiniphi-

*lus* (CVS30_RS02785, CVS30_RS02790, CVS30_RS02795, CVS30_RS02800, CVS30_RS02805, and CVS30_RS02810), *Microterricola pindariensis* (GY24_RS04745, GY24_RS04750, GY24_RS04755, GY24_RS04760, GY24_RS04765, and GY24_RS04770), *Microbacterium indicum* (H576_RS15860, H576_RS0112930, H576_RS0112935, H576_RS0112940, H576_RS0112945, and H576_RS15865), *Homoserinimonas* sp. (DL891_RS01870, DL891_RS01875, DL891_RS01880, DL891_RS01885, DL891_RS01890, and DL891_RS01895), *Cryobacterium levicorallinum* (SAMN05216274_11068, SAMN05216274_11069, SAMN05216274_11070, SAMN05216274_11071, SAMN05216274_11072, and SAMN05216274_11073), *Frigoribacterium* sp. (EDF18_RS14355, EDF18_RS14360, crtI, EDF18_RS14370, EDF18_RS14375, and EDF18_RS14380), *Cryobacterium luteum* (SAMN05216281_10883, SAMN05216281_10884, SAMN05216281_10885, SAMN05216281_10886, SAMN05216281_10887, and SAMN05216281_10888), *Cellulomonas carbonis* (N868_RS13600, N868_RS13605, N868_RS13610, N868_RS13615, N868_RS13620, and N868_RS13625), *Okibacterium fritillariae* (B5X75_RS14075, B5X75_RS14080, B5X75_RS14085, B5X75_RS14090, B5X75_RS14095, and B5X75_RS14100), *Glycomyces sambucus* (BLS99_RS13650, BLS99_RS13655, BLS99_RS13660, BLS99_RS13665, BLS99_RS13670, and BLS99_RS13675), *Krasilnikoviella flava* (B5Y66_RS20515, B5Y66_RS20520, B5Y66_RS20525, B5Y66_RS20530, B5Y66_RS20535, and B5Y66_RS20540), *Actinotalea ferrariae* (N866_01505, N866_01510, N866_01515, N866_01520, N866_01525, and ubiA), *Lysinimicrobium soli* (AOM04_RS11780, AOM04_RS11785, AOM04_RS11790, AOM04_RS11795, AOM04_RS11800, and AOM04_RS11805), *Luteimicrobium subarcticum* (CLV34_RS08275, CLV34_RS08280, CLV34_RS08285, CLV34_RS08290, CLV34_RS08295, and CLV34_RS08300), *Promicromonospora kroppenstedtii* (PROKR_RS13815, PROKR_RS13820, PROKR_RS13825, PROKR_RS13830, PROKR_RS13835, and PROKR_RS13840), *Tersicoccus phoenicis* (BKD30_RS05860, BKD30_RS05865, BKD30_RS05870, BKD30_RS05875, BKD30_RS05880, and BKD30_RS05885), *Sinomonas humi* (LK10_RS09295, LK10_RS09300, LK10_RS09305, LK10_RS09310, and LK10_RS09315), *Pseudarthrobacter phenanthrenivorans* (RM50_RS01675, RM50_RS01680, RM50_RS01685, RM50_RS01690, RM50_RS01695, and RM50_RS01700), *Acaricomes phytoseiuli* (C501_RS0107225, C501_RS0107230, C501_RS0107235, C501_RS0107240, C501_RS0107245, and C501_RS0107250), *Leucobacter musarum* (AMS67_RS10795, AMS67_RS10800, AMS67_RS10805, AMS67_RS10810, AMS67_RS10815, and AMS67_RS10820), *Ornithinimicrobium pekingense* (K330_RS19765, K330_RS0107130, K330_RS19770, K330_RS19775, K330_RS0107145, and K330_RS0107150), *Citricoccus* sp. (CITRI_RS16000, CITRI_RS0102550, CITRI_RS0102555, CIT- RI_RS16005, CITRI_RS0102565, and CIT-RI_RS0102570), and *Arthrobacter arilatensis* (AARI_13710, AARI_13720, AARI_13730, AARI_13740, AARI_13760, and AARI_13750) (Monnet et al., 2010) are very similar have a similar size and show the same organization as in the genome of *K. rhizophila*. In *Corynebacterium glutamicum* (cg0723, cg0721, cg0720, cg0719, cg0718, and cg0717) (Kalinowski et al., 2003) and *Corynebacterium efficiens* (HMPREF0290_1086, HMPREF0290_1088, HMPREF0290_1089, HMPREF0290_1090, HMPREF0290_1091, and HMPREF0290_1092) (Nishio et al., 2003) the decaprenoxanthin producing gene cluster is similar in size and organization to that of *K. rhizophila* except for the insertion of an unrelated gene cg0722 between crtE and crtB in *C. glutamicum* or HMPREF0290_1088 in *C. efficiens*. Also, in *Corynebacterium glutamicum*, an additional carotenoid cluster (NCg10600, NCg10598, NCg10597, NCg10596, NCg10595, and NCg10594) in also present in the genome. In *Kytococcus sedentarius*, the genes responsible for carotenoid production (Ksed_13840, Ksed_13830, Ksed_13820, Ksed_13810, Ksed_13800) are arranged in the same cluster while Ksed_16070, which encodes for geranylgeranyl pyrophosphate synthase is located elsewhere in the genome (Sims et al., 2009).

In *Brevibacterium mcbrellneri*, the genes responsible for carotenoid production (HMPREF0183_0793, HMPREF0183_0794, HMPREF0183_0795, HMPREF0183_0796, and HMPREF0183_0797) are located in the same cluster while HMPREF0183_0437, which encodes for polyprenyl synthetase is located elsewhere in the genome.

In *Beutenbergia cavernae*, the genes responsible for carotenoid production (Bcav_3492, Bcav_3491, Bcav_3490, Bcav_3489, Bcav_3488) are located in the same cluster while Bcav_0970, which encodes for polyprenyl synthetase is located elsewhere in the genome (Land et al., 2009).

In *Brachybacterium faecium* (Bfae_04470, Bfae_04440, Bfae_04430, Bfae_04420, Bfae_04410, and Bfae_04400) (Lapidus et al., 2009) the carotenoid biosynthetic cluster is similar in size and organization to that of *K. rhizophila* except for the insertion of two unrelated genes Bfae_04460 and Bfae_04450 between Bfae_04470 and Bfae_04440.

In *Cellulomonas flavigna* (Cfla_2888, Cfla_2889, Cfla_2890, Cfla 2891, and Cfla_2892) (Abt et al, 2010) all the genes responsible for carotenoid production are present except for Cfla_2893 which is a likely pseudogene because of frame-shift mutation.

Decaprenoxanthin was the first C50 carotenoid discovered from *Flavobacterium dehydrogenans* (now known as *Agromyces mediolanus* (Liaaen-Jensen et al., 1968)).

Many bacteria including *Agromyces mediolanus* (Liaaen-Jensen et al., 1968), Aureobacterium sp. (Fukuoka et al., 2004), *Arthrobacter glacialis* (Arpin et al., 1975), *Arthrobacter arilatensis* (Sutthiwong et al., 2014), *Cellulomonas biazotea* (Weeks et al., 1980), *Citriococcus sp*, and *Corynebacterium glutamicum* (Krubasik et al., 2001) are known to produce decaprenoxanthin.

Figure 5A:
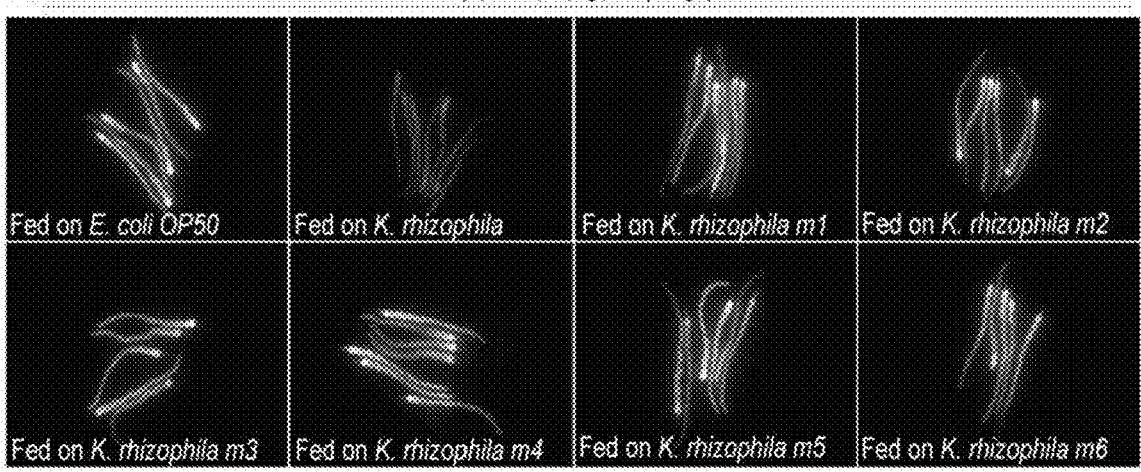
FIGS. 5A-G
A) *K. rhizophila* feeding inhibited induction of pgp-5p:: gfp in eft-3(q145); pgp-5p::gfp animals, while in *K. rhizophila* mutants, pgp-5p::gfp expression was not affected.
B) *K. rhizophila* feeding suppressed pgp-5p::gfp induction in eft-3(q145); pgp-5p::gfp animals within 12 hours of feeding.
C) While pgp-5p::gfp animals fed on vrs-2 dsRNA and transferred to *E. coli* showed induction of gfp, in animals transferred to *K. rhizophila* plates, pgp-5p::gfp expression was reduced.
D) While pgp-5p::gfp animals fed on rpl-1 dsRNA and transferred to *E. coli* showed induction of gfp, in animals transferred to *K. rhizophila* plates, pgp-5p::gfp expression was reduced.
E) *K. rhizophila* feeding reduced pgp-5p::gfp induction in eft-3(q145); pgp-5p::gfp animals significantly, while in *K. rhizophila* mutants, the pgp-5p::gfp expression was not affected.
F) Colony color of *K. rhizophila* wildtype was different from the colony color of six mutants.
G) Colony color of *K. rhizophila* mutants observed from a EMS screen.
Figure 5B:
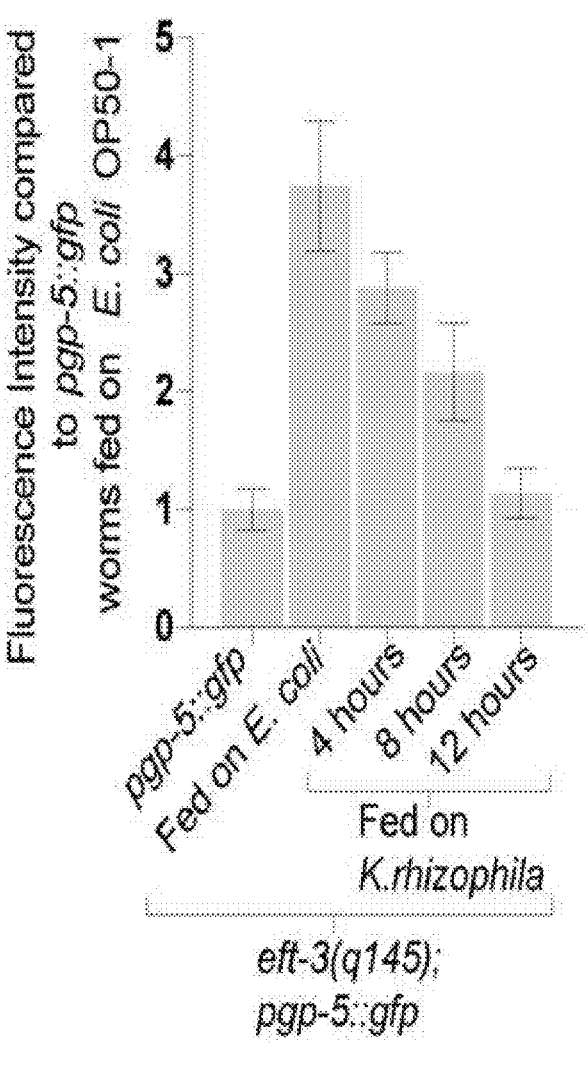

Example 1. Bacterial Carotenoids Suppress *C. elegans* Surveillance of Translational Deficits Expression of particular suites of cytochrome p450, ABC transporter, UDP-glycosyl transferase genes among the approximately 500 *C. elegans* xenobiotic detoxification genes, for example, the *C. elegans* ABC transporter gene pgp-5, can be induced by toxin, RNAi, or mutational inhibition of ribosomal proteins, tRNA synthetases, and other genes implicated in translation (Govindan et al., 2015). Even when the defects in translation are limited to the germline, for example, in the *C. elegans* eft-3(q145) mutant, a mutation in the germline isoform of the translation elongation factor-1 (where translation in somatic cells and somatic development is normal, but translation in the germline cells is disabled and the germline does not proliferate), the expression of the ABC transporter gene fusion pgp-5p::gfp was strongly induced in the intestine when the animals are fed the benign *E. coli* OP50 (FIG. 5A). Feeding *K. rhizophila* rather than *E. coli* to *C. elegans* eft-3(q145); pgp-5p::gfp disrupted the normal induction of pgp-5p::gfp (FIGS. 5A&B). *K. rhizophila* is a gram-positive coccus of the phylum Actinobacteria, a clade rich in drug biosynthetic pathways. *K. rhizophila* species are found in various ecological niches including soils and the *C. elegans* gut microbiome in natural populations of nematodes from orchards (Felix et al., 2010). *K. rhizophila* species are normal inhabitants of skin and mucous membrane of human and animals, but can be associated with human infections.

Figure 5C:
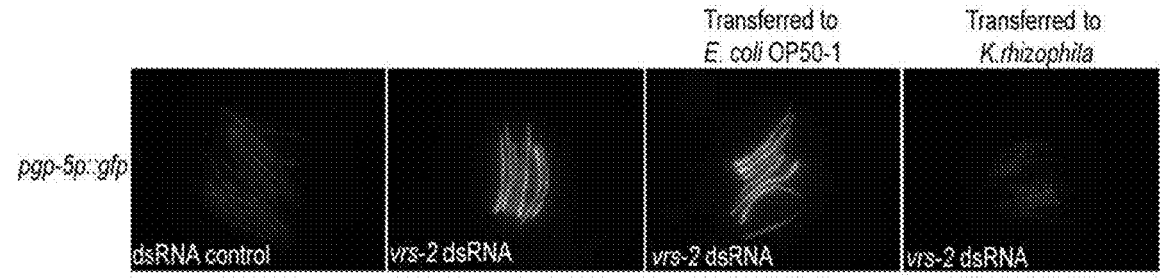
Figure 5D:
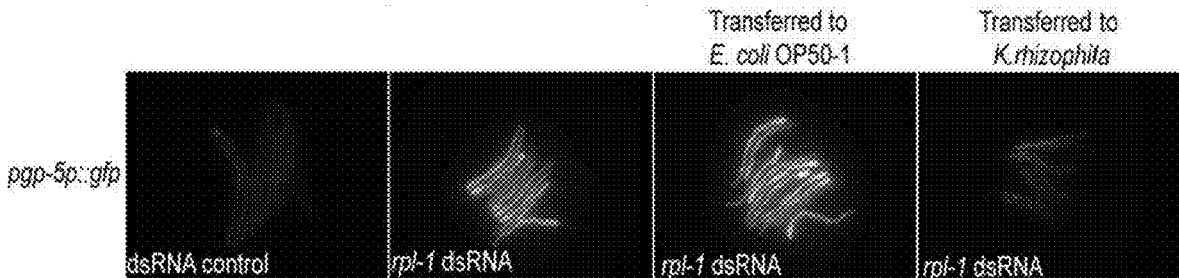
Figure 5E:
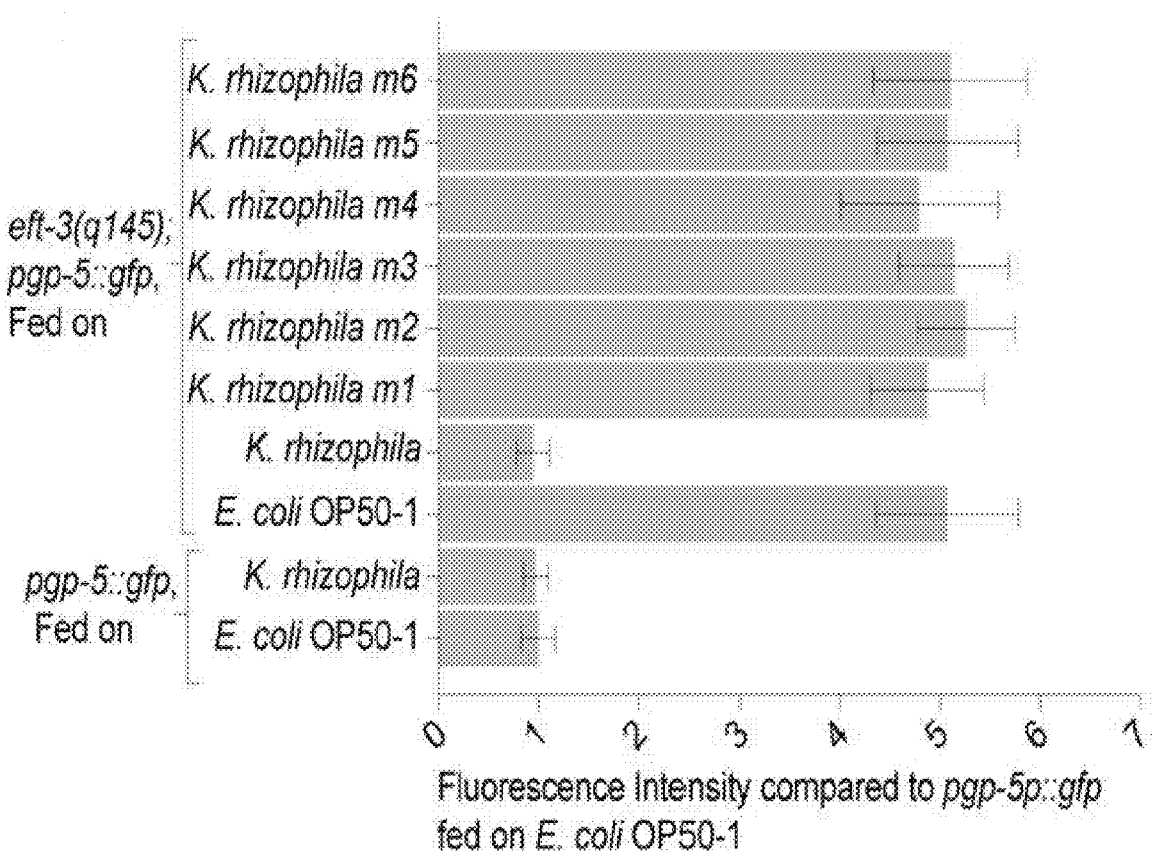

To establish that *K. rhizophila* can suppress the surveillance of a range of defects in translation, the induction of xenobiotic detoxification response to RNAi of other ribosomal proteins was tested. Synchronized L1-larval stage pgp-5p::gfp animals were fed on *E. coli* expressing either rpl-1 dsRNA or vrs-2 dsRNA, which inhibit the production of the *C. elegans* RPL-1 ribosomal protein and the VRS-2 tRNA synthetase. When these animals reached adulthood, they were transferred to either *E. coli* OP50 containing plates or *K. rhizophila* seeded plates and the scored for GFP induction after 24 hours. In animals fed on either vrs-2 dsRNA or rpl-1 dsRNA and transferred to *E. coli* OP50 containing plates, pgp-5p::gfp was induced. By contrast, in animals fed on either rpl-1 dsRNA or vrs-2 dsRNA and transferred to *K. rhizophila* plates, pgp-5p::gfp expression was abrogated (FIGS. 5C&D). The suppression of surveillance pathways by *K. rhizophila* is specific for translation stress because *K. rhizophila* does not suppress the induction of mitochondrial stress response or endoplasmic reticulum stress response (Govindan et al., 2015).

Figure 5F:
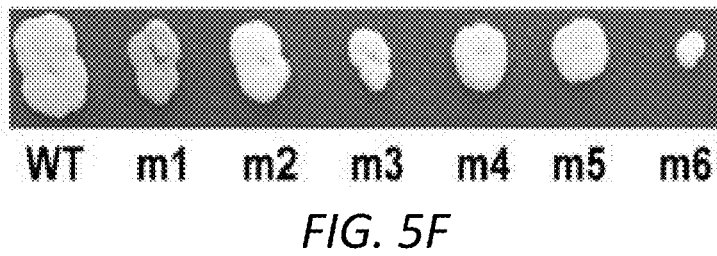
Figure 5G:
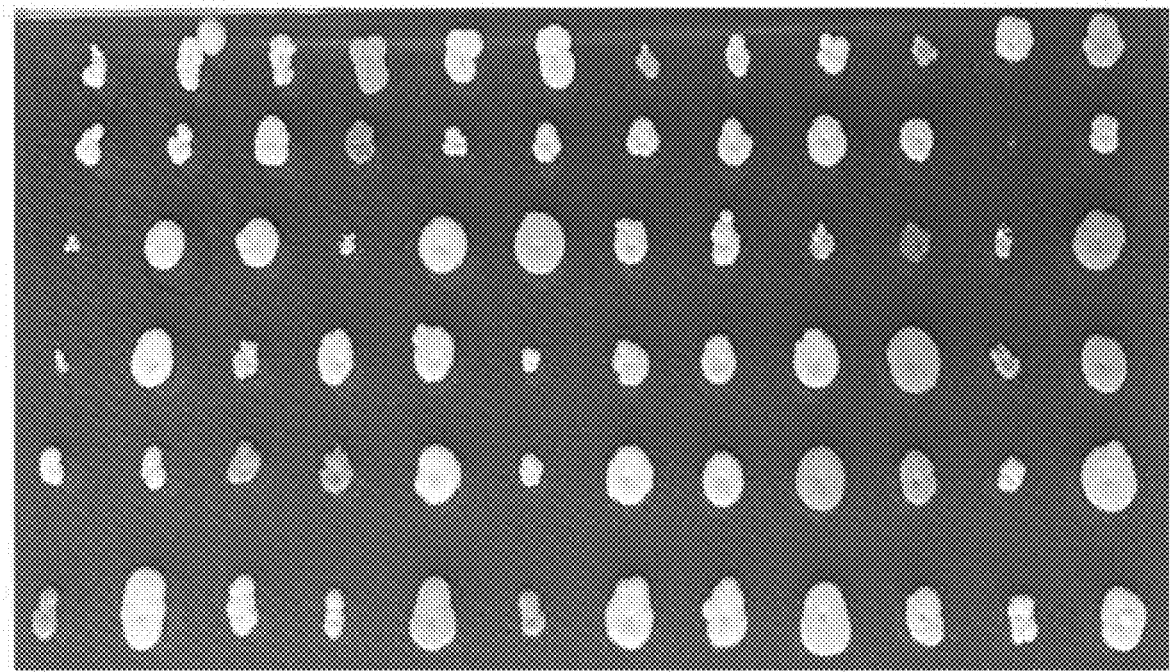
Figure 6A:
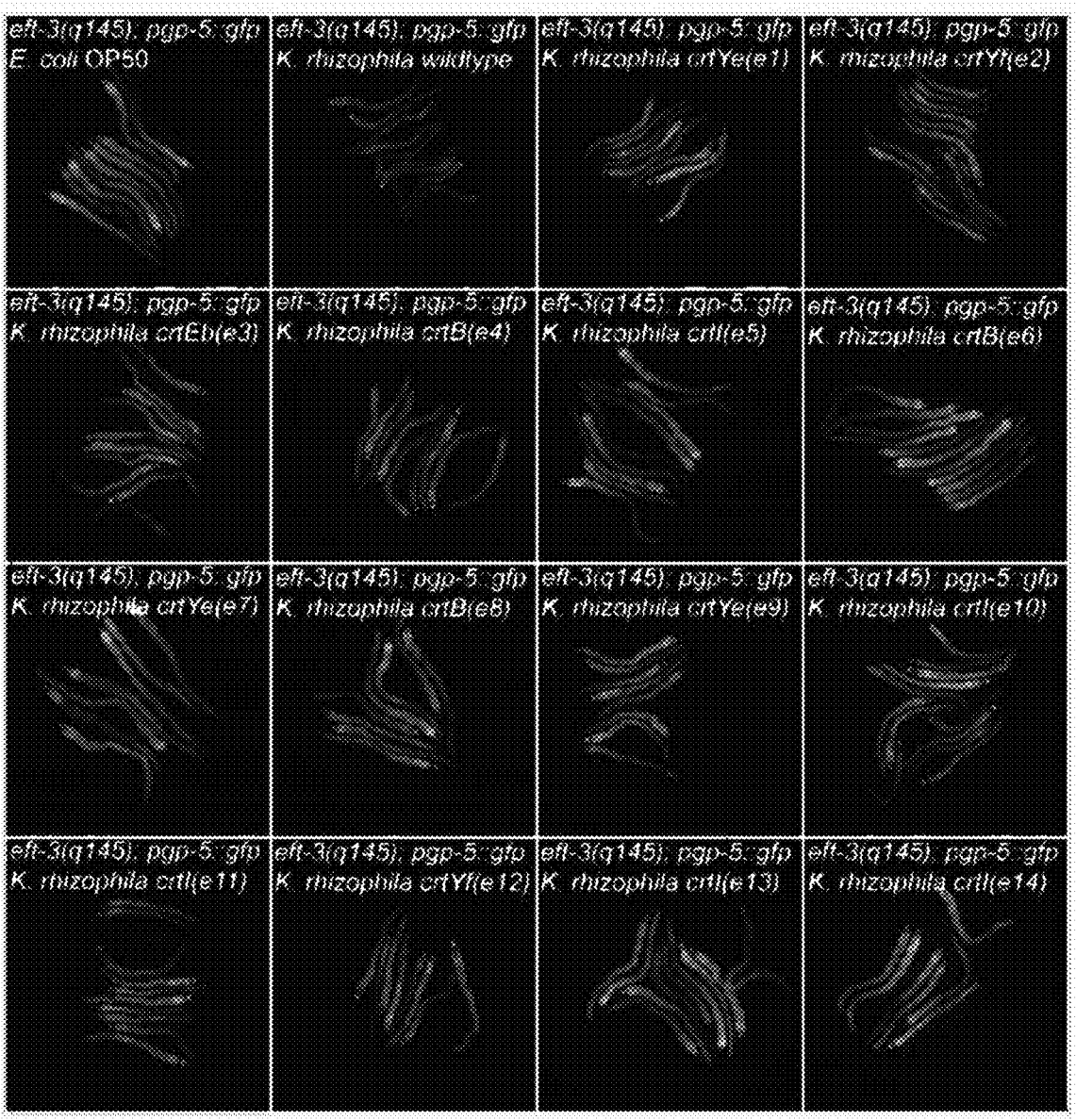
FIGS. 6A-C
A) *K. rhizophila* mutants failed to suppress induction of pgp-5p::gfp in eft-3(q145); pgp-5p::gfp animals.
B) A discoloration phenotype observed from 23 genome sequenced mutants.

To identify the *K. rhizophila* pathways responsible for the inhibition of pgp-5p::gfp induction in a *C. elegans* strain carrying a genetic deficit in translation (eft-3(q145), a forward genetic screen was conducted for *K. rhizophila* mutant strains that are defective in the inhibition of pgp-5p::gfp induction. About 2000 individual *K. rhizophila* strains that grew normally on bacterial LB plates after EMS mutagenesis were fed to eft-3(q145); pgp-5p::gfp animals. These 2000 individual wells of distinct *K. rhizophila* mutant strains were screened for mutant bacterial strains that failed to suppress pgp-5p::gfp induction in the eft-3(q145); pgp-5p::gfp animals. Six *K. rhizophila* mutant strains were identified that failed to induce pgp-5p::gfp in eft-3(q145); pgp-5p::gfp animals (FIGS. 5A&E). Visual inspection revealed that all these mutant strains had defects in colony pigmentation compared to wild type *K. rhizophila* (FIG. 5F). Wildtype *K. rhizophila* is yellow, whereas the six mutant colonies were red or white or orange. Using this discoloration phenotype, we screened ~500,000 bacterial colonies generated by EMS mutagenesis visually for mutants with a discoloration phenotype. We isolated 71 mutants that were discolored (FIG. 5G). The 71 mutants along with 25 control non-discolored mutants generated in the same EMS mutagenesis were tested on eft-3(q145); pgp-5p::gfp animals and scored for GFP induction. All 71 discoloration mutants failed to suppress pgp-5p::gfp induction in the *C. elegans* eft-3(q145) mutant, whereas the 25 normally colored strains suppressed pgp-5p::gfp induction (FIG. 6A; FIG. 1A-C).

Figure 1D:
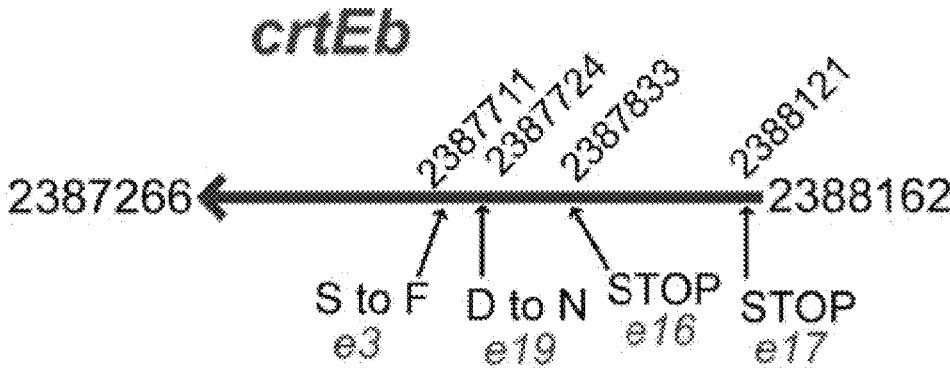
Figure 1D:
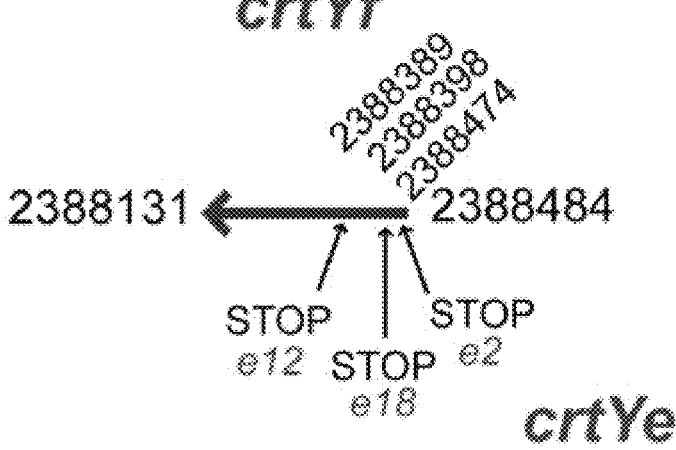
Figure 1D:
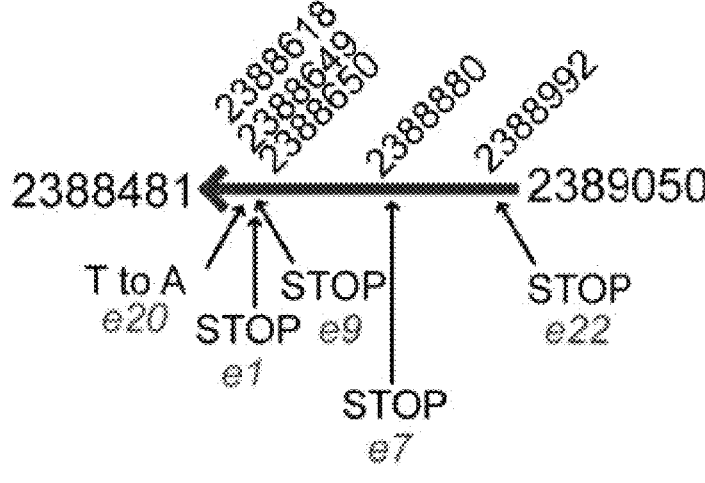
Figure 1E:
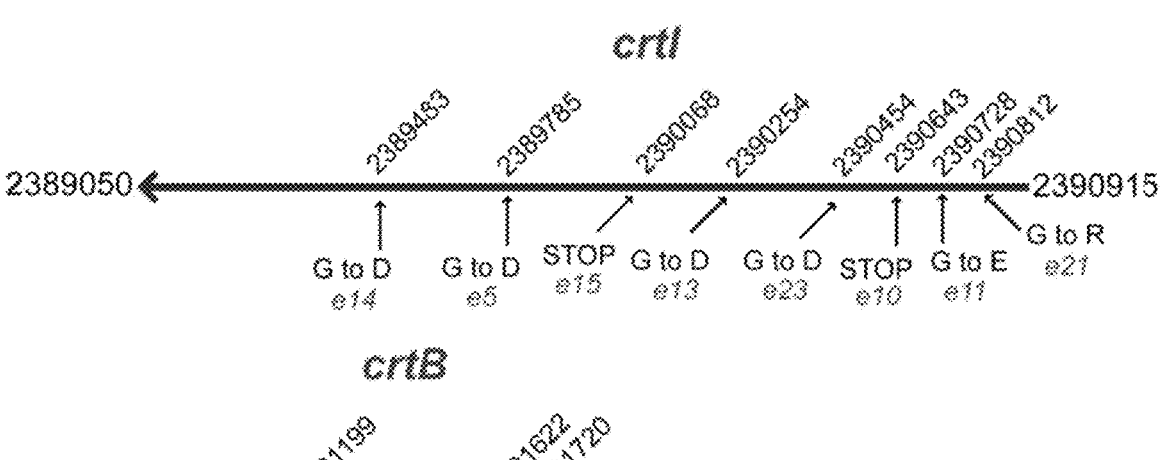
Figure 1E:
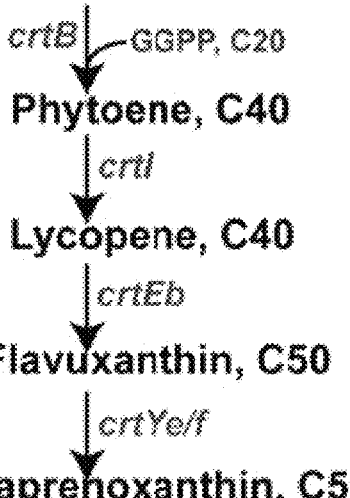
Figure 6B:
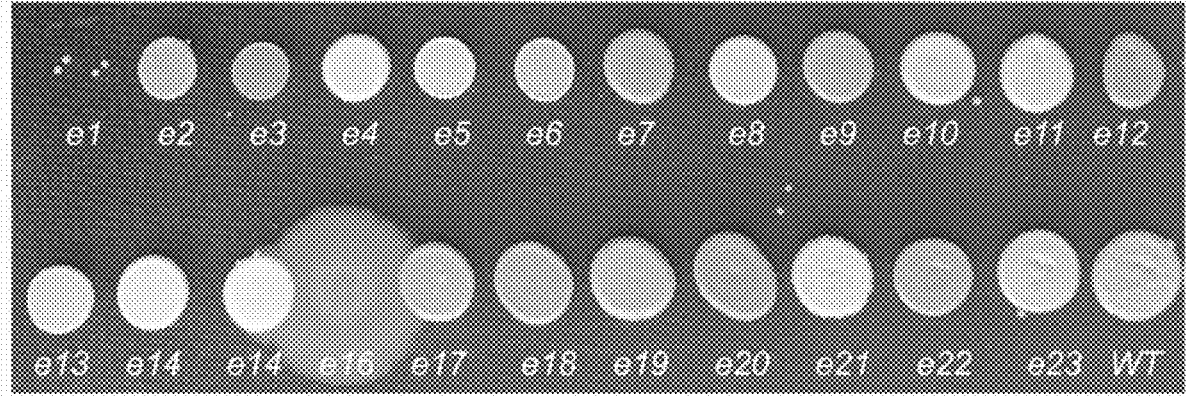

Genome sequencing of 23 EMS-mutagenized *K. rhizophila* mutants that failed to suppress pgp-5p::gfp induction in the eft-3(q145) mutant revealed that each carried a mutation in one of six carotenoid biosynthetic cluster genes (FIG. 6B; FIG. 1C-E). Carotenoids are yellow to red colored pigments, which are produced by a terpenoid biosynthetic pathway. The genome of *K. rhizophila* contains an operon that encodes predicted carotenoid (crt) biosynthetic genes (Takarada et al., 2008). These include crtE (KRH_20850; encoding GGPP synthase), crtB (KRH_20840; encoding phytoene synthase), crtI (KRH_20830; encoding phytoene desaturase), crtEb (KRH_20800; encoding lycopene elongase), crtYe (KRH_20820; encoding $C_{50}$ carotenoid epsilon cyclase) and crtYf (KRH_20810; encoding $C_{50}$ carotenoid epsilon cyclase) (FIG. 1C-E). The reaction catalyzed by GGPP synthase CrtE, phytoene synthase CrtB and phytoene desaturase CrtI based on orthology are predicted to mediate steps in the production of lycopene (Klassen et al., 2010; Krubasik et al., 2001). CrtEb and CrtYe/f cyclases catalyze the biosynthesis of $C_{50}$ carotenoid from lycopene. $C_{50}$ carotenoids are rare in nature and very few of them have been characterized (Krubasik et al., 2001a; Krubasik et al., 2001b; Norgard et al., 1970; Tao et al., 2007; Netzer et al., 2010).

Figure 7:

Even though there are several microbes that contain the CrtEb and CrtYe/f genes (FIG. 7), to date the only genetically and biochemically well-characterized $C_{50}$ carotenoid is decaprenoxanthin from *C. glutamicum* (Heider et al., 2012). In *C. glutamicum*, the enzymes CrtEb, CrtYe, and CrtYf convert lycopene to the $C_{50}$ carotenoid decaprenoxanthin (Krubasik et al., 2001a; Krubasik et al., 2001b) (FIG. 1E). This reaction in carried out in two steps: CrtEb catalyzes the elongation of $C_{40}$ acyclic lycopene to acyclic $C_{50}$ carotenoid flavuxanthin (Krubasik et al., 2001a; Krubasik et al., 2001b). The products of CrtYe and CrtYf, which combine to form a $C_{50}$ cyclase then catalyze the conversion of $C_{50}$ carotenoid flavuxanthin to decaprenoxanthin (Krubasik et al., 2001a; Krubasik et al., 2001b). *K. rhizophila* crtYe and crtYf are 38% and 34% identical to *C. glutamicum* crtYe and crtYf respectively. Therefore, the yellow pigment produced by *K. rhizophila* may belong to the decaprenoxanthin $C_{50}$-subfamily.

Figure 6C:
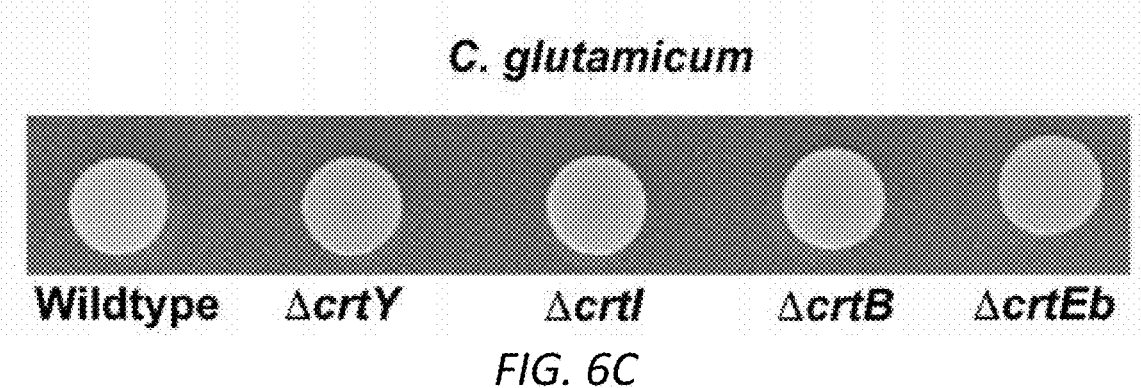
Figure 8:
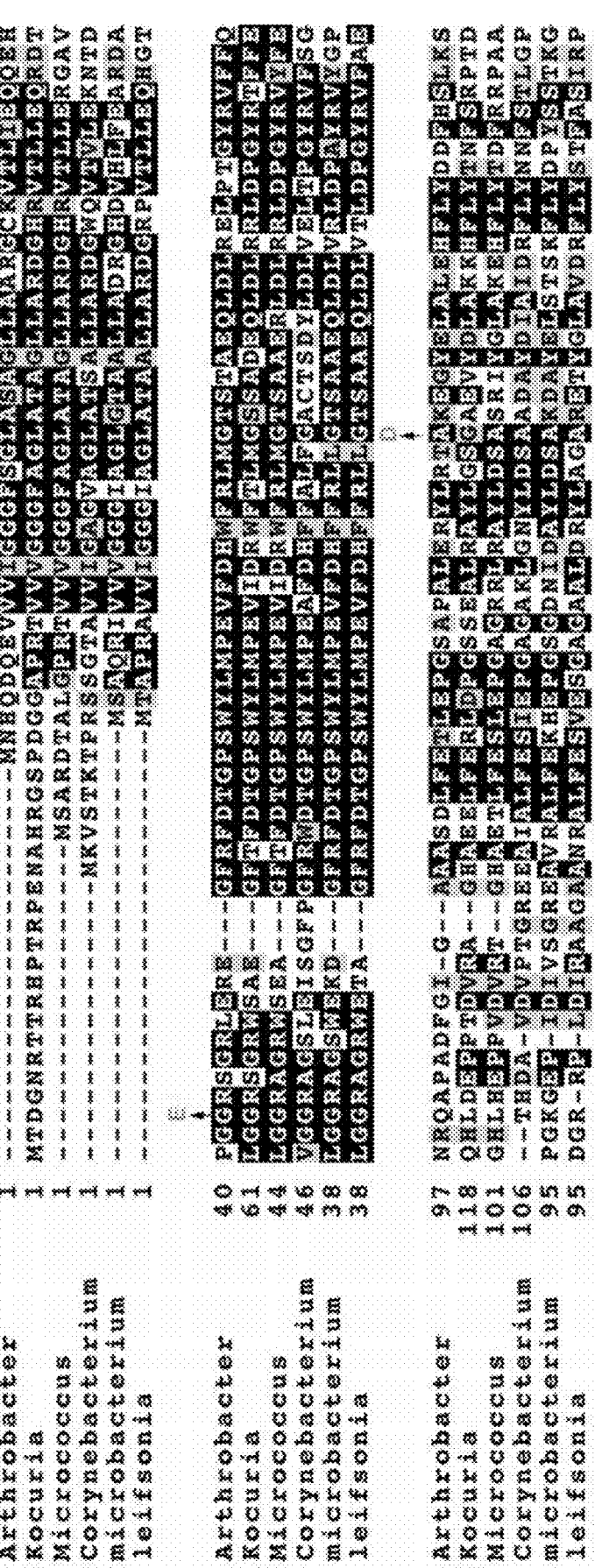
Figure 9:
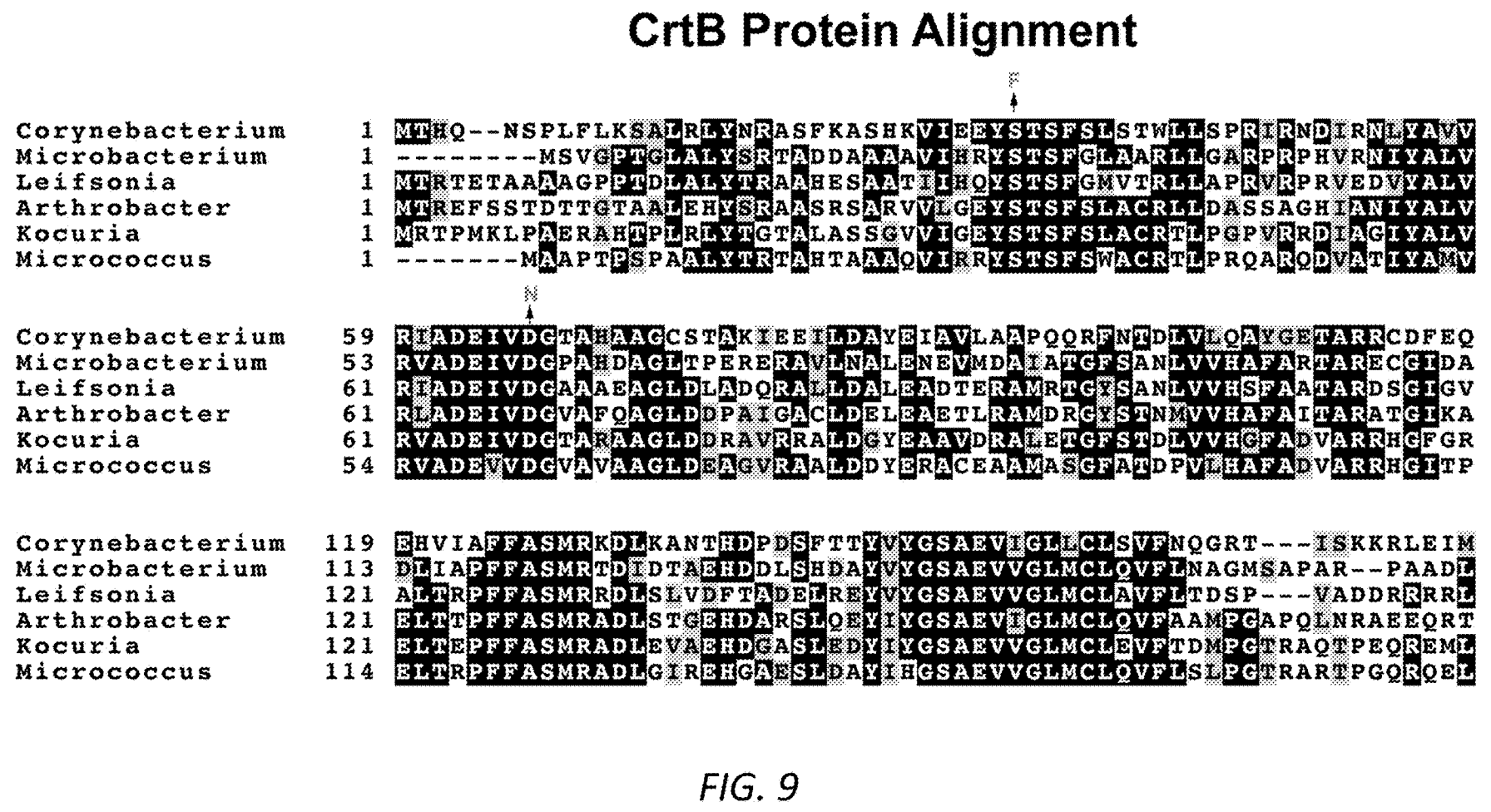
Figure 10:
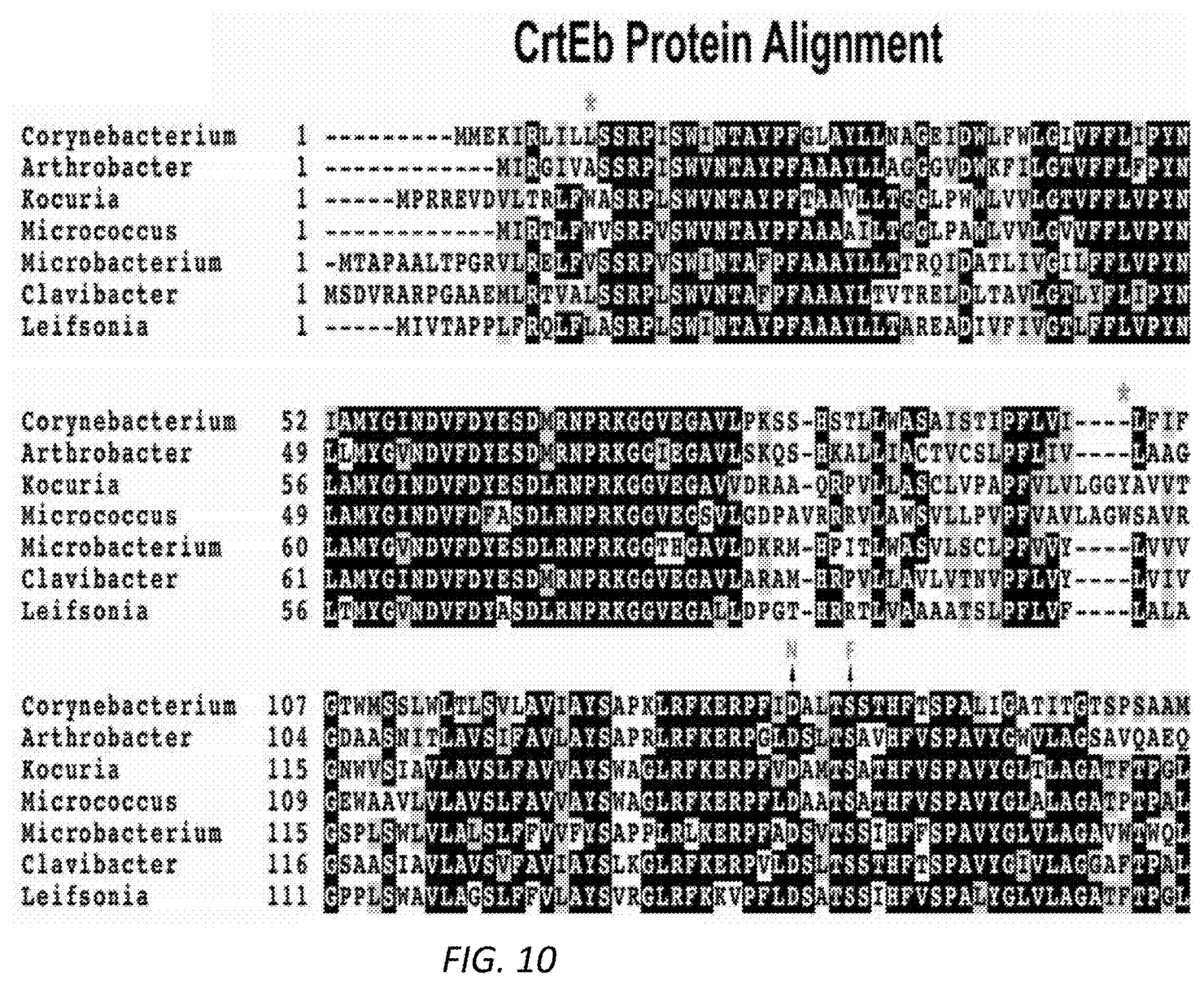
Figure 10:
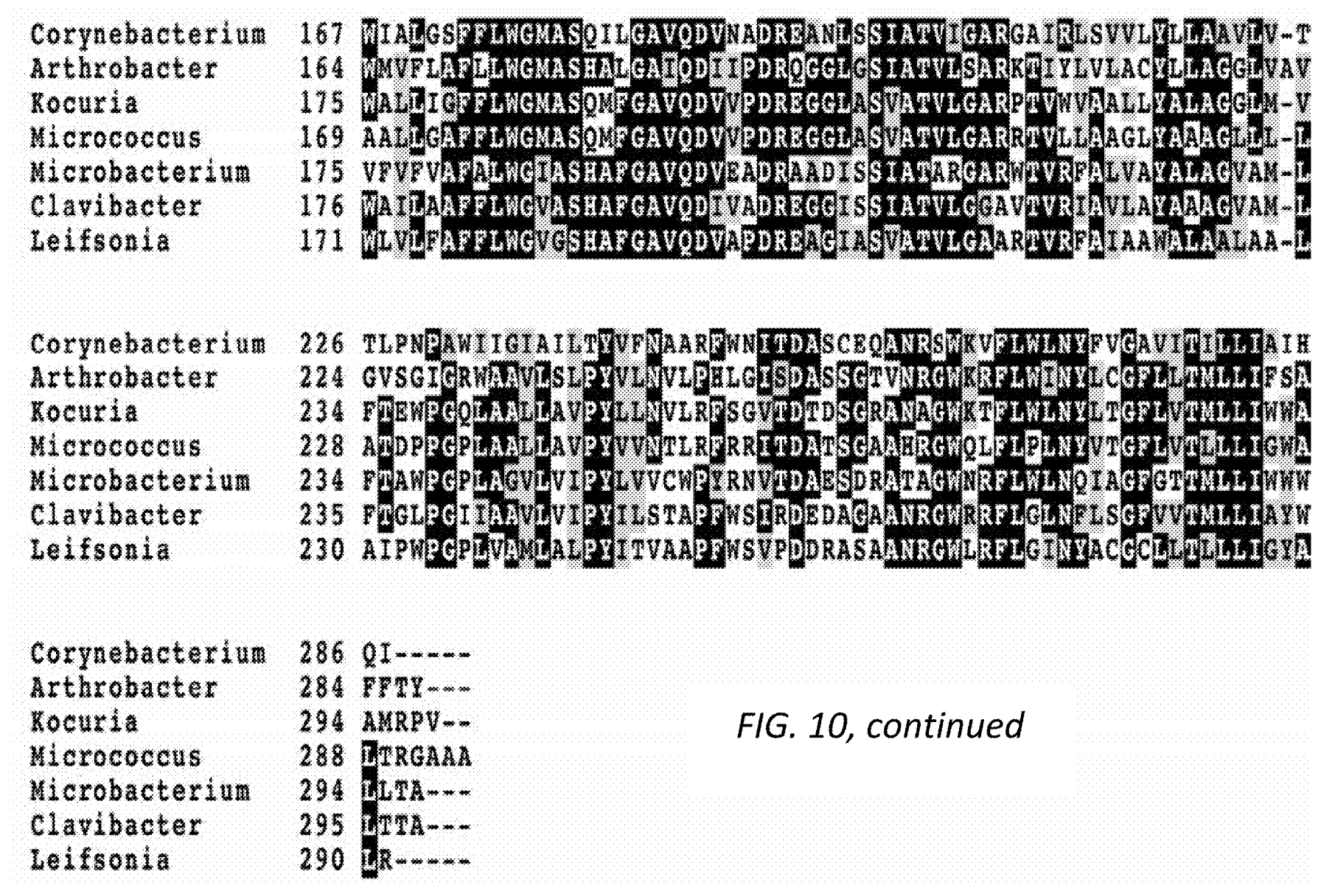

From the genetic screen of *K. rhizophila*, multiple mutations were obtained in crtI, which encodes phytoene desaturase, including six missense mutations (e21, e11, e23, e14, e5, and e13) and two nonsense mutations (e15 and e10) (FIG. 1C-E). CrtI catalyzes the conversion of the non-colored phytoene to lycopene, which is red. All these crtI mutants were white colored colonies (FIG. 6B; FIG. 1C) similar to *C. glutamicum* ΔcrtI mutant (Heider et al., 2012) (FIG. 6C) and thus likely lacked lycopene synthesis. The six missense mutations were in highly conserved residues suggesting that they may be important for protein function (FIG. 8). The e4, e6, and e8 were missense mutations in the crtB gene, which encodes phytoene synthase (FIGS. 1D&E). All these missense mutations were in highly conserved residues suggesting that they may be important for protein function (FIG. 9). These mutants produced white bacterial colonies (FIG. 6B; FIG. 1C) as was observed in *C. glutamicum* ΔcrtB mutant (Heider et al., 2012) (FIG. 6C). Four mutations were obtained in crtEb; two nonsense mutations (e16 and e17) and two missense mutations (e3 and e19) in highly conserved residues (FIG. 1D; FIG. 10). Mutations in crtEb were likely to be defective in the conversion of lycopene to flavuxanthin (FIG. 1E). These mutants formed pale red colonies (FIG. 6; FIG. 1B) probably because of accumulation of lycopene (but not flavuxanthin) as was seen in *C. glutamicum* ΔcrtEb mutant (Heider et al., 2012) (FIG. 6C). e17 was an early stop mutation in crtEb which is predicted to produce a truncated protein of just 13 amino acids (FIG. 10). Mutations in crtYe and crtYf were defective in the last step; the homologs of these genes catalyze synthesis of decaprenoxanthin. These mutants produced pale red to orange colonies (FIG. 6B). Interestingly, the *C. glutamicum* ΔcrtY mutant accumulated flavuxanthin and also exhibited a pale orange to red color (Heider et al., 2012) (FIG. 6C).

Figure 2A:
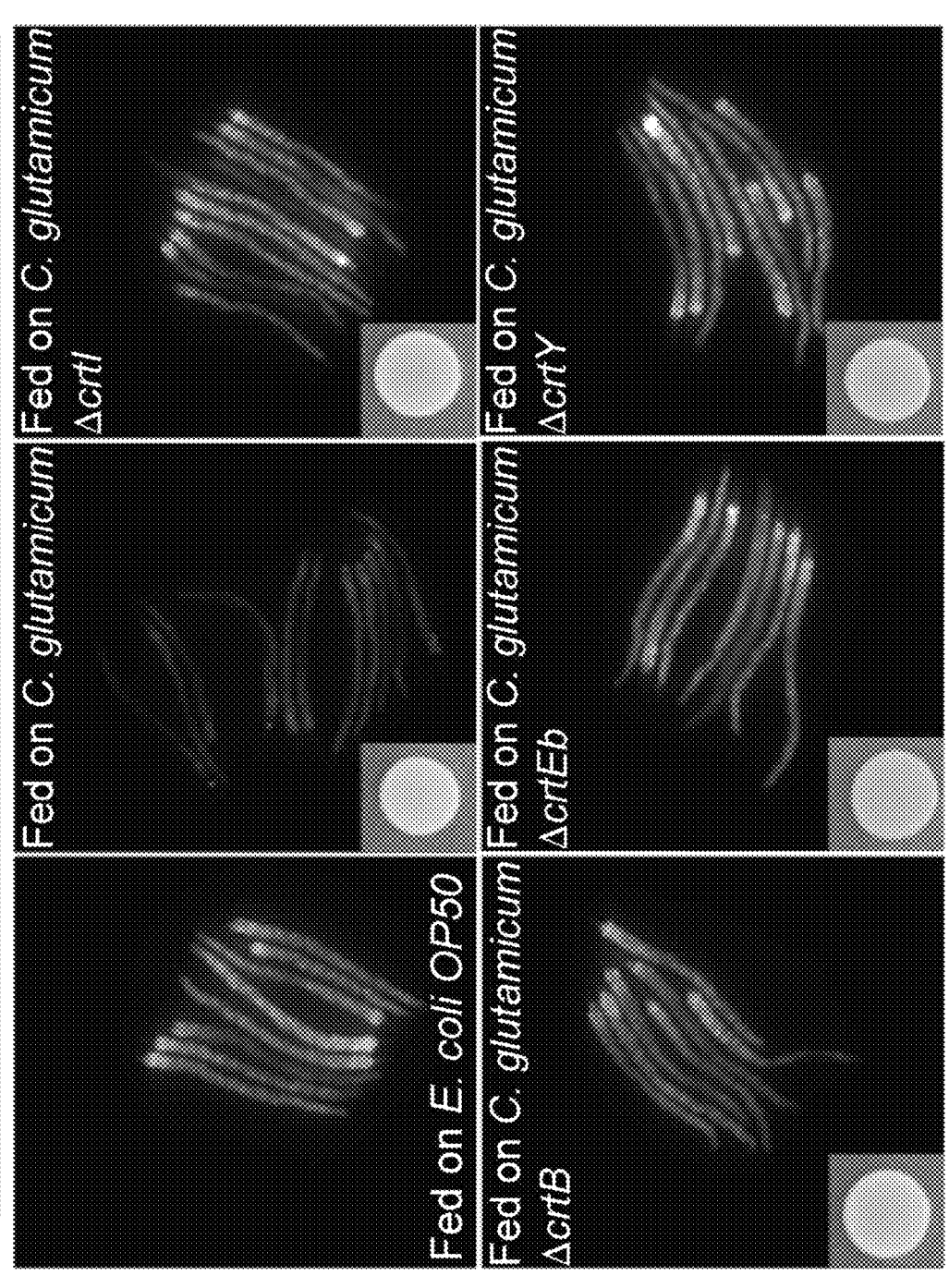
Figure 2B:
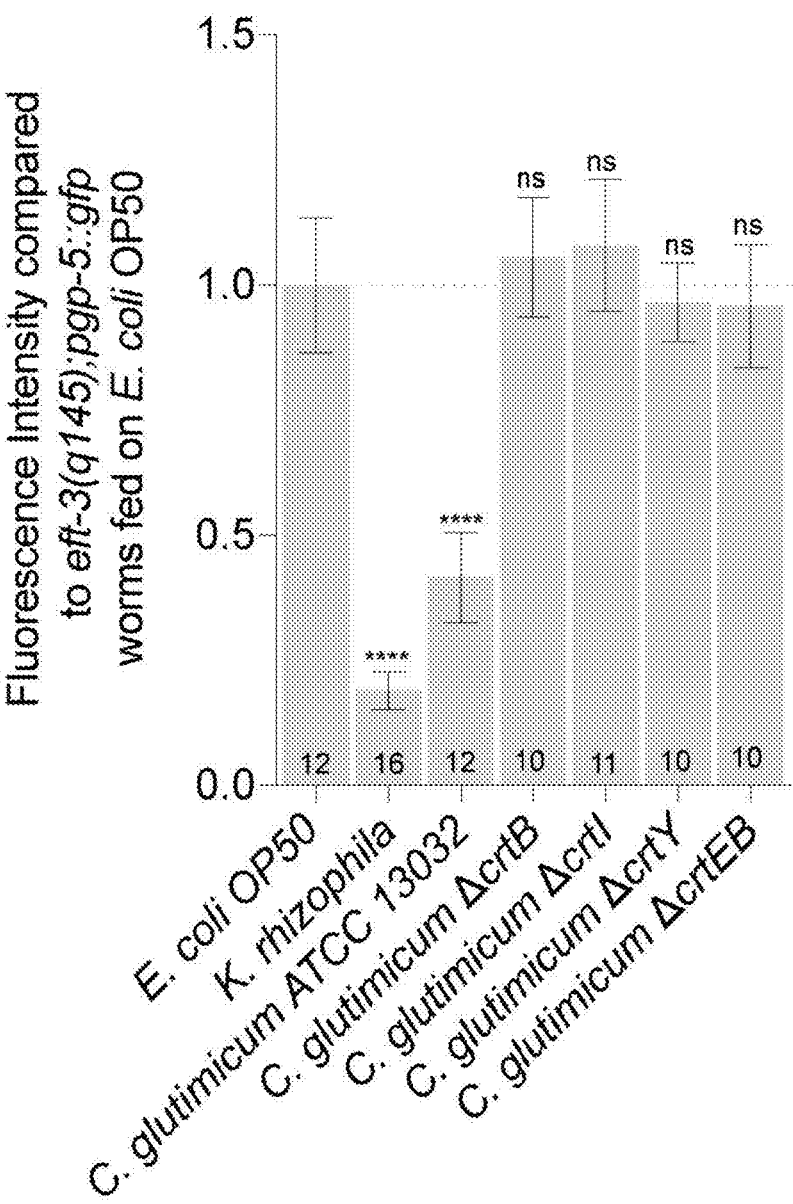

Because *C. glutamicum* ATCC13032 is known to produce decaprenoxanthin, whether feeding *C. glutamicum* ATCC13032 feeding would suppress pgp-5p::gfp induction was tested in eft-3(q145);pgp-5p::gfp animals. Feeding wild type *C. glutamicum* ATCC13032 to eft-3(q145);pgp-5p::gfp animals suppressed pgp-5p::gfp induction (FIGS. 2A&B). In *C. glutamicum* ATCC13032, the carotenoid gene cluster CrtE-cg0722-CrtBIYeYfEb mediates decaprenoxanthin biosynthesis (Heider et al., 2012). Whether *C. glutamicum* ATCC13032 deletion mutants in crtY, crtEb, crtI, and, crtB, which are known to lack decaprenoxanthin production (Heider et al., 2012), could suppress pgp-5p::gfp induction in eft-3(q145);pgp-5p::gfp animals was tested. Animals fed on ΔcrtY, ΔcrtEb, ΔcrtI, ΔcrtB *C. glutamicum* showed normal pgp-5p::gfp induction, unlike the same strain grown on wild type *C. glutamicum* (FIGS. 2A&B).

Figure 2C:
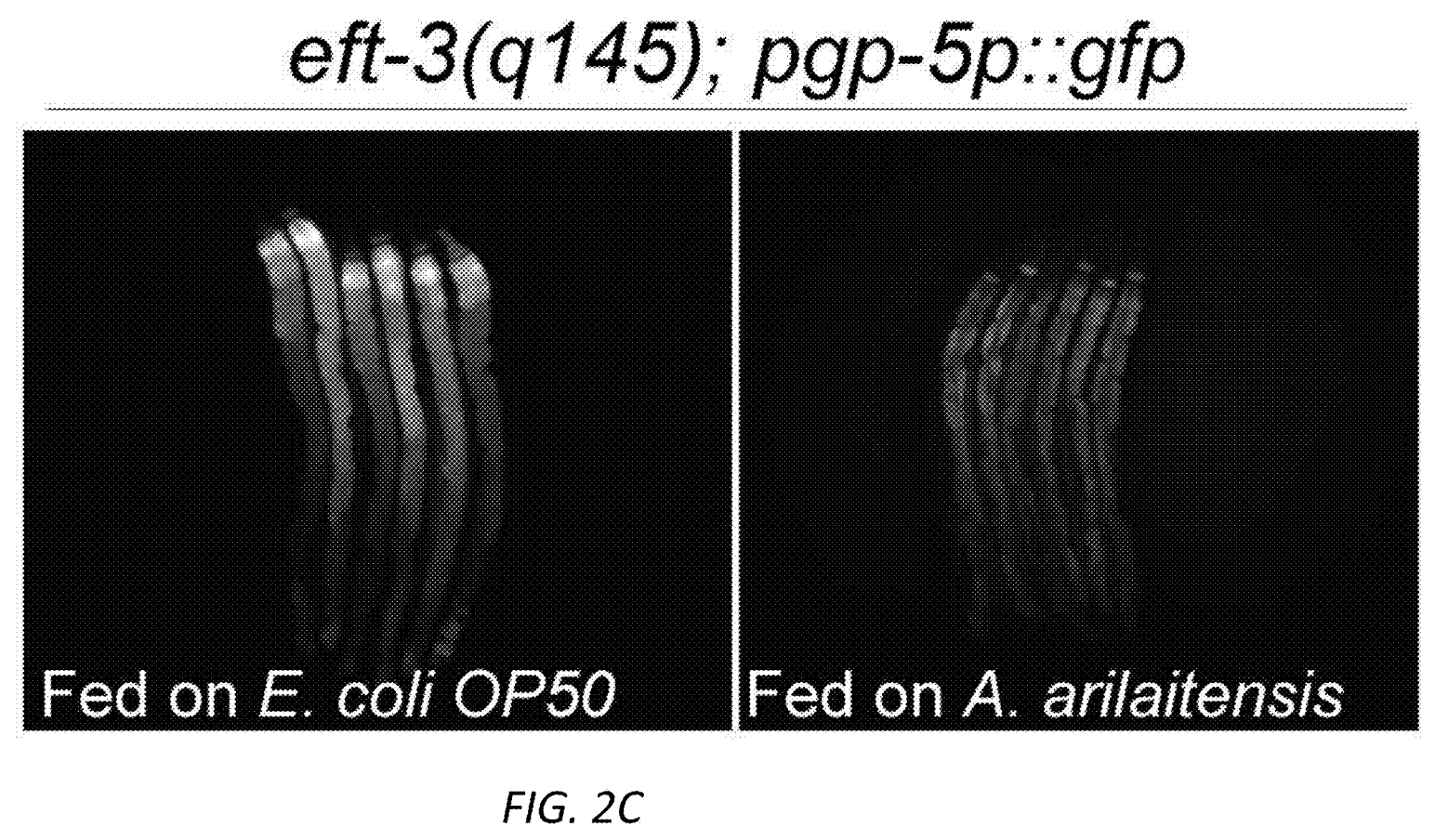

The pigmented bacterium *Arthrobacter arilaitensis* is known to produce decaprenoxanthin (Monnet et al., 2010); experiments tested whether feeding *A. arilaitensis* feeding would suppress pgp-5p::gfp induction in eft-3(q145);pgp-5p::gfp animals. Feeding *A. arilaitensis* to eft-3(q145);pgp-5p::gfp animals also suppressed pgp-5p::gfp expression (FIG. 2C). Thus, *C. glutamicum, A. arilaitensis*, or *K. rhizophila* produce a pigmented carotenoid that mediates suppression of translational surveillance to the induction of ABC transporter detoxification responses.

Figure 2D:
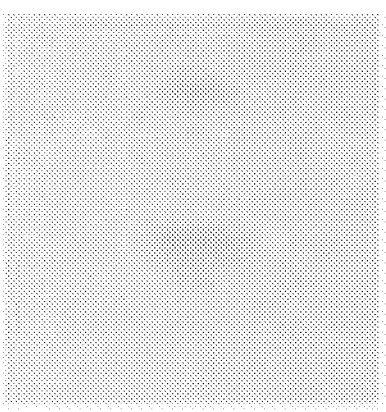
Figure 2E:
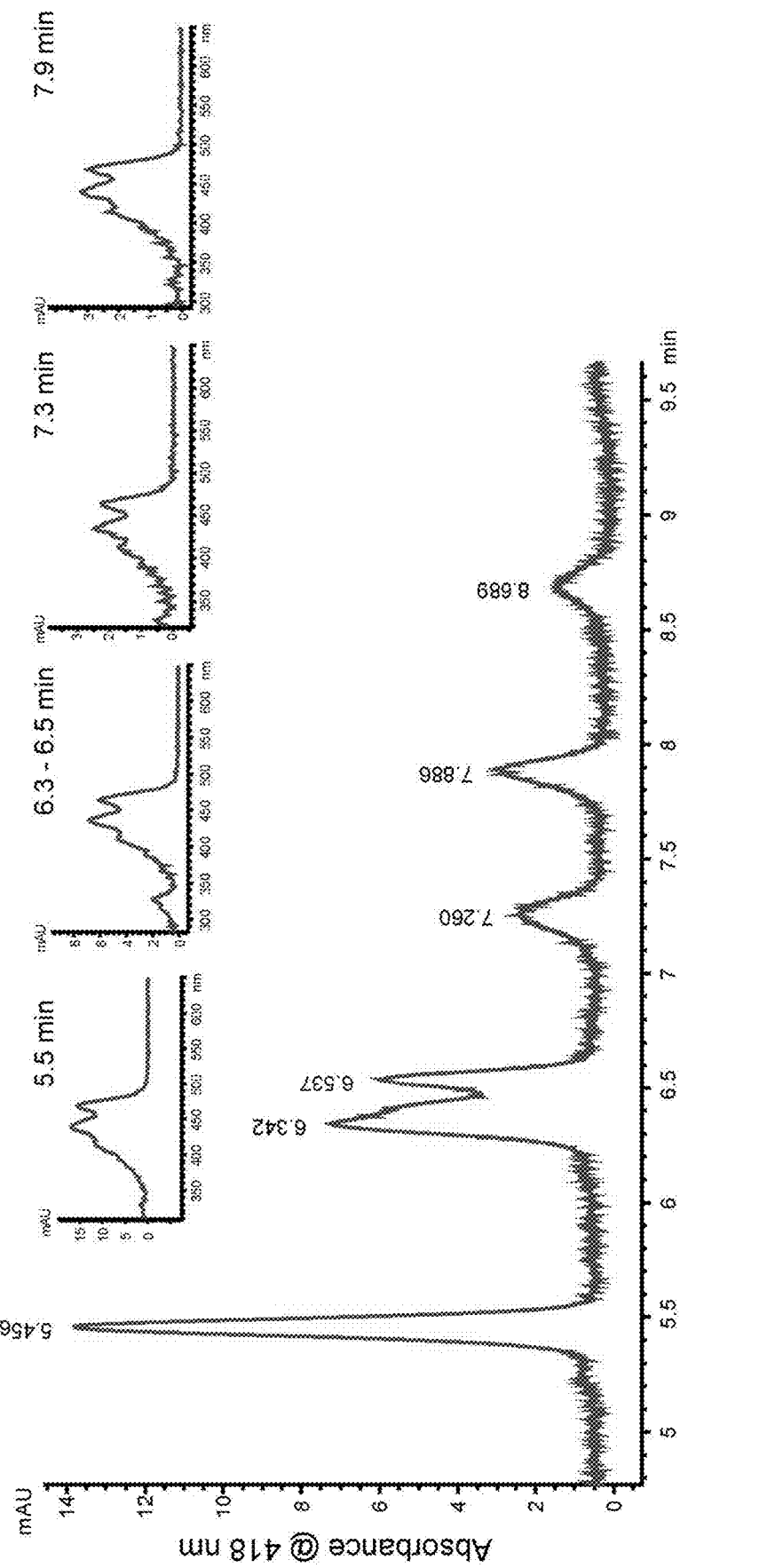
Figure 11:
Figure 11:
Figure 11:
Figure 11:
Figure 11:
Figure 11:
Figure 11:
Figure 11:
Figure 11:

Carotenoids such as decaprenoxanthin are lipophilic molecules that localize to the cell membrane and can be easily extracted in non-polar solvents. *K. rhizophila* cultures were extracted with such solvents (FIG. 11). TLC analysis of the extract revealed the presence of yellow-orange pigment (FIG. 2D). HPLC analysis of a methanol extract from *K. rhizophila* was complexed with at least six different components (FIG. 11; FIG. 2E). These peaks were named according to the time of elution times as peak 1 (5.4 min), peak 2 (6.3), peak 3 (6.5), peak 4 (7.2), peak 5 (7.8), and peak 6 (8.7) (FIG. 2E). Absorbance spectra of the elution peaks revealed absorption maxima at 420, 440 and 470 nm which is similar to the published absorption spectra of decaprenoxanthin from *Arthrobacter* (Giuffrida et al., 2016; Sutthiwong et al., 2014).

Figure 12A:
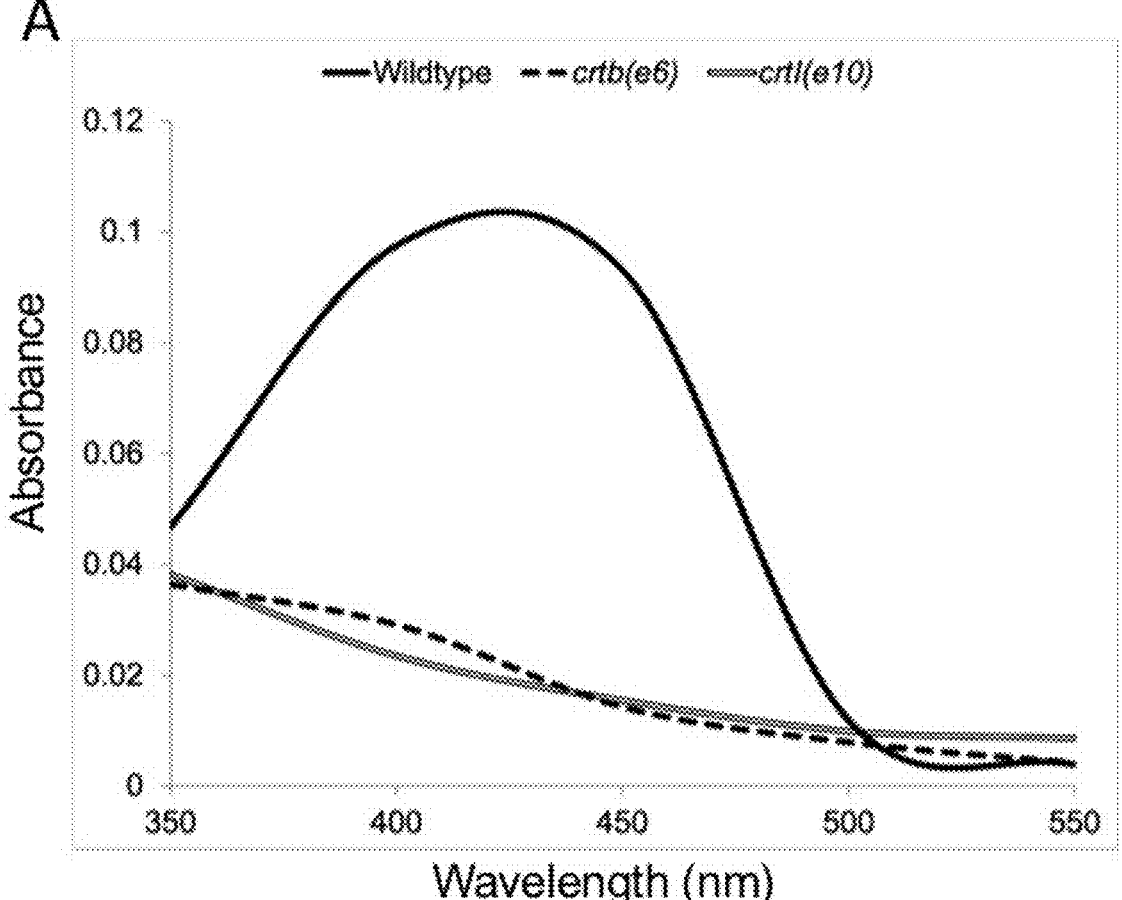
Figure 12B:
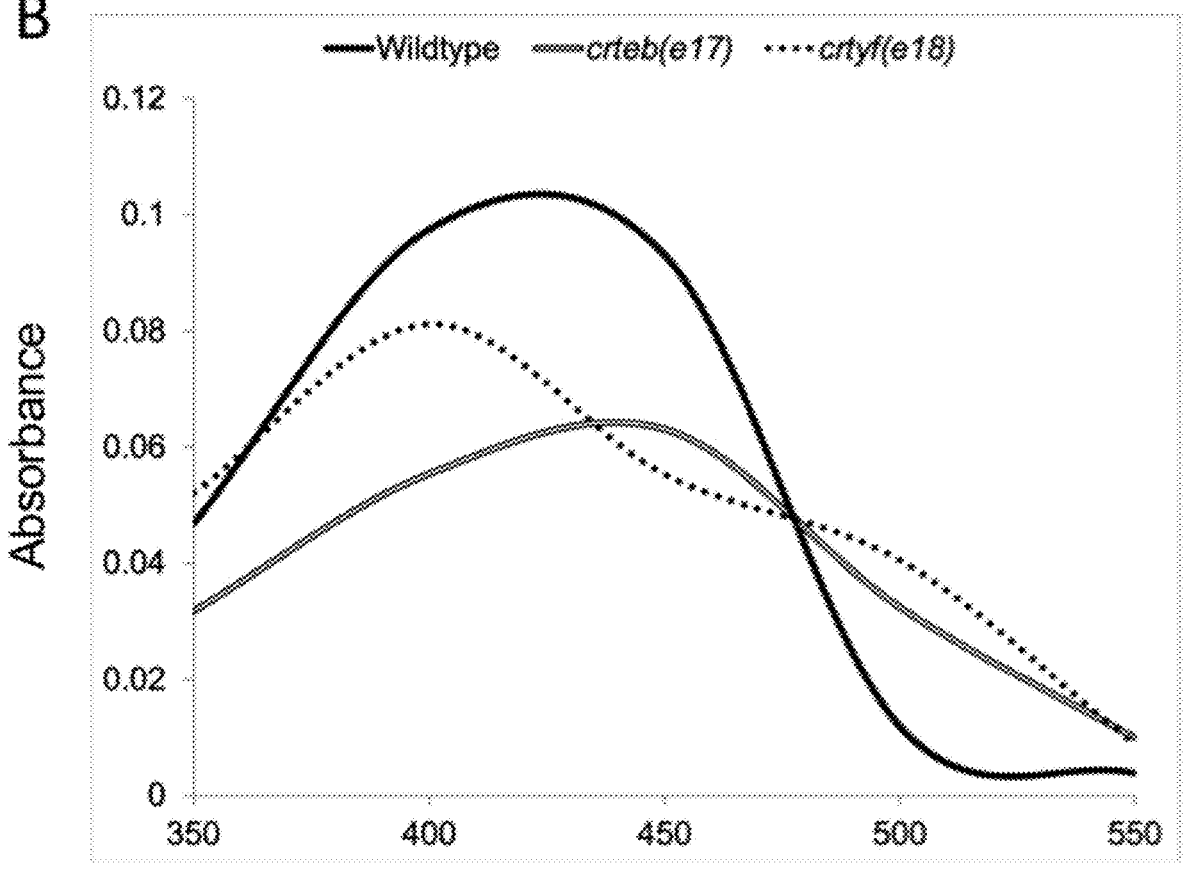
Figure 12C:
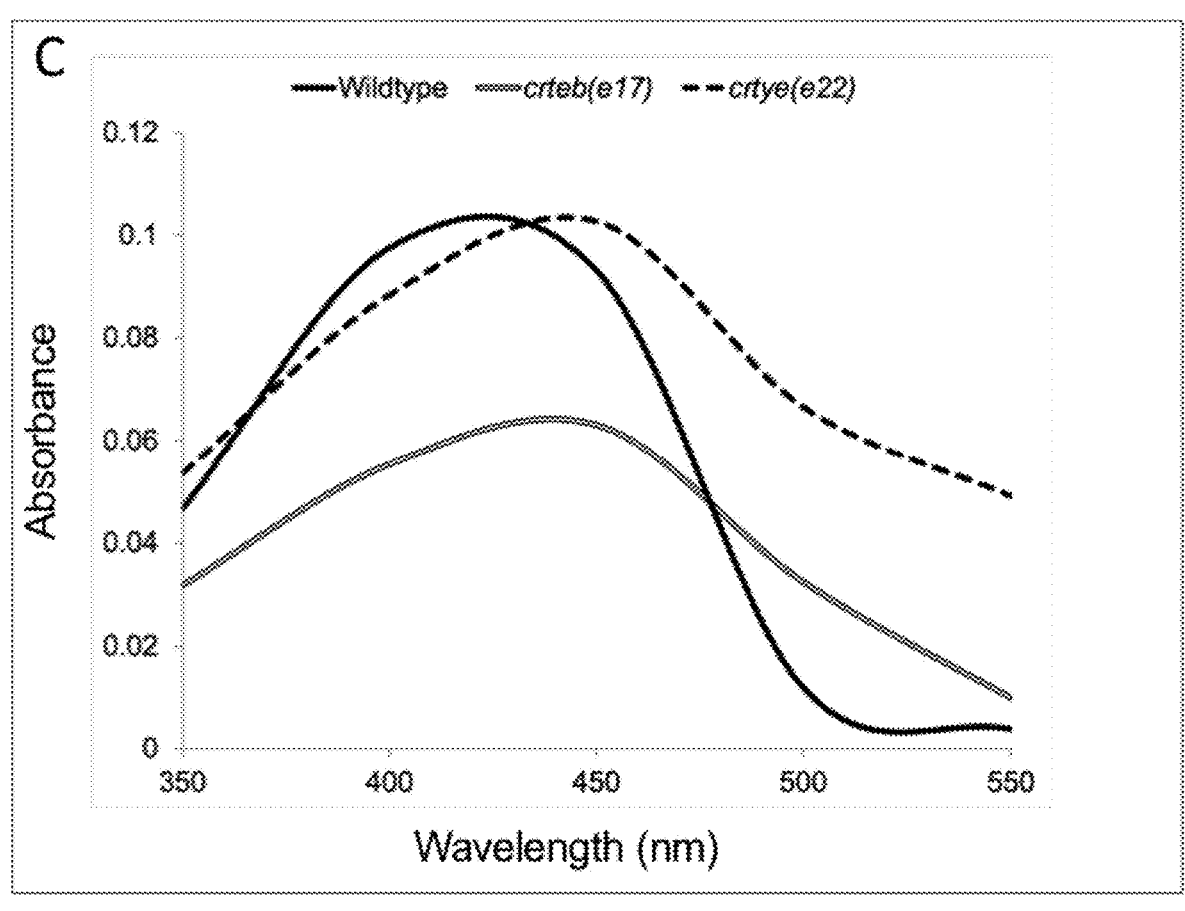

To analyze the carotenoid production in different *K. rhizophila* mutants, carotenoids were extracted from crtI (e10), crtEb(e17), crtYe(e22), and crtYf(e18), which are nonsense mutant alleles and crtB(e6) which is a missense mutant. Spectrophotometric analysis of methanol extracts from *K. rhizophila* wildtype showed absorption maxima of 415-425 nm, whereas the crtEb(e17) extract showed absorption maxima at 445-455 nm (FIG. 12). *K. rhizophila* crtEb (e17) and crtYe(e22) mutant methanol extract show similar absorption spectra while the extract from *K. rhizophila* crtI(e10) and crtb(e6) showed no absorption at all. The methanol extracts from crtYf(e18) showed two separate absorption peaks one at ~400 nm and another minor one at ~500 nm.

Figure 2F:
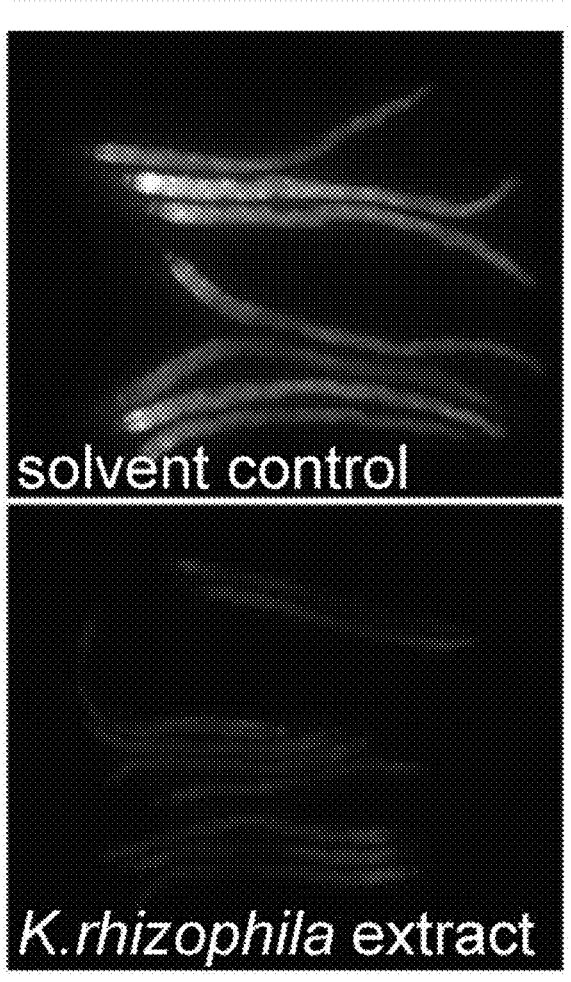
Figure 2G:
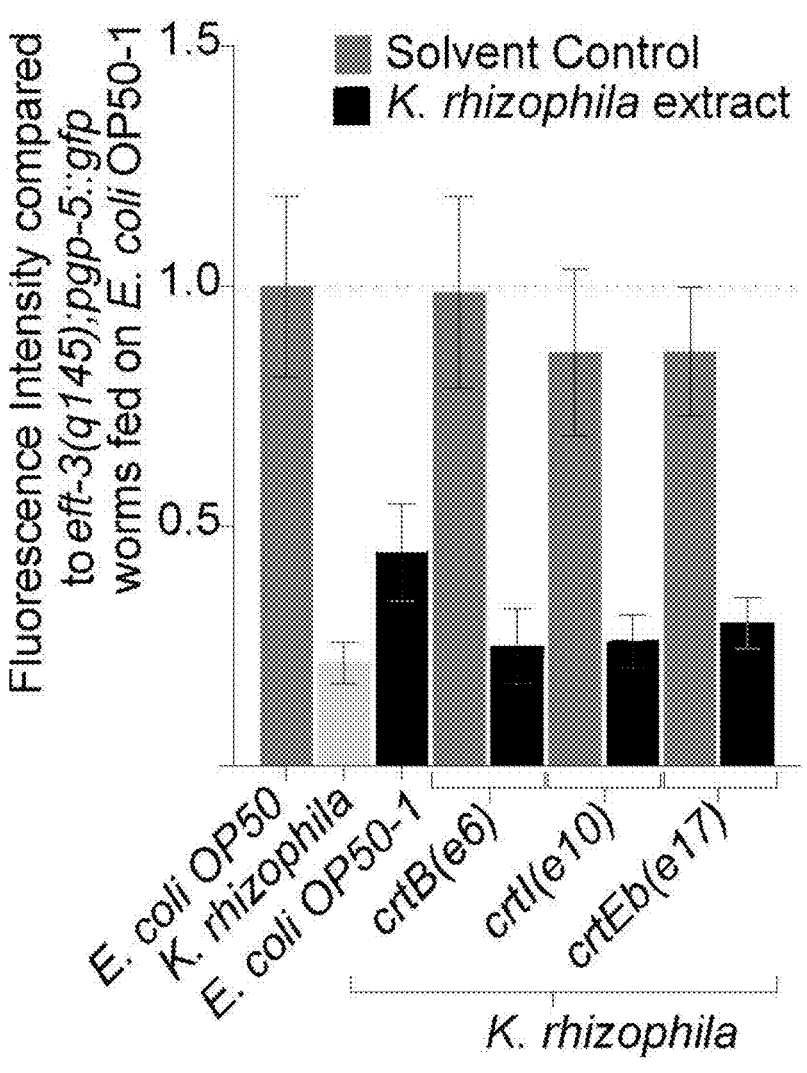

The ability of crude methanol extracts from wildtype *K. rhizophila*, containing carotenoids, to suppress the GFP induction in eft-3(q145);pgp-5p::gfp animals was also tested. Animals fed on *E. coli* with added wildtype *K. rhizophila* extract exhibited significantly reduced pgp-5p::gfp expression compared to eft-3(q145);pgp-5p::gfp animals fed on *E. coli* with control methanol extract (FIG. 2F). The extract wild type *K. rhizophila* methanol extract could rescue the suppression of *C. elegans* surveillance defect of *K. rhizophila* carotenoid biosynthetic mutants: when eft-3 (q145);pgp-5p::gfp animals were fed on *K. rhizophila* crtEb (e17), crtB(e6) or crtI(e10) mutants supplemented with *K. rhizophila* wildtype extract, GFP was not induced while in the animals fed on control extract, the GFP expression was induced by the *C. elegans* eft-3 mutation (FIG. 2G).

Figure 3A:
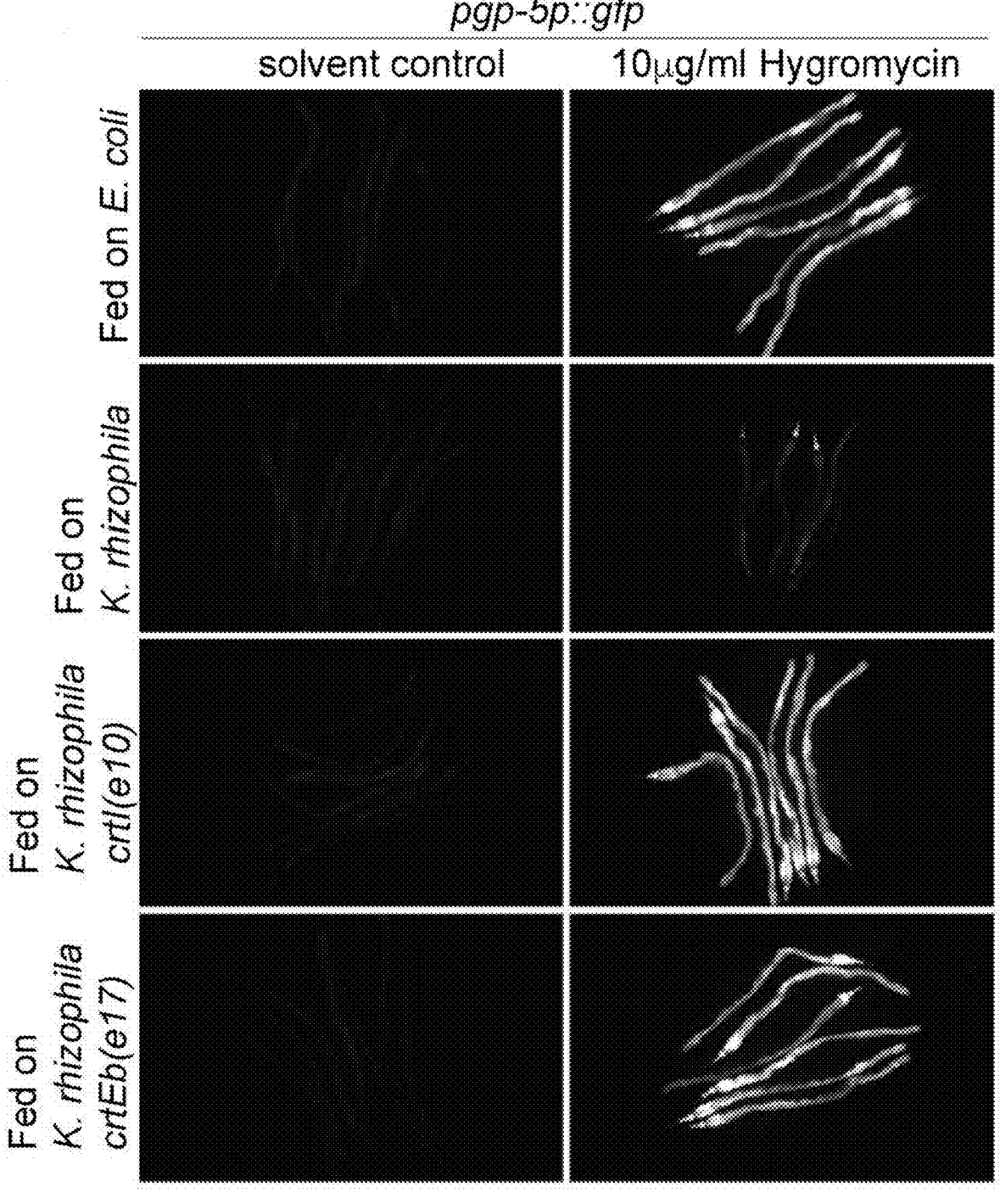
FIGS. 3A-F
A) pgp-5p::gfp induction in response to 10 mg/ml of hygromycin was significantly reduced in animals fed on *K. rhizophila* wildtype, while mutants in *K. rhizophila* crtEb(e17), or *K. rhizophila* crtI(e10) did not suppress the GFP induction.
B) Animals treated with a *K. rhizophila* carotenoid extract were hypersensitive to hygromycin. Unpaired t-test, ****$P<0.0001$ compared to the wildtype worms fed on *E. coli* OP50 containing solvent extract and hygromycin. Mean±s.d is shown. Data were collected from three independent trials of at least 20 animals for each condition. ns, was not significant compared to wildtype fed on *E. coli* OP50 containing solvent extract with no hygromycin.
C) Animals treated with a *K. rhizophila* carotenoid extract were hypersensitive to emetine.
D) Animals treated with a *K. rhizophila* carotenoid extract were hypersensitive to cisplatin.
E) Animals treated with a *K. rhizophila* carotenoid extract failed to avoid hygromycin compared animals treated with a control solvent and hygromycin.
F) Animals treated with a *K. rhizophila* carotenoid extract failed to avoid cisplatin-compared animals treated with a control solvent and cisplatin. Unpaired t-test, **$P<0.01$, $P<0.0001$. Mean±s.d is shown. ns, was not significant FIGS. 4A-E
A) pgp-5p::gfp was constitutively induced in animals fed on *E. coli* OP50 or *K. rhizophila* expressing ZIP-2:: mCherry in the intestine under the control of vha-6 promoter.
B) Supplementation of bile acids suppressed a *K. rhizophila*-induced pgp-5p::gfp activation defect in eft-3 (q145); pgp-5p::gfp animals.
C) A quantification of the suppression of a *K. rhizophila*-induced pgp-5p::gfp activation defect in eft-3(q145); pgp-5p::gfp animals by bile acids shown in FIG. 4B. Unpaired t-test, ***$P<0.0001$. Mean s.d is shown. The number of animals analyzed per condition is shown above each bar. ns, was not significant compared to eft-3(q145); pgp-5p::gfp fed on *E. coli* OP50.
D) lbp-5 RNAi, chc-1RNAi, fcho-1 RNAi, and dyn-1 RNAi suppressed a *K. rhizophila*-induced pgp-5p::gfp activation defect in eft-3(q145); pgp-5p::gfp animals while rme-1 RNAi or rab-5 RNAi did not suppress the GFP induction.
E) A working model of how *K. rhizophila* carotenoid extract may suppress the induction of xenobiotic detoxification response.
Figure 13A:
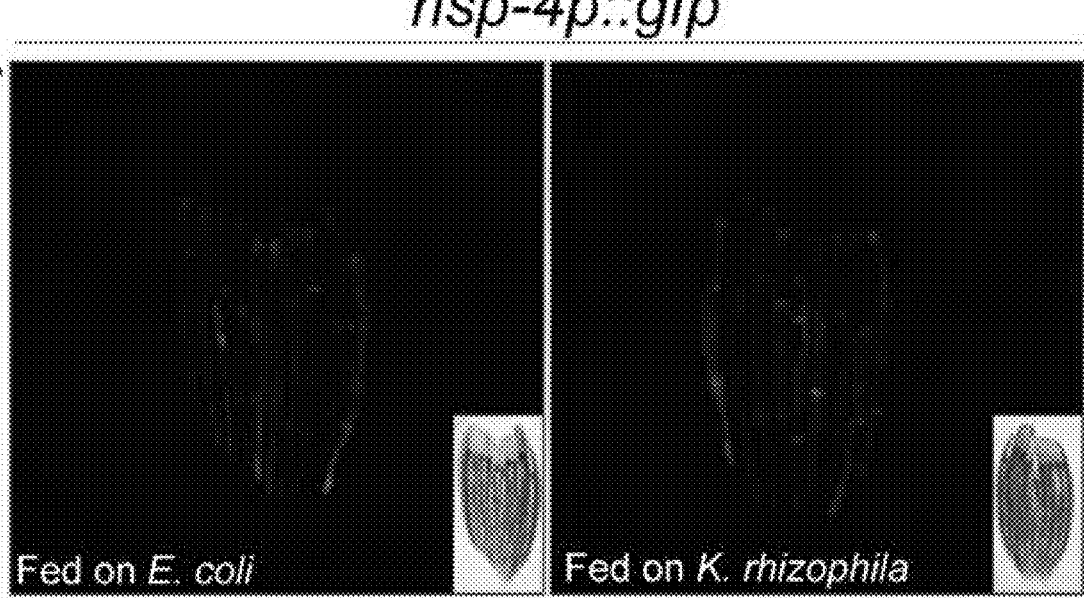
Figure 13B:
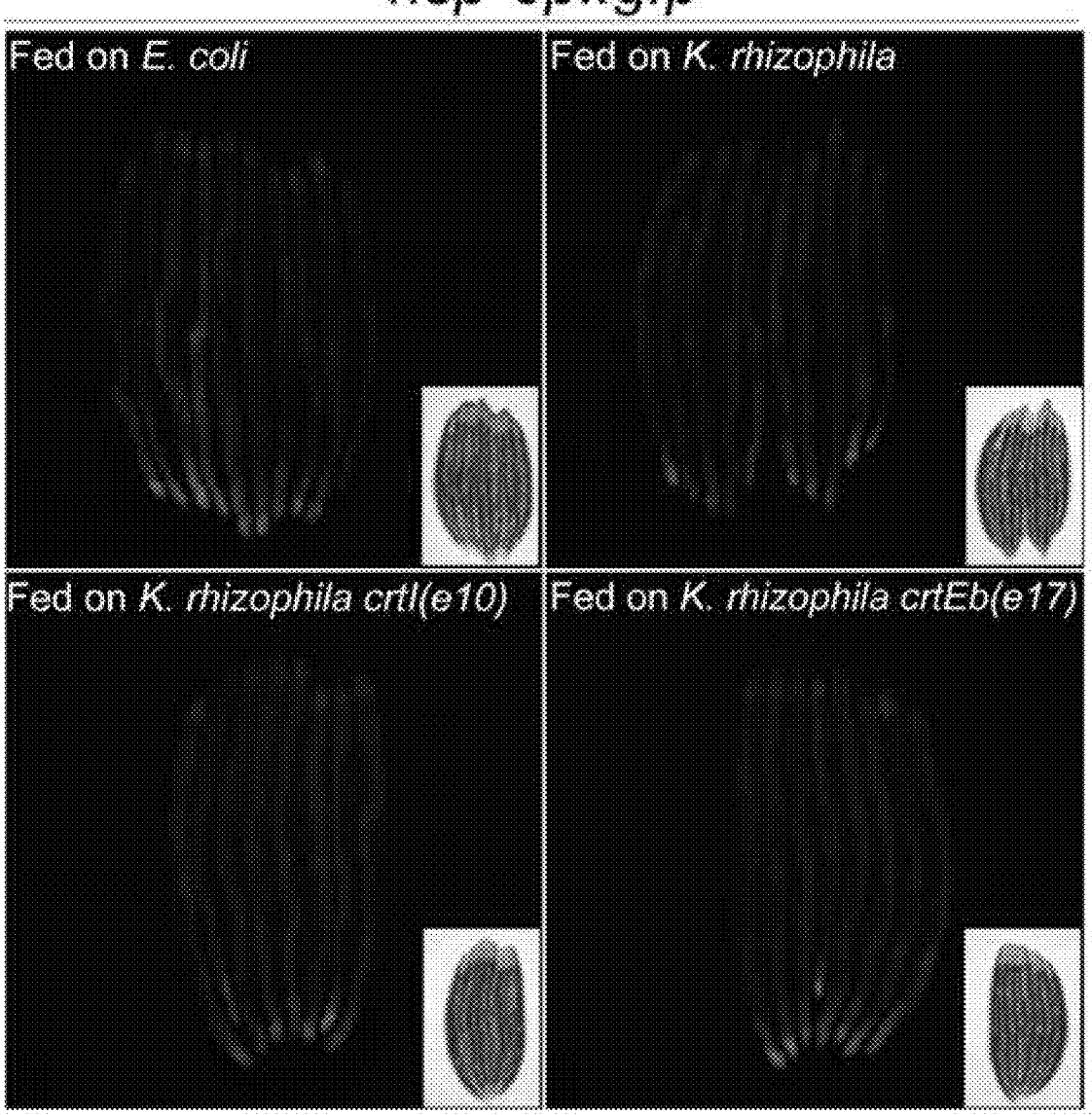
Figure 13C:
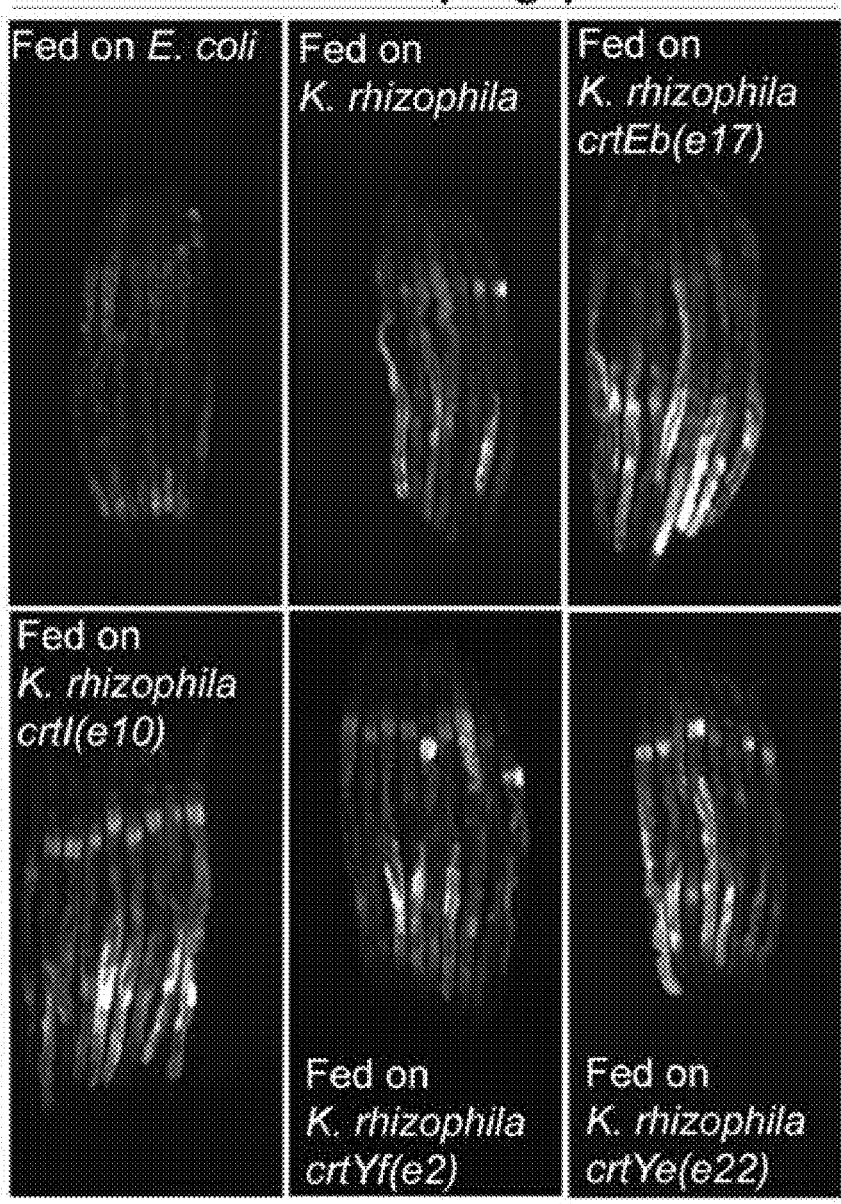
Figure 13D:
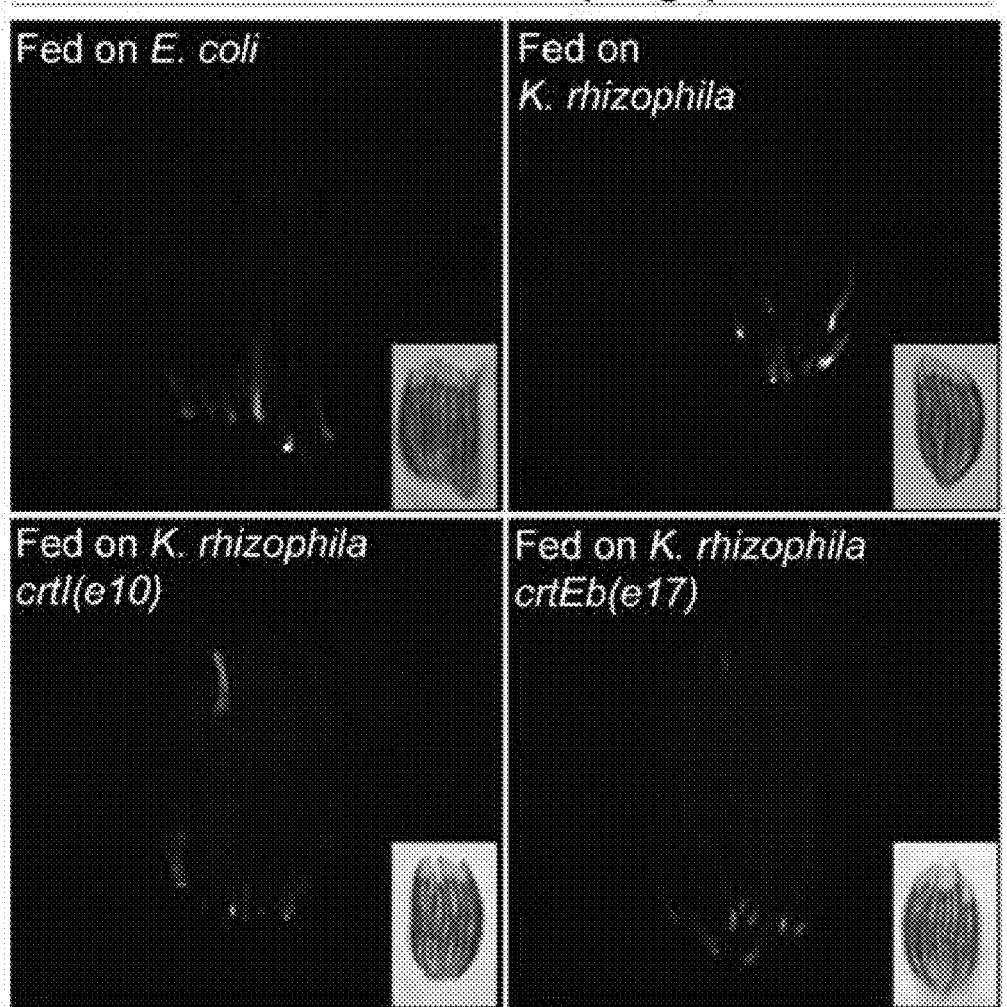

One trivial explanation for the failure of the *K. rhizophila* carotenoid mutants to suppress pgp-5p::gfp in a translation-defective *C. elegans* mutant would be that these *K. rhizophila* pigmentation mutants might induce pgp-5p::gfp even in a wildtype *C. elegans* background. To test this possibility, wild type *C. elegans* carrying the pgp-5p::gfp fusion gene were fed on *K. rhizophila* crtEb(e17), crtYe(e22), crtYf (e18), crtB(e6) or crtI(e10) mutants. The results showed that *K. rhizophila* wildtype and carotenoid mutants did not induce pgp-5p::gfp (FIG. 3A). Another possible interpretation was that *K. rhizophila* feeding might induce other stress responses in *C. elegans* that somehow "distract" the animal from surveillance of translation. The effects of induction of other GFP fusion reporters of stress was tested in wild type and various *K. rhizophila* mutants. hsp-4p::gfp and hsp-6p:: gfp are reporters of endoplasmic reticulum unfolded protein response (UPR$^{ER}$) and mitochondrial unfolded protein response (UPR$^{mito}$) respectively (Yoneda et al., 2004; Calfon et al., 2002). clec-60 is a C-type lectin/CUB domain protein induced by the gram-positive pathogens, *S. aureus* and *M. nematophilum* (O'Rourke et al., 2006). F35E12.5p:: GFP is a CUB domain protein induced by *Y. pestis, M. nematophilum* and *P. aeruginosa* (O'Rourke et al., 2006; Troemel et al., 2006; Bolz et al., 2010). *C. elegans* hsp-4p:: gfp, hsp-6p::gfp, F35E12.5p::GFP, and clec-60p::gfp were fed on *K. rhizophila* wildtype and carotenoid mutants. The *K. rhizophila* did not induce hsp-4p::gfp expression (FIG. 13A). Similarly, *K. rhizophila* wildtype or carotenoid mutant did not induce hsp-6p::gfp expression (FIG. 13B). *K. rhizophila* wildtype or carotenoid mutants does not induce F35E12.5p::GFP (FIG. 13D). But *K. rhizophila* wildtype or carotenoid mutants induced clec-60::GFP (FIG. 13C), which is induced by gram positive bacteria. Because *K. rhizophila* is also a gram-positive bacterium, the induction of clec-60 is most likely an immune response to a pathogen.

Figure 13E:
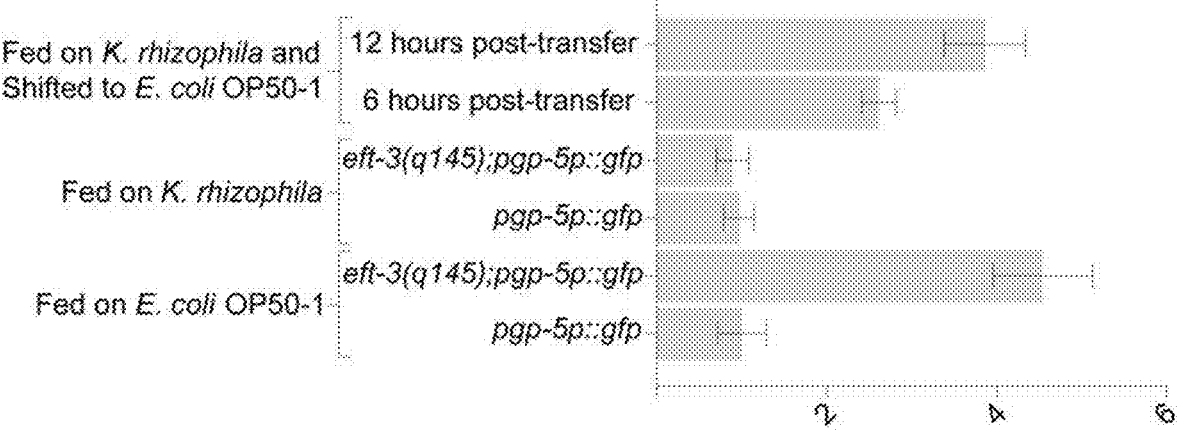

To address whether the effect of *K. rhizophila* feeding on the suppression of pgp-5p::gfp induction is reversible, eft-3(q145);pgp-5p::gfp animals fed on *K. rhizophila* were transferred after various times to *E. coli* OP50 plates. GFP expression was restored within 12 hours of transfer (FIG. 13E).

Figure 14A:
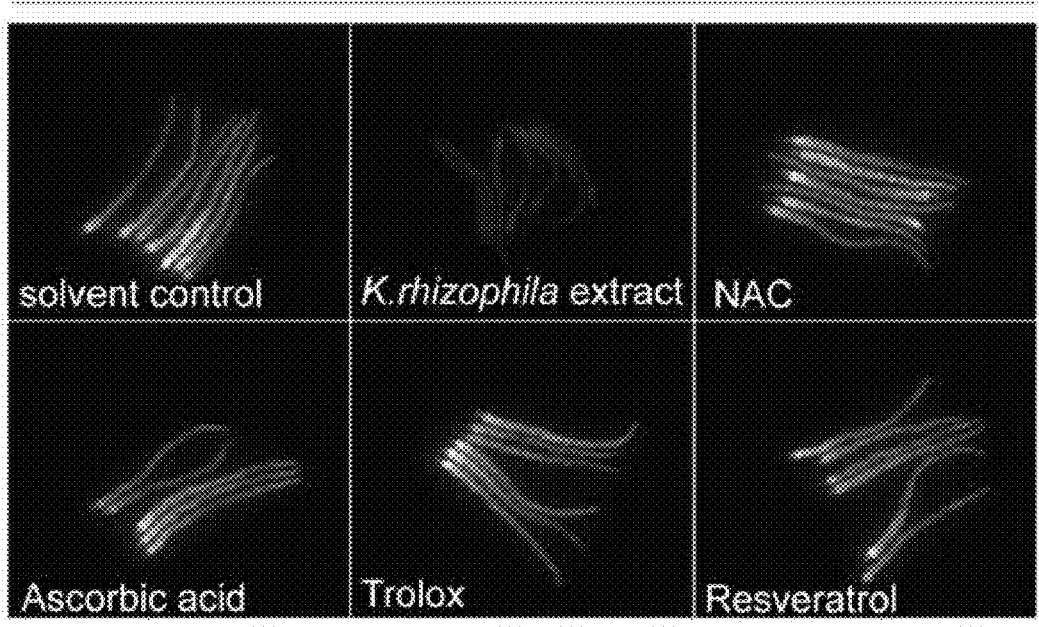
Figure 14B:
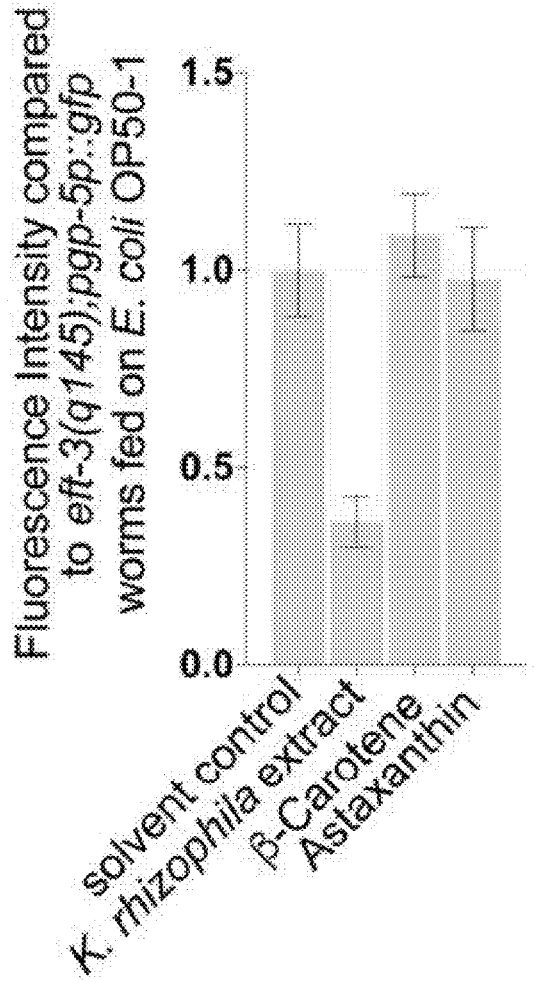
Figure 14C:
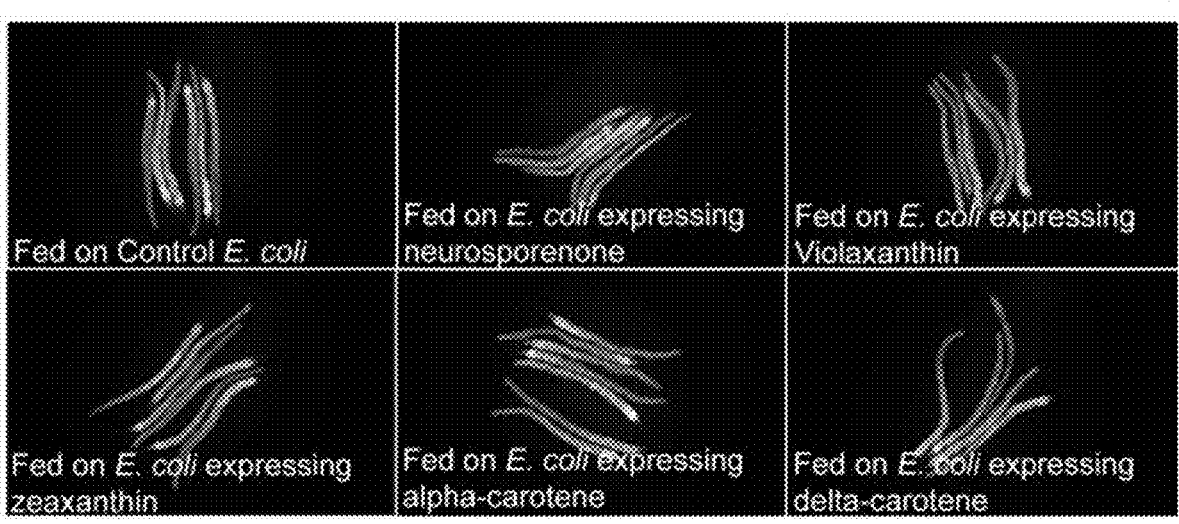

Because C50 carotenoids have multiple conjugated double bonds, they are likely to have antioxidant activity (Edge et al., 1997). However, it is unlikely that the ROS-quenching property of carotenoids is responsible for the suppression of pgp-5p::gfp induction for several reasons. First, pgp-5p::gfp is not induced by oxidative stress (Govindan et al., 2015). Second, whether known antioxidants can suppress the induction of pgp-5p::gfp was tested in a *C. elegans* translation defective mutant. eft-3(q145);pgp-5p:: gfp animals grown on *E. coli* OP50 were treated with either N-acetyl cysteine, ascorbic acid, trolox or resveratrol and screened after 50 hours at 20° C. The induction of pgp-5p:: gfp was not significantly different in animals treated with antioxidants compared to mock-treated eft-3(q145);pgp-5p:: gfp animals (FIG. 14A). Third, commercially available carotenoids were tested for the ability to suppress the induction of pgp-5p::gfp in a *C. elegans* translation defective mutant. eft-3(q145);pgp-5p::gfp animals grown on *E. coli* OP50 were treated with either beta-carotene or astaxanthin and screened after 50 hours at 20° C. The induction of pgp-5p::gfp was not significantly different in animals fed on these antioxidants compared to mock-treated eft-3(q145); pgp-5p::gfp animals (FIG. 14B). Finally, eft-3(q145);pgp-5p::gfp animals were fed on *E. coli* expressing either zeaxanthin, neurosporene, violaxanthin, delta-carotene, or alpha-carotene and screened for GFP induction. The induction of pgp-5p::gfp was not significantly different in animals fed on *E. coli* expressing carotenoids compared to mock-treated eft-3(q145);pgp-5p::gfp animals (FIG. 14C). None of these carotenoids are C50 class carotenoids.

Figure 14D:
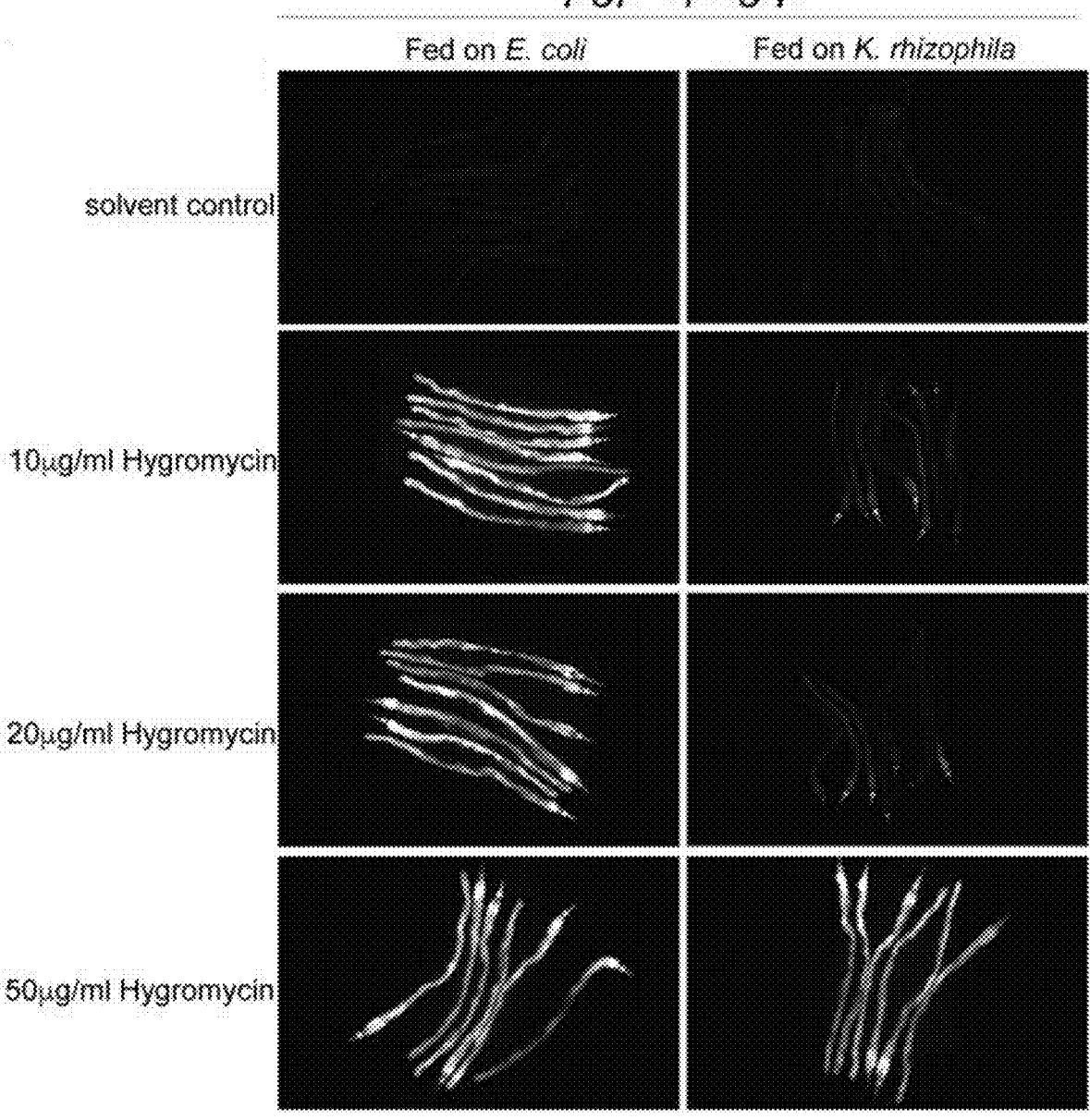
Figure 15A:
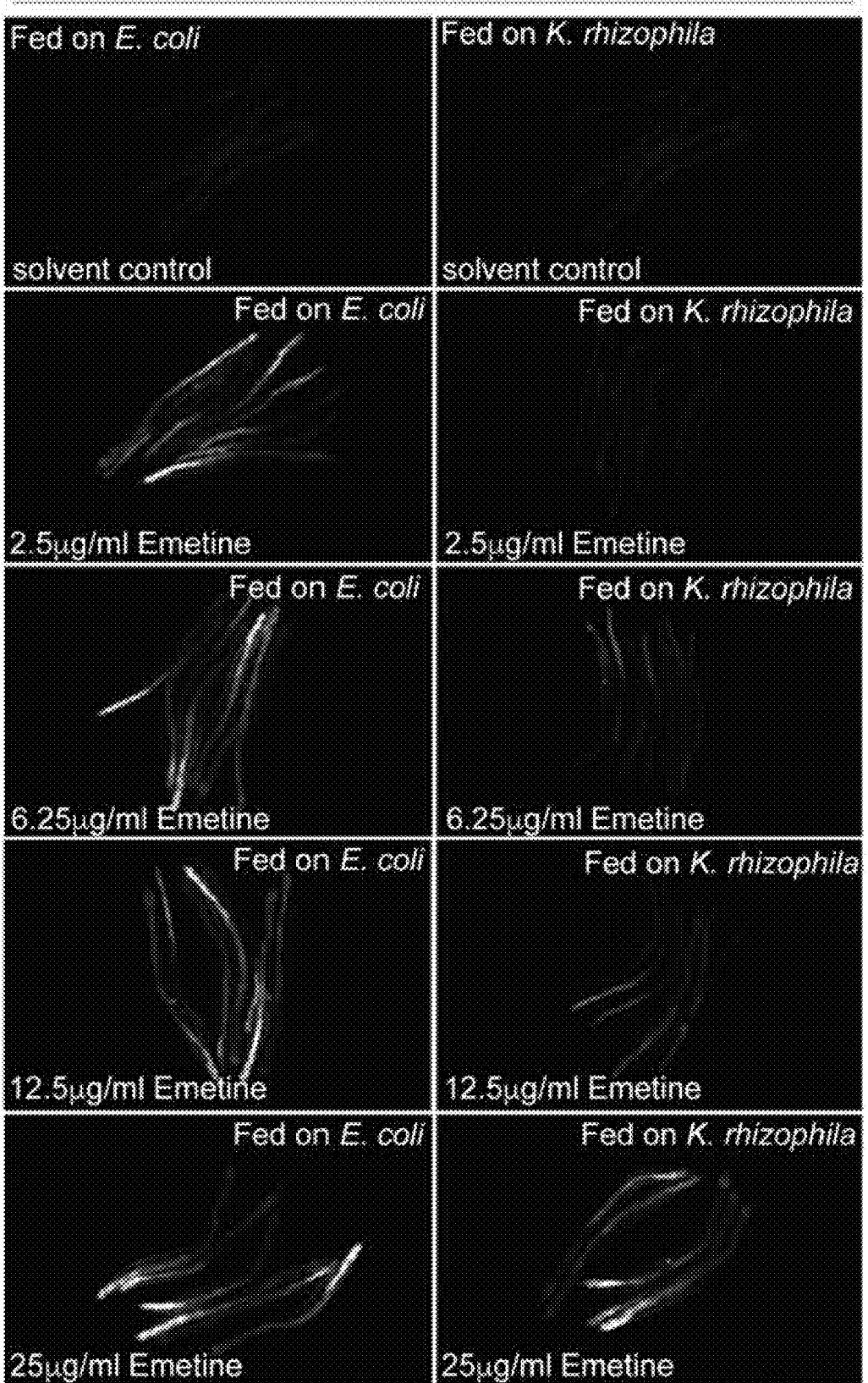
Figure 15B:
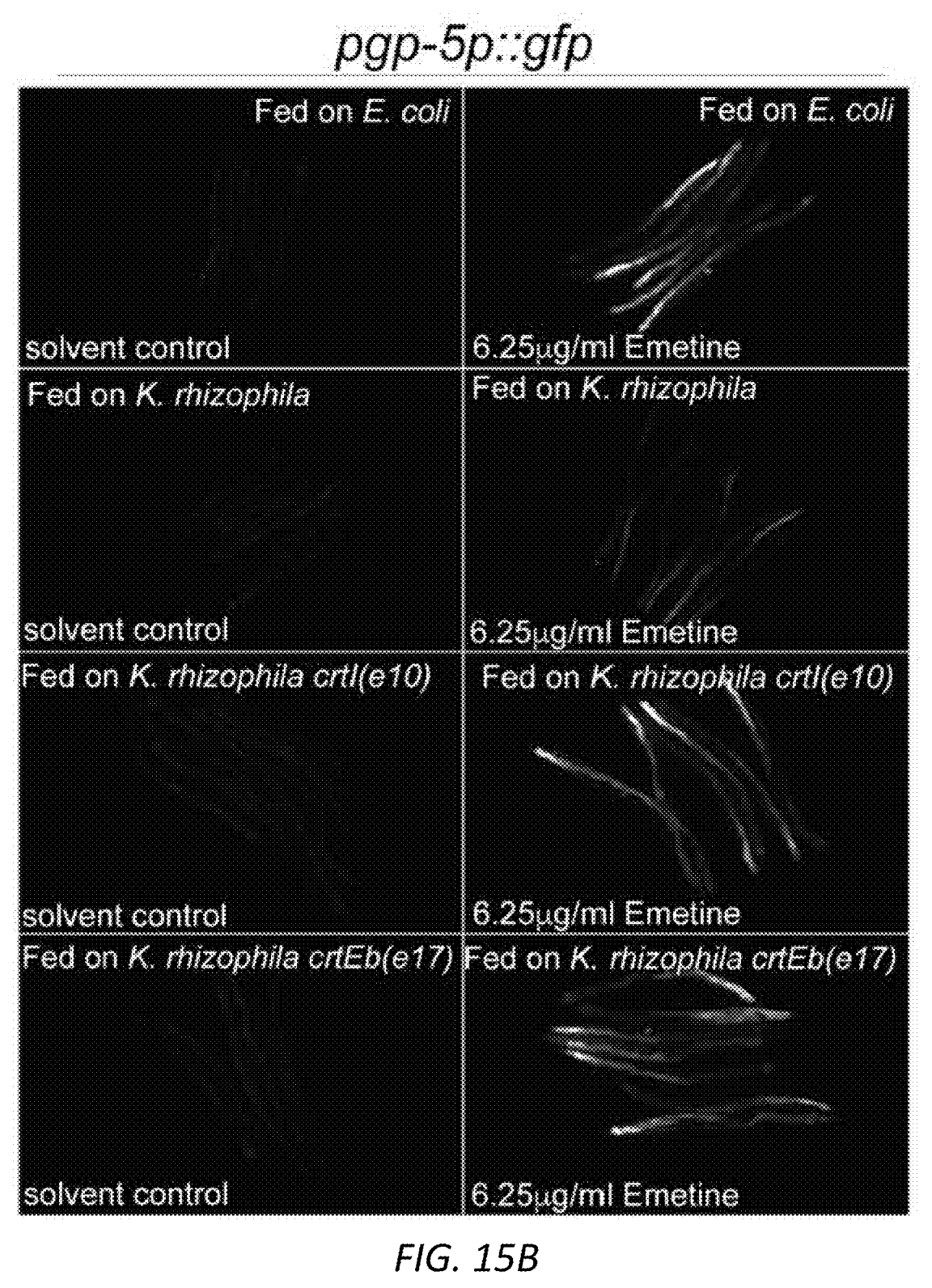
Figure 15C:
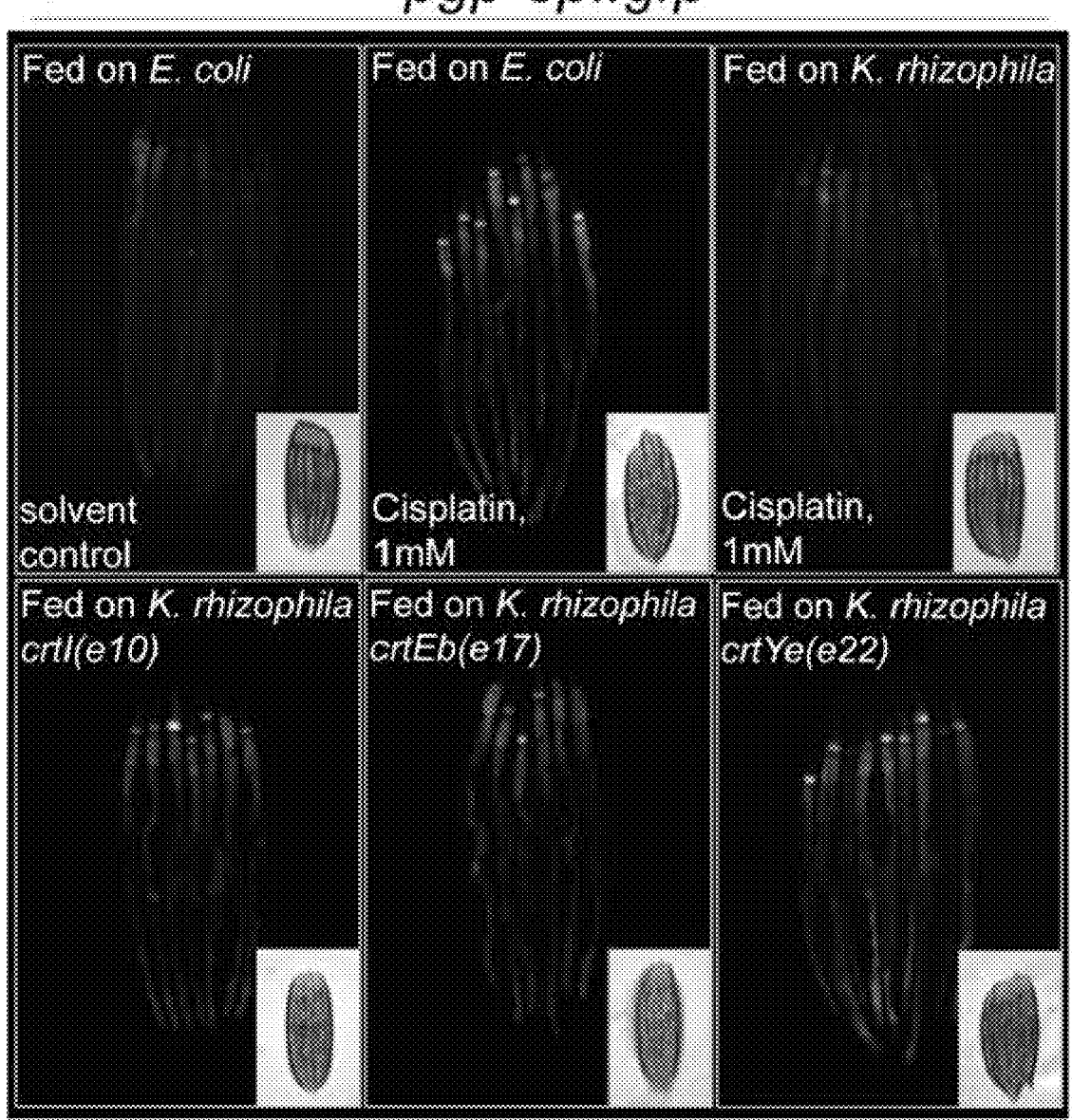

*K. rhizophila* also suppresses the detoxification response to translation inhibiting drugs. Hygromycin is a bacterially-produced antibiotic (from *Streptomyces hygroscopicus*) that inhibits translation and induces xenobiotic detoxification in *C. elegans*. While 10 µg/ml of hygromycin induces pgp-5p:: gfp expression in animals fed *E. coli* OP50, animals fed *K. rhizophila* and 10 µg/ml of hygromycin failed to induce pgp-5p::gfp (FIG. 3A; FIG. 14D). However, at high concentrations of hygromycin, pgp-5p::gfp is induced both in animals fed on *E. coli* OP50 and *K. rhizophila* (FIG. 14D). By contrast, pgp-5p::gfp animals fed on *K. rhizophila* crtI (e10) or crtEb(e17) did not affect the GFP induction in response to hygromycin treatment (FIG. 3A). Similar results were obtained with emetine which blocks protein synthesis by binding to the 40S subunit of the ribosome. 6.25 µg/ml of emetine induces pgp-5p::gfp expression in animals fed *E. coli* OP50 (FIGS. 15A&B); however, animals fed *K. rhizophila* and 6.25 µg/ml of emetine fail to induce pgp-5p::gfp. However, at high concentrations of emetine, pgp-5p::gfp is induced both in animals fed *E. coli* OP50 and *K. rhizophila* (FIG. 15A). By contrast, pgp-5p::gfp animals fed *K. rhizophila* crtI(e10) or crtEb(e17) did not affect the GFP induction in response to emetine treatment (FIG. 15B). pgp-5p:: gfp was activated in response to genotoxic stress induced by cisplatin, which interferes with DNA replication. While 1 mM cisplatin induces pgp-5p::gfp expression in animals fed *E. coli* OP50, animals fed *K. rhizophila* and 1 mM cisplatin fail to induce pgp-5p::gfp (FIG. 15C). By contrast, pgp-5p:: gfp animals fed *K. rhizophila* crtI(e10), crtEb(e17), or crtYe(e22) did not affect the GFP induction in response to cisplatin treatment (FIG. 15C).

Figure 3B:
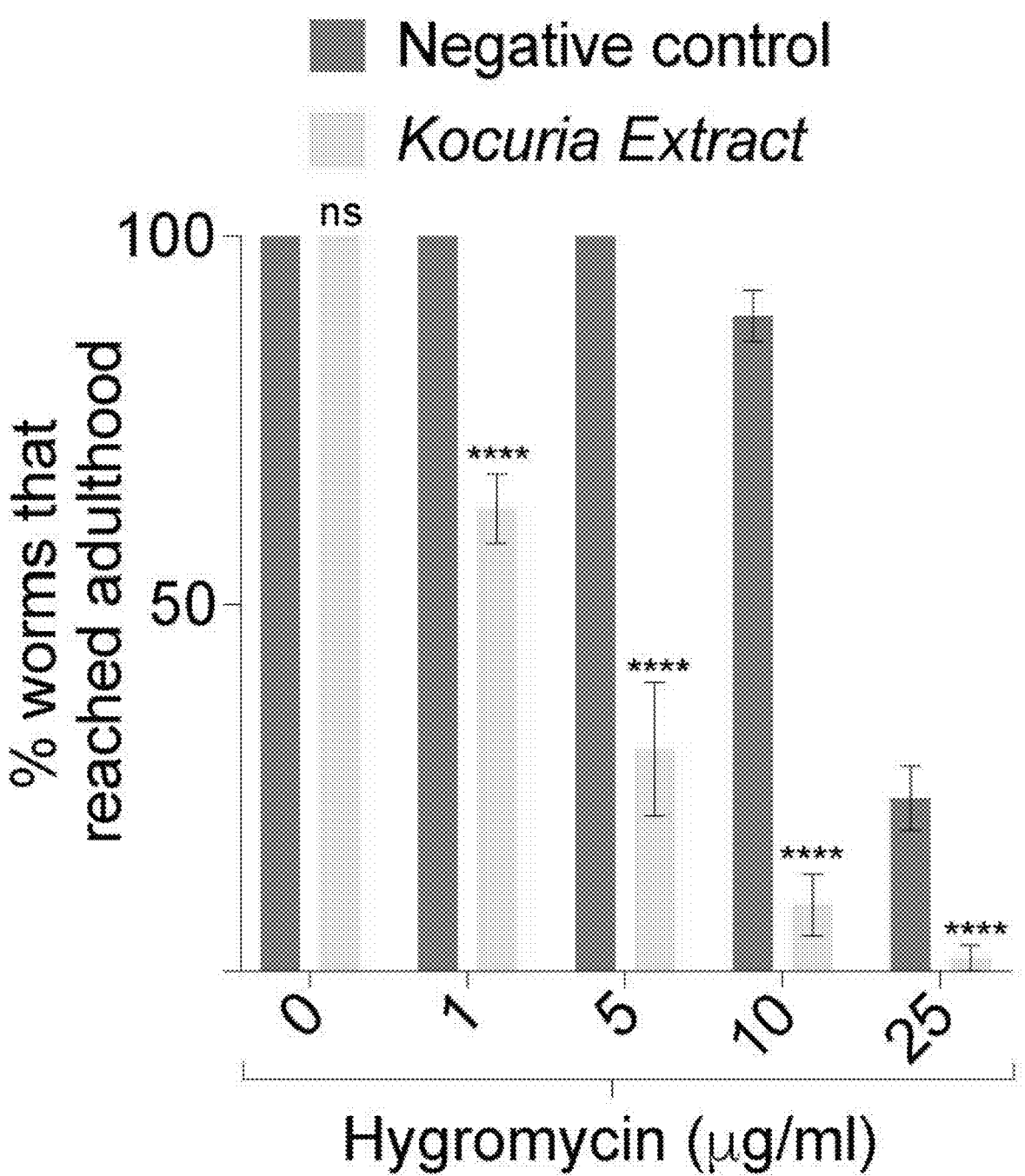
Figure 3C:
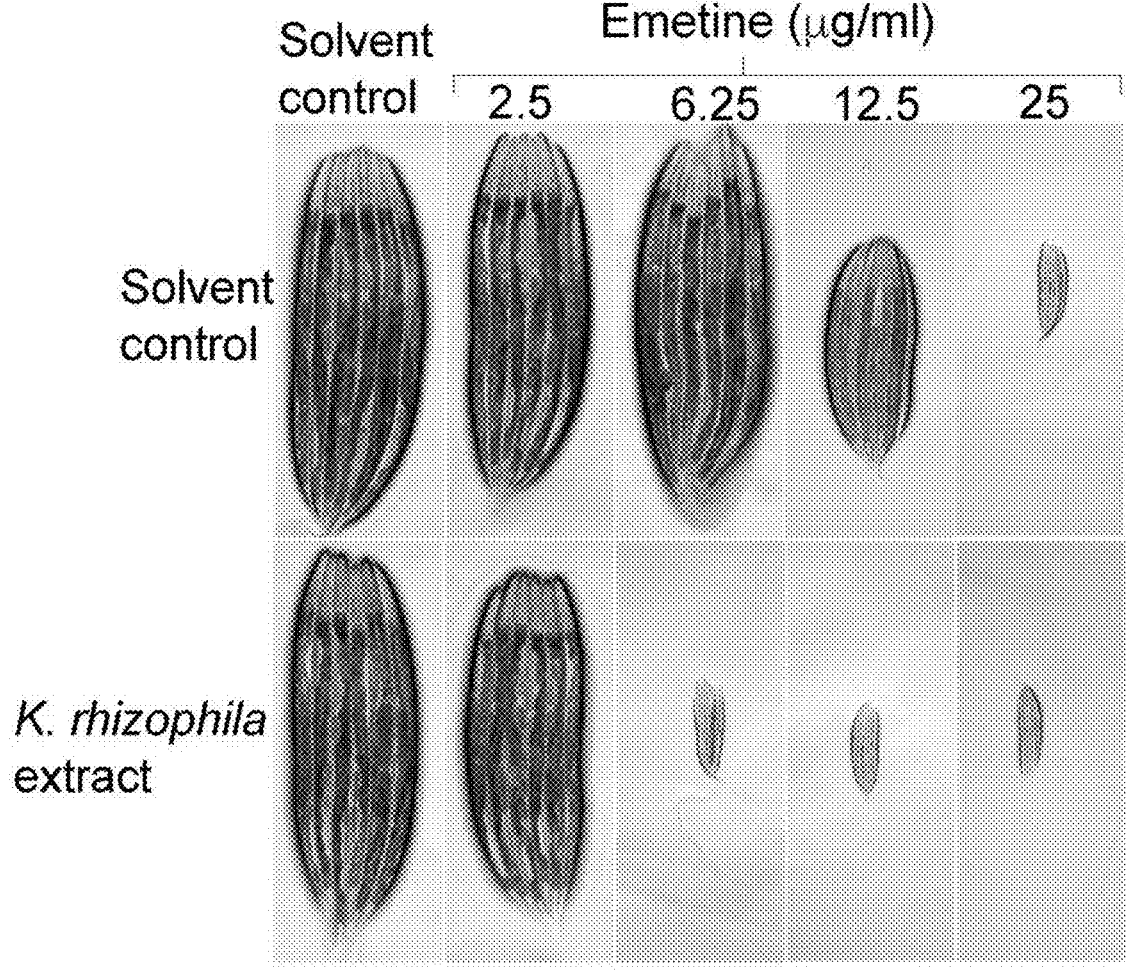
Figure 3D:
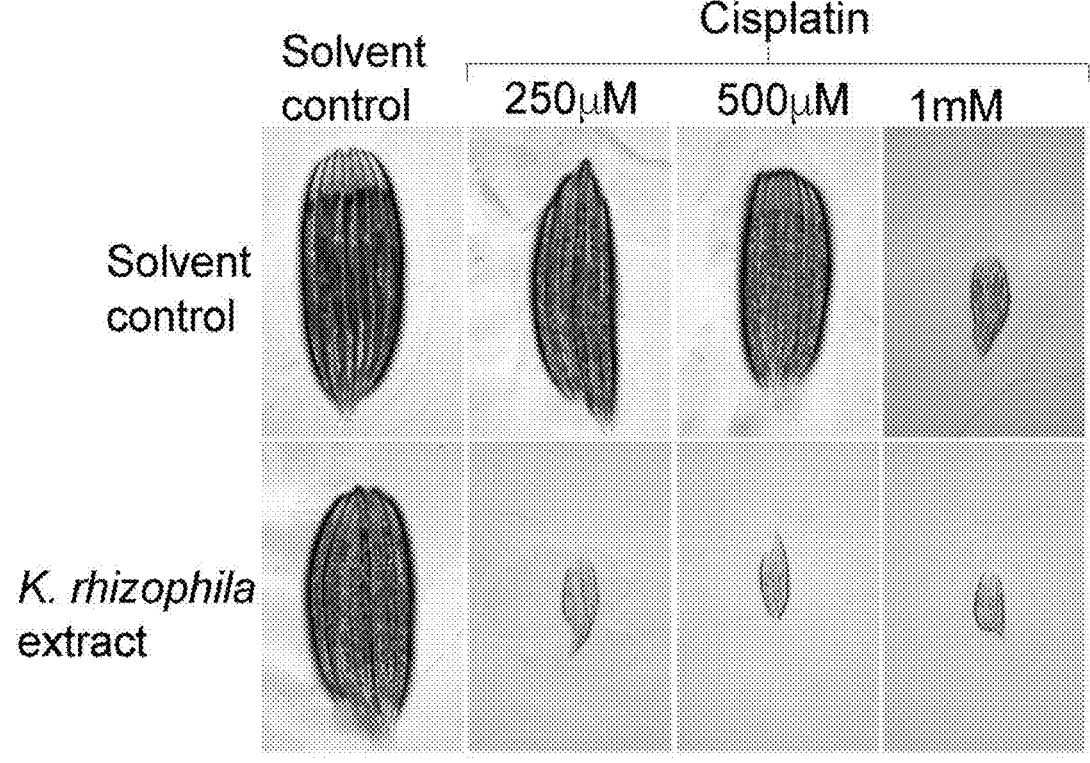
Figure 15D:
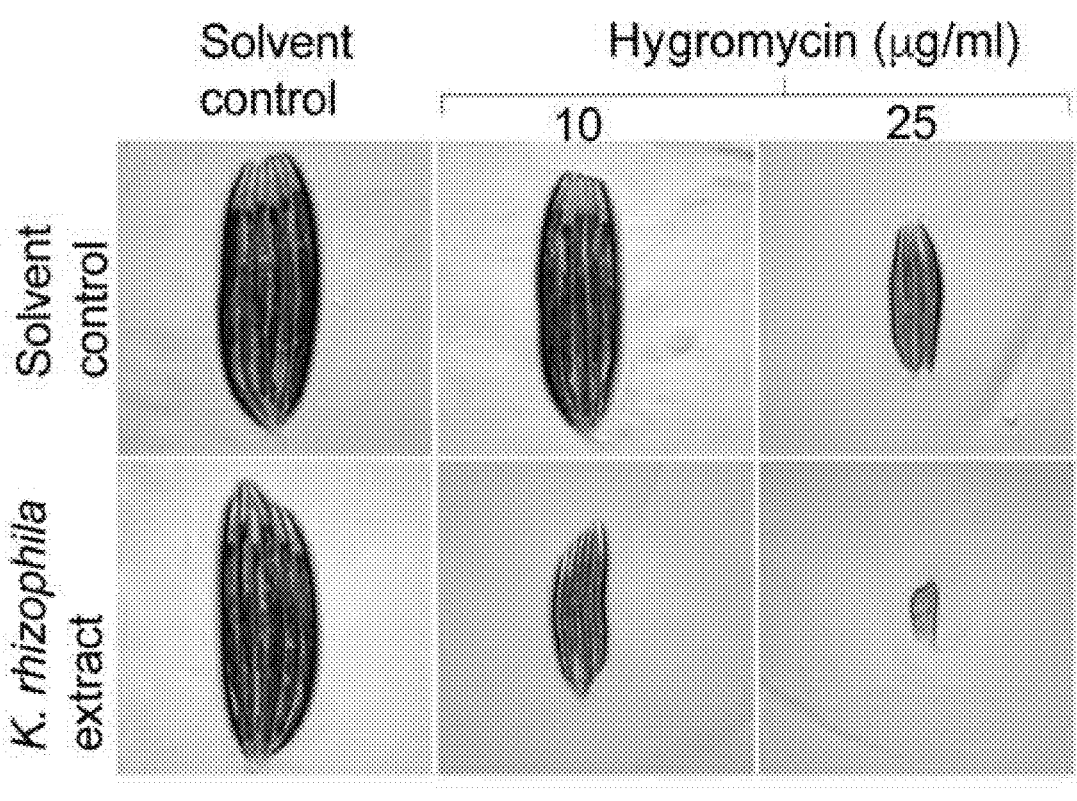
Figure 15E:
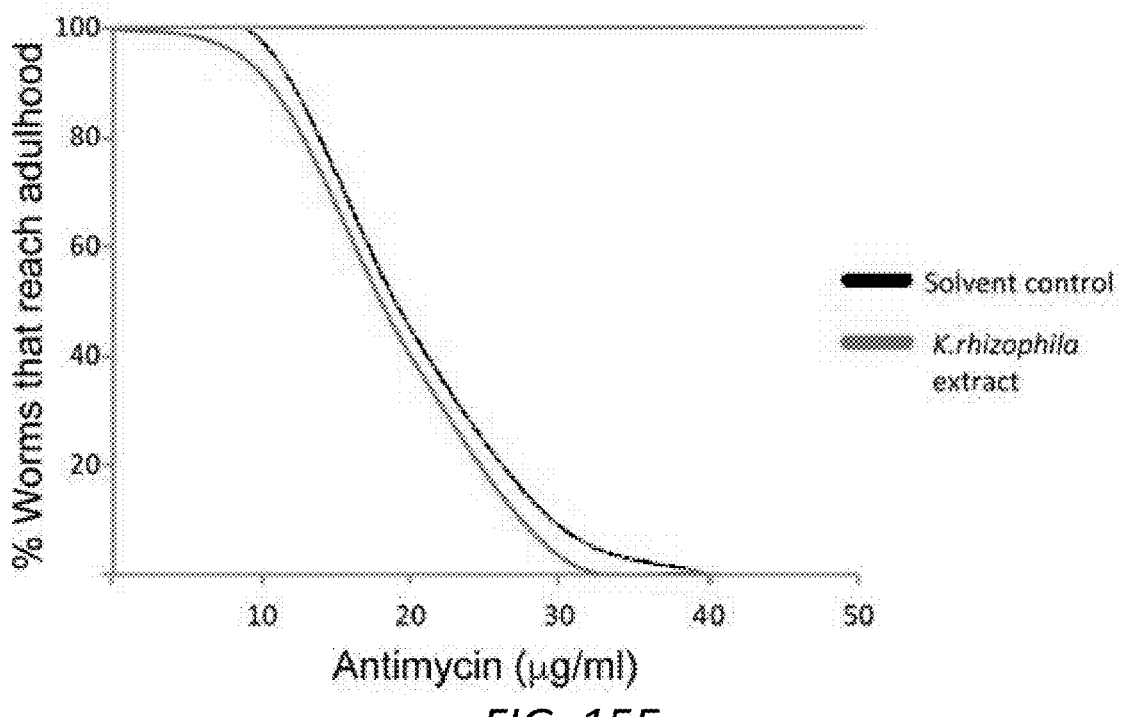

Because *K. rhizophila* carotenoids suppress the induction of *C. elegans* xenobiotic detoxification genes by translation defects, the ability of *K. rhizophila* carotenoids to increase *C. elegans* sensitivity to translational inhibitors was evaluated. While >80% of wildtype animals fed *E. coli* OP50 and 10 µg/ml hygromycin reach adulthood in four days, <10% of animals fed on *E. coli* OP50 and 10 µg/ml hygromycin and *K. rhizophila* carotenoid extract reach adulthood in four days (FIG. 3B; FIG. 15D). Carotenoids by themselves were not toxic to the worms in the absence of hygromycin (FIG. 3B; FIG. 15D). Similar results were obtained with emetine: Animals treated with *K. rhizophila* extracts were hypersensitive to emetine compared to animals fed on control extract (FIG. 3C). In addition, animals treated with *K. rhizophila* extracts were hypersensitive to cisplatin compared to animals fed on control extract (FIG. 3D). The xenobiotic hypersensitivity phenotype was not likely a generalized phenomenon because *K. rhizophila* carotenoid extract did not alter the sensitivity of animals to antimycin, a mitochondrial poison (FIG. 15E).

Figure 3E:
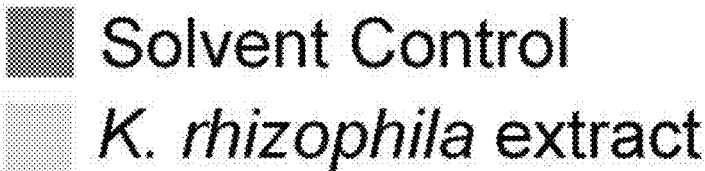
Figure 3E:
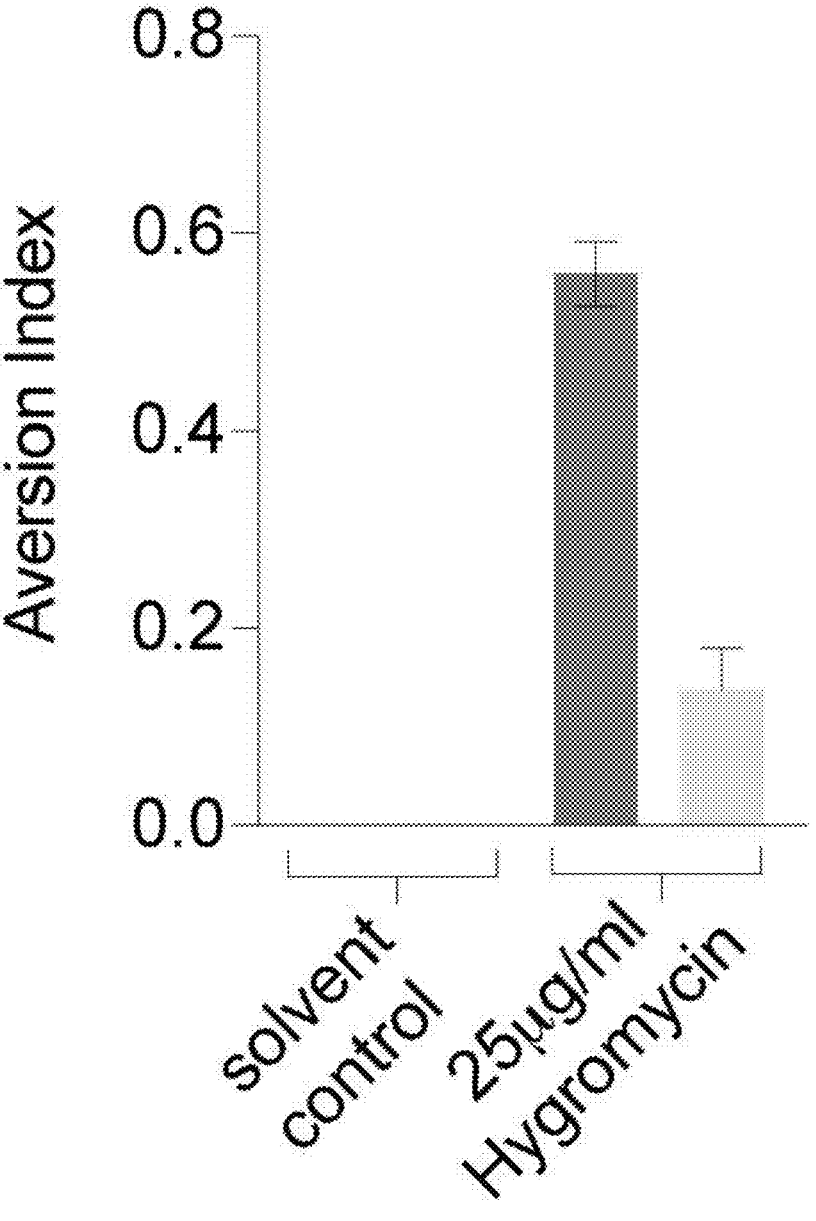
Figure 3F:
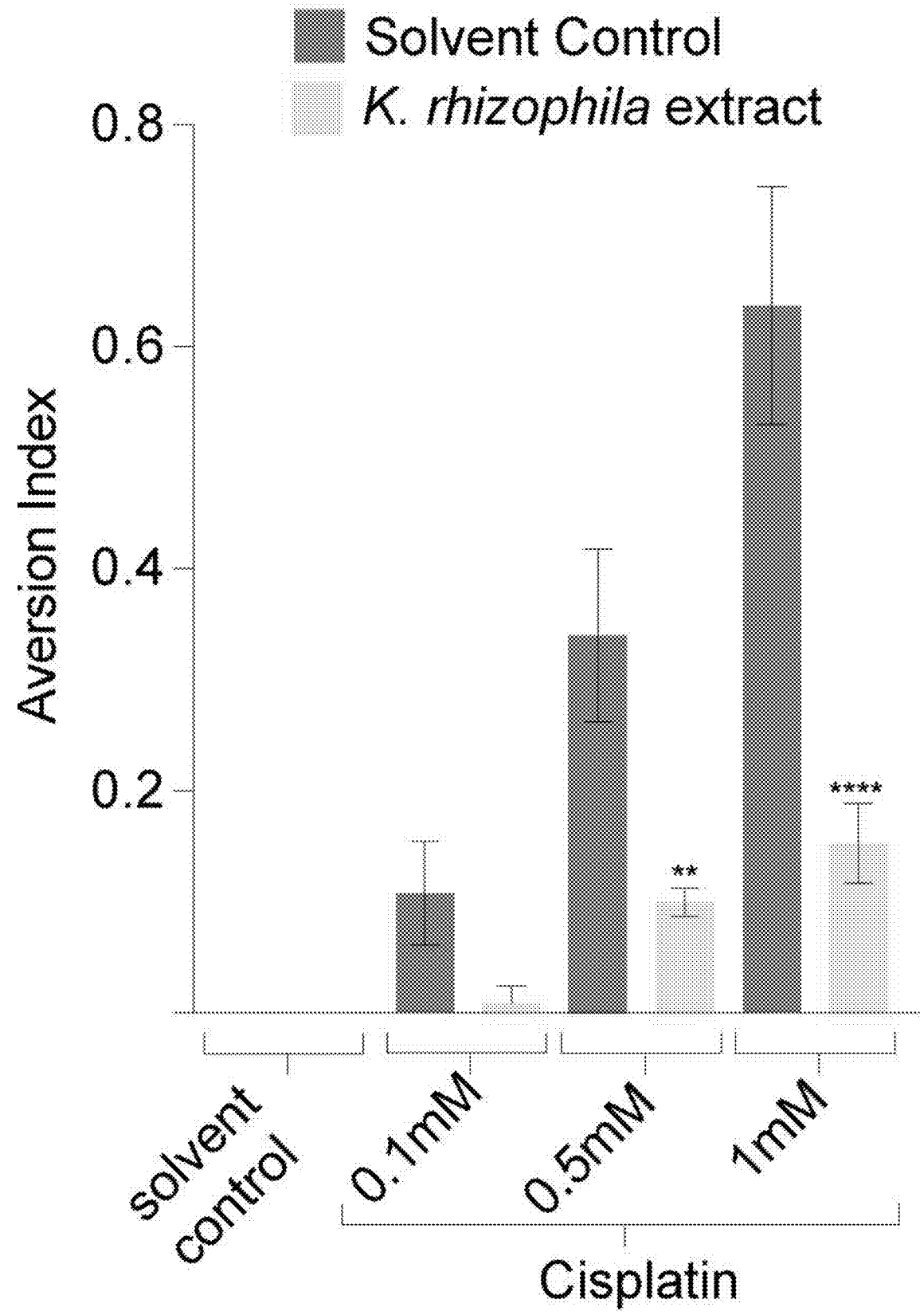

*C. elegans* food aversion behaviors are induced when animals are exposed to xenobiotics or essential gene inactivations (Melo and Ruvkun, 2012). Exposing animals to hygromycin (ribosomal translation inhibitor) or cisplatin (DNA replication inhibitor) induces strong food aversion. While ~40% of animals exposed to 25 µg/ml hygromycin display food aversion behavior, ~15% of animals exposed to 25 µg/ml hygromycin and *K. rhizophila* carotenoid extract show aversion (FIG. 3E). Similar results were obtained with cisplatin: ~50% of animals exposed to 1 mM cisplatin display aversion behavior while <20% of animals exposed to 1 mM cisplatin and *K. rhizophila* carotenoid extract display food aversion (FIG. 3F).

Figure 4A:
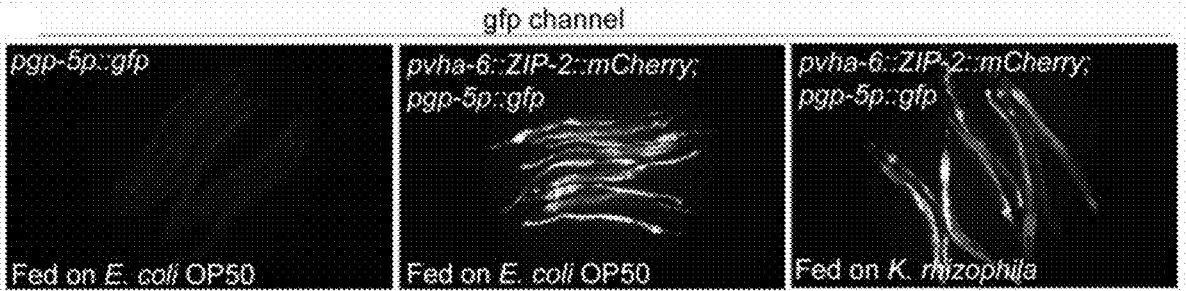

Example 2. *C. elegans* Pathway Analysis of *K. rhizophila* Inhibition of Translational Surveillance To assess how *K. rhizophila* carotenoids inhibit induction of xenobiotic detoxification response pathways, genetic epistasis analysis was conducted with a series of *C. elegans* mutations that disrupt or activate the signal transduction pathway for translational surveillance at various steps (Govindan et al., 2015). The zip-2/bZIP transcription factor is required for the induction of pgp-5p::gfp expression in response to translation inhibition and represents the last step in transcriptional induction (Govindan et al., 2015). Overexpression of ZIP-2::mCherry under a intestine-specific promoter was sufficient to induce pgp-5p::gfp expression in wildtype *C. elegans* even in the absence of translation inhibition (FIG. 4A). Whether *K. rhizophila* feeding affects pgp-5p::gfp induction was tested in a ZIP-2::mCherry overexpressing strain. pgp-5p::gfp induction was similar in animals fed on *E. coli* OP50 and *K. rhizophila* (FIG. 4A) suggesting that the *K. rhizophila* carotenoids disrupt a surveillance pathway component upstream of the ZIP-2 bZIP transcription factor (or a parallel pathway(s)).

Figure 4B:
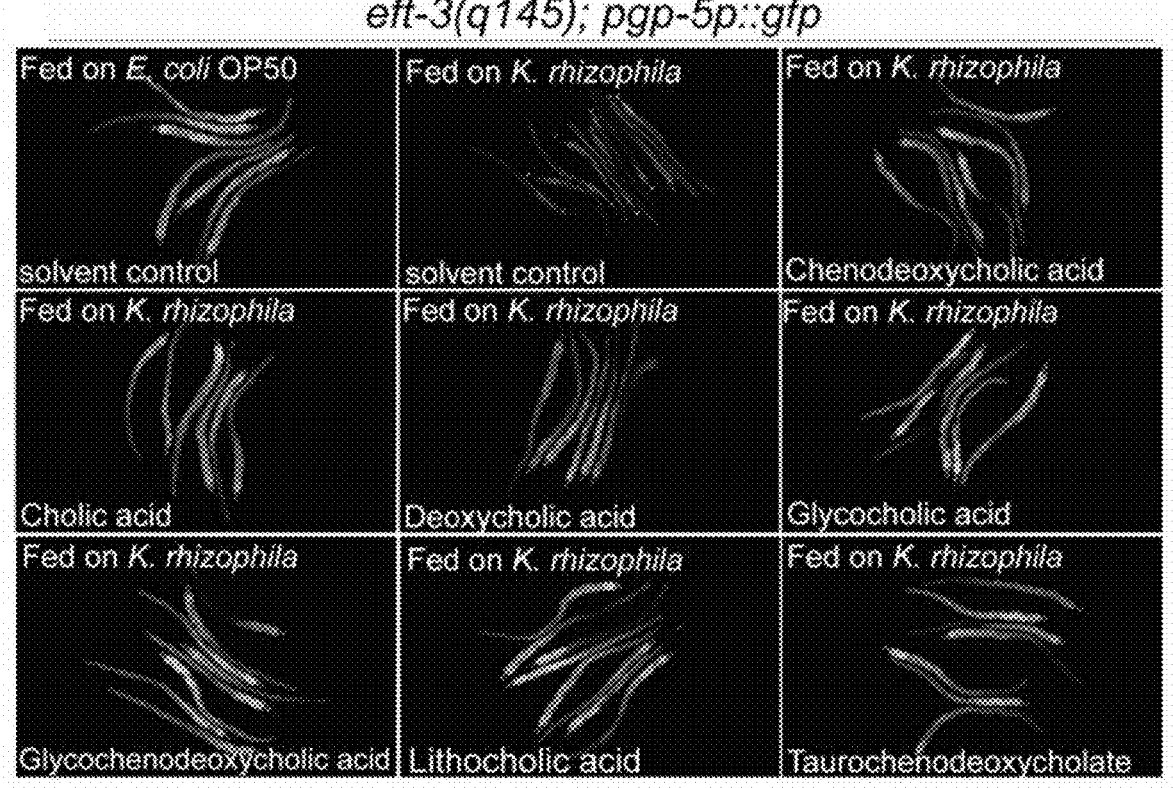
Figure 4C:
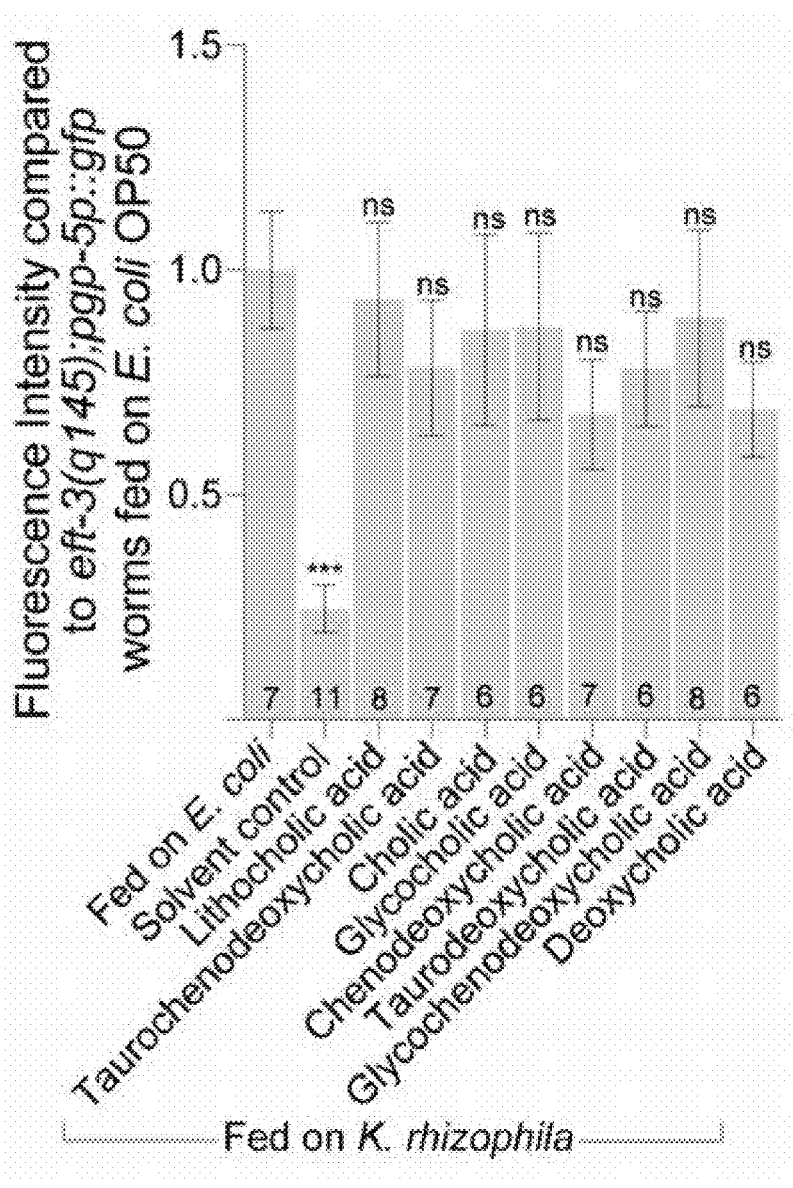

The induction of *C. elegans* xenobiotic detoxification genes by translation inhibition is dependent on a bile acid signaling pathway (Govindan et al., 2015). *C. elegans* with genetic defects in bile acid biosynthesis fail to activate pgp-5p::gfp in response to eft-3(q145), RNAi of translational components, or G418 drug inhibition of translation, but that mammalian bile acids can reanimate this signal (Govindan et al., 2015). While *K. rhizophila* feeding inhibits the induction of pgp-5p::gfp in eft-3(q145) animals, addition of exogenous mammalian bile acids reactivates GFP expression even in the presence of wild type *K. rhizophila* (FIGS. 4B&C). Thus *K. rhizophila* carotenoids act either upstream or at the bile acid signaling step of this *C. elegans* translational surveillance and response pathway.

Figure 4D:

To determine the mechanistic pathways through which *K. rhizophila* carotenoids might modulate the bile acid signaling pathway, we conducted a cherry-picked RNAi screen of *C. elegans* homologues of eukaryotic genes that mediate carotenoid binding or transport (Table 1). In this screen, we fed eft-3(q145);pgp-5p::gfp animals on *E. coli* expressing dsRNA for the *C. elegans* homologue of carotenoid binding or transport proteins. When these animals reached adulthood, they were transferred to *K. rhizophila* seeded plates and scored for GFP induction after 24 hours. In animals fed on dsRNA negative control and transferred to *K. rhizophila* plates, pgp-5p::gfp expression was abrogated. Similar reduction of pgp-5p::gfp expression was found in the animals fed on 23 other dsRNA fed animals (Table 1). However, we found that in eft-3(q145);pgp-5p::gfp animals fed on lbp-5 dsRNA, pgp-5p::gfp expression was not suppressed (FIG. 4D). lbp-5 encodes an intracellular fatty acid binding protein that is predicted to function as a transporter of hydrophobic molecules such as lipids and steroid hormones (Xu et al., 2014).

TABLE 1

Known carotenoid binding proteins genes tested for suppression of gfp expression in eft-3(q145); pgp-5p::gfp animals in response to *K. rhizophila*

| Worm Gene | Description | RNAi on eft-3(q145); pgp-5::gfp, Transferred to | |
|---|---|---|---|
| | | *E. coli* OP50 | *Kocuria* |
| | dsRNA control | + | – |
| scav-6 | ortholog of human SCARB1 (scavenger receptor class B member 1) | + | – |
| F52F12.7 | orthologous to the human gene STEROIDOGENIC ACUTE REGULATORY PROTEIN | + | – |
| F25H2.6 | ortholog of human COL4A3BP (collagen type IV alpha 3 binding protein) | + | – |
| far-7 | Fatty Acid/Retinol binding protein | + | – |
| bcmo-2 | ortholog of human RPE65 (RPE65, retinoid isomerohydrolase), BCO1 (beta-carotene oxygenase 1) and BCO2 (beta-carotene oxygenase 2) | + | – |
| bcmo-1 | ortholog of human RPE65 (RPE65, retinoid isomerohydrolase), BCO2 (beta-carotene oxygenase 2) and BCO1 (beta-carotene oxygenase 1) | + | – |
| far-8 | Fatty Acid/Retinol binding protein | + | – |
| F45H7.2 | a RhoGAP domain and a START (StAR-related lipid-transfer) domain | + | – |
| F26F4.4 | ortholog of human STARD3NL (STARD3 N-terminal like) and STARD3 (StAR related lipid transfer domain containing 3) | + | – |
| lbp-5 | predicted intracellular fatty acid binding protein (iFABP) that is most similar to the vertebrate muscle and heart FABPs | + | + |
| lbp-6 | ortholog of members of the human FABP (Fatty acid binding protein) family including FABP12 | + | – |
| far-2 | secreted fatty acid and retinol-binding proteins | + | – |
| far-1 | a fatty acid/retinol binding protein | + | – |
| T28D6.7 | ortholog of human STARD10 (StAR related lipid transfer domain containing 10) | + | – |
| scav-3 | SCA Venger receptor (C + D36 family) | + | – |
| scav-2 | ortholog of human CD36 antigen | + | – |
| far-6 | Fatty Acid/Retinol binding protein | + | – |
| npa-1 | strong binding protein for fatty acids and retinol (Vitamin A) | + | – |
| C06H2.2 | ortholog of human STARD7 (StAR related lipid transfer domain containing 7) | + | – |
| atn-1 | alpha-actinin homolog | + | – |
| far-4 | fatty acid and retinol-binding protein | + | – |
| far-3 | predicted to have lipid binding activity | + | – |
| lbp-7 | Predicted intracellular fatty acid binding protein (iFABP) | + | – |
| scav-1 | ortholog of human SCARB1 (scavenger receptor class B member 1) | + | – |
| scav-5 | ortholog of human SCARB1 (scavenger receptor class B member 1) | + | – |
| scav-4 | ortholog of human SCARB1 (scavenger receptor class B member 1) | + | – |
| K02D3.2 | human STARD4 (StAR related lipid transfer domain containing 4) | + | – |

+, GFP ON;
–, GFP OFF

Figure 16A:
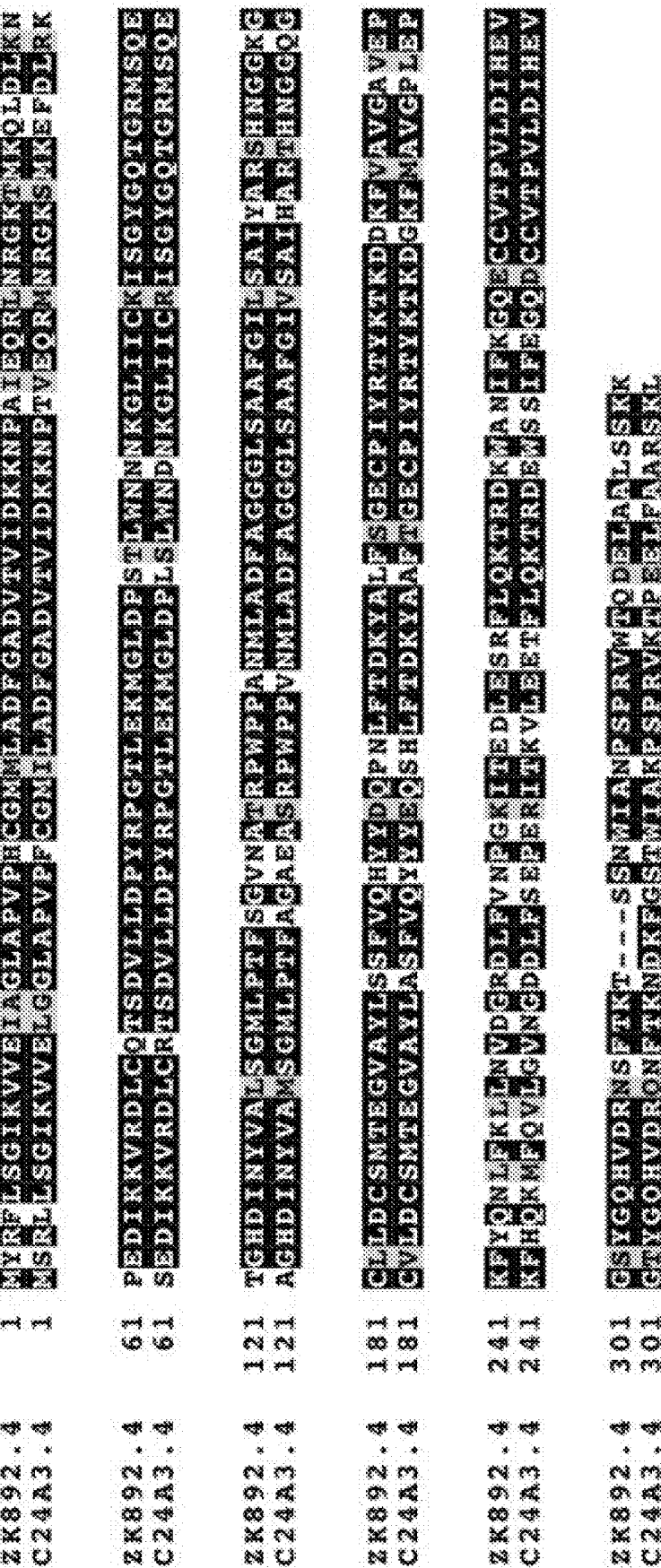
Figure 16B:
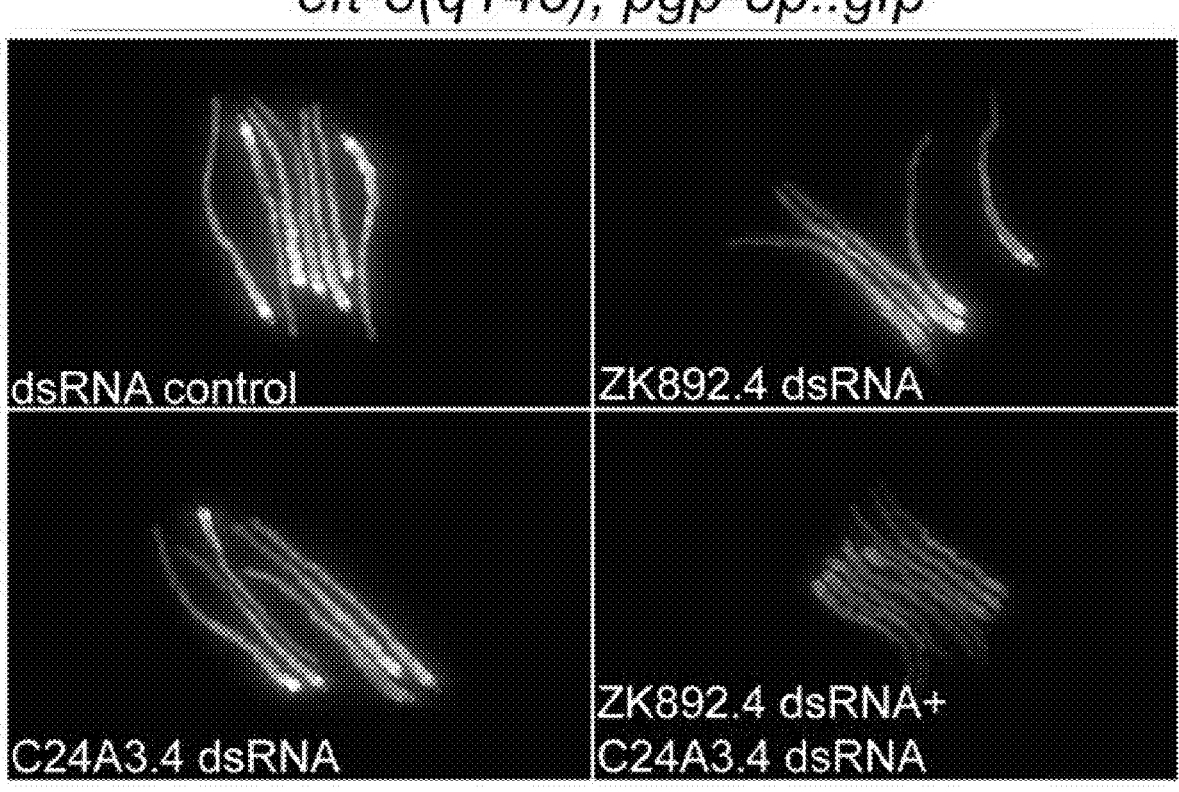

Further, to identify the eukaryotic cellular target(s) of the *K. rhizophila* carotenoid, a pull-down assay was conducted using rat liver cell extracts. Liver was chosen for identifying the carotenoid binding protein(s) for several reasons: First, it is the major site of xenobiotic detoxification. Second, it is the site of bile acid biosynthesis. Third, liver has a known carotenoid transport system. Fourth, large quantities of tissue can be easily obtained which was not feasible in *C. elegans*. To identify carotenoid binding proteins, protein extracts from rat liver were incubated with *K. rhizophila* carotenoid and unbound carotenoids were removed using size-exclusion chromatography. The carotenoid bound protein extract was subjected to anion-exchange chromatography and the protein fractions were eluted. The yellow fractions (indicating the presence of carotenoids) were pooled, concentrated and desalted. The concentrated peak was yellow-orange in color, indicating the presence of carotenoids was analyzed on native PAGE and the yellow-orange band visible was excised and mass spectrometry was conducted to identify proteins. 48 proteins were identified by mass spectrometry (Table 2). Interestingly, one of the proteins identified was FABP1 (Fatty acid binding protein1), which is the homolog of *C. elegans* LBP-5. Among the proteins identified by mass spectrometry was PAK2 (p21 protein kinase), homolog of *C. elegans* pak-1, which we previously identified as a hit in the genome-wide RNAi screen required for pgp-5p::gfp induction in response to translation inhibition (Govindan et al., 2015). To determine whether any of these 48 proteins are required for pgp-5p:: gfp induction in eft-3(q145);pgp-5p::gfp, an RNAi screen of the *C. elegans* homologs of these rat proteins was conducted. eft-3(q145);pgp-5p::gfp animals were fed on *E. coli* expressing dsRNA for the *C. elegans* homolog of each of the carotenoid binding proteins. When these animals reached adulthood, they were screened to determine whether they disrupted GFP induction. In this screen, RNAi of most of carotenoid binding proteins did not block pgp-5p::gfp induction in eft-3(q145);pgp-5p::gfp animals except for pak-1 RNAi (Table 2). Interestingly, one of the carotenoid binding proteins that was identified was AMACR (alpha-methylacyl-CoA Racemase), which is required for bile acid biosynthesis (Autio et al., 2014). In *C. elegans*, C24A3.4 and ZK892.4 are homologs of AMACR (FIG. 16A). While RNAi of C24A3.4 or ZK892.4 individually do not suppress the induction of pgp-5p::gfp in eft-3(q145);pgp-5p::gfp animals, double RNAi of C24A3.4 and ZK892.4 suppressed pgp-5p::gfp induction (FIG. 16B).

Figure 16C:
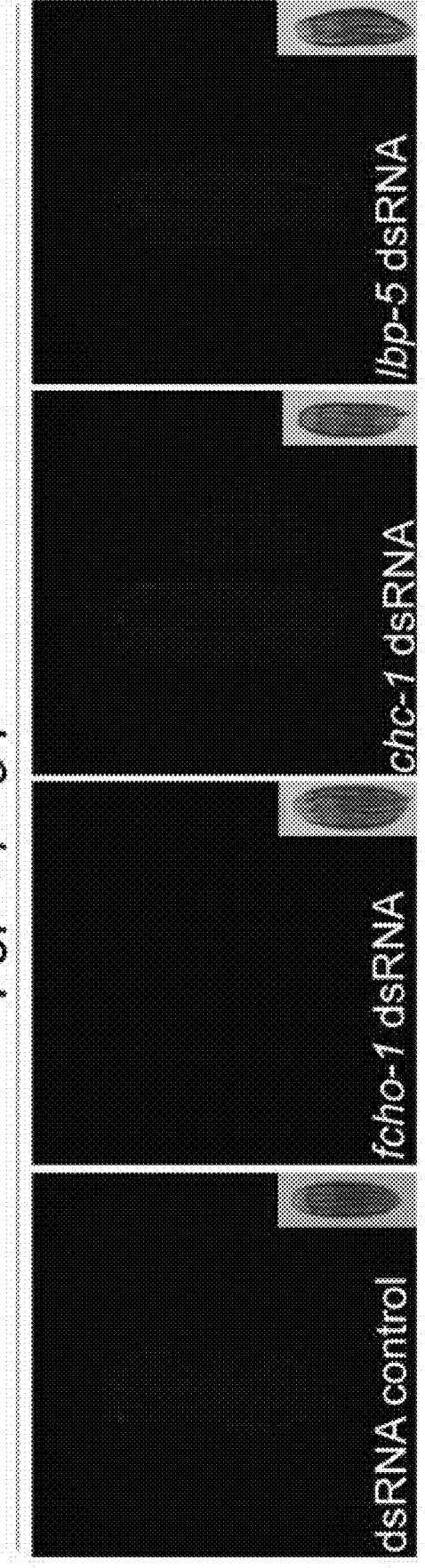

To determine whether any of these 48 *C. elegans* proteins are required for *K. rhizophila* carotenoid-induced suppression of pgp-5p::gfp induction, an RNAi screen was conducted of the *C. elegans* homologs of these proteins. When these animals reached adulthood, they were transferred to *K. rhizophila* seeded plates and scored for GFP induction after 24 hours. In animals fed on dsRNA negative control and transferred to *K. rhizophila* plates, pgp-5p::gfp expression was abrogated (Table 2). Similar reduction of pgp-5p::gfp expression was found in the animals fed in most dsRNA animals (Table 2); however, in animals treated with either chc-1 or fcho-1 or lbp-5 RNAi, pgp-5p::gfp induction was not abrogated (FIG. 4D). chc-1 encodes the *C. elegans* clathrin heavy chain ortholog while fcho-1 encodes the *C. elegans* homolog of F-BAR domain-containing fer/Cip4 homology domain-only (FCHo) family protein. Both CHC-1 and FCHO-1 mediate endocytic trafficking (Grant et al., 2006). An alternative model is that chc-1 or fcho-1 or lbp-5 RNAi by itself might induce pgp-5p::gfp expression even in the absence of ribosomal stress; however RNAi of these genes did not induce pgp-5p::gfp expression (FIG. 16C).

Figure 4E:
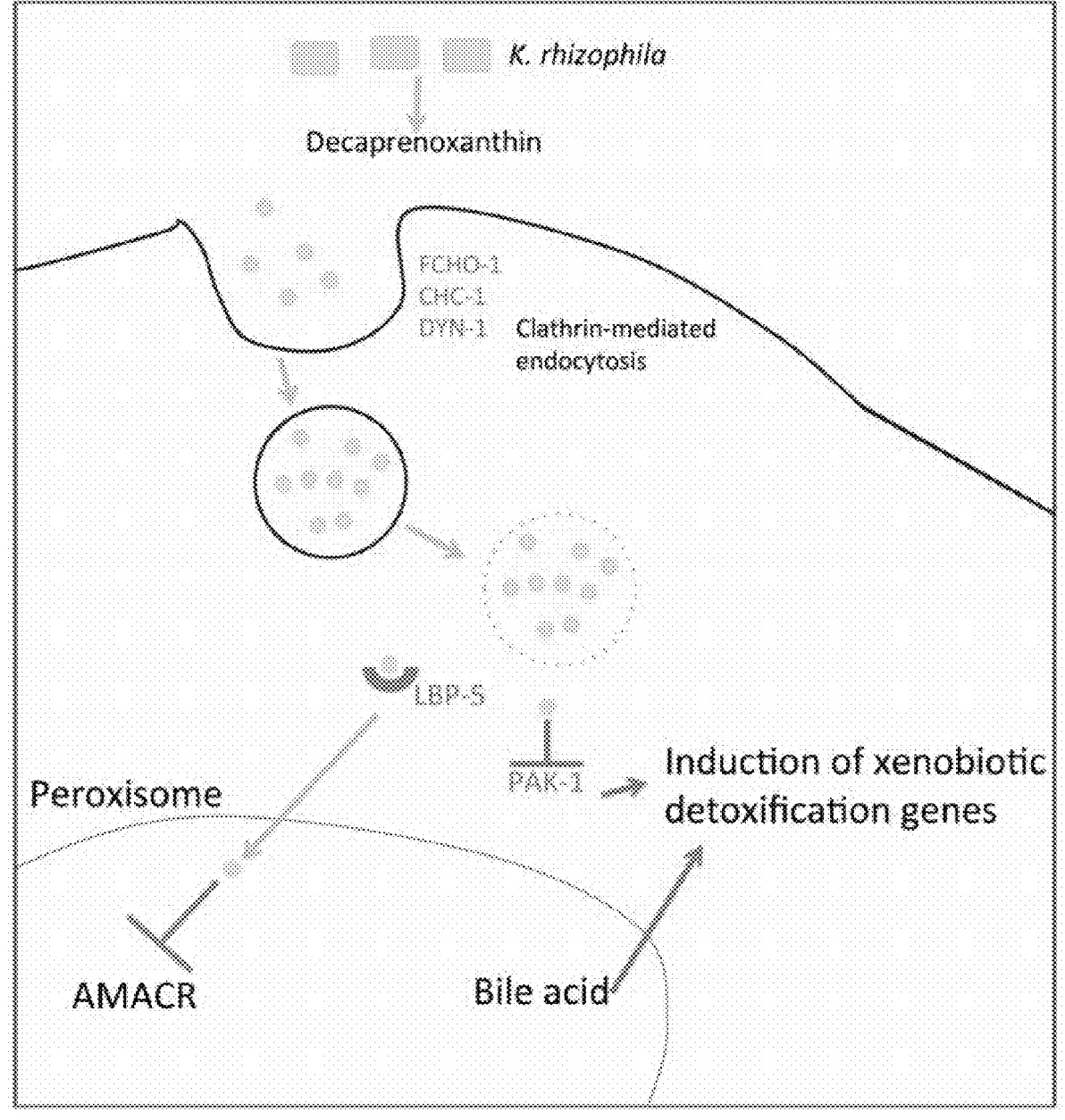

Without wishing to be bound the theory, based on the findings, a model of how *K. rhizophila* carotenoids inhibit xenobiotic detoxification response is proposed (FIG. 4E). Carotenoids released from *K. rhizophila* enter the *C. elegans* intestine via clathrin-mediated endocytosis. Within the intestinal cytoplasm, the carotenoids released from the endocytic vesicles are then bound by LBP-5 and delivered to the peroxisomes where it inhibits the bile acid biosynthesis via binding to AMACR. In addition, carotenoids also inhibit PAK-1 to disrupt xenobiotic induced upregulation of detoxification response.

TABLE 2

List of proteins identified in Mass spectrometry and effect of RNAi of their *C. elegans* homologs on the suppression of gfp expression in eft-3(q145); pgp-5p::gfp animals in response to *K. rhizophila*

| | | | | | RNAi on eft-3(q145); pgp-5::gfp, Transferred to | |
| Total | Human Protein | Worm Gene | Description | Sequencing | *E. coli* OP50 | *Kocuria* |
|---|---|---|---|---|---|---|
| | | | dsRNA control | | + | − |
| 15 | PDIA5 | D2092.4 | Protein disulfide isomerase family A | Verified | + | − |
| 10 | EHD3 | rme-1 | Plays a role in endocytic transport | Verified | + | − |
| 11 | NUDC | nud-1 | Nuclear distribution C homolog | | | |
| 8 | CLTC | chc-1 | Clathrin, heavy chain (Hc) | Verified | + | + |
| 6 | METAP2 | map-2 | Methionyl aminopeptidase 2 | Verified | + | − |
| 6 | PAK2 | pak-1 | P21-activated kinase 2 | Verified | − | − |
| 6 | EIF2S2 | K04G2.1 | Eukaryotic translation initiation factor | Verified | + | − |
| 6 | RPS4X | rps-4 | Ribosomal protein S4, X-linked | | | |

TABLE 2-continued

List of proteins identified in Mass spectrometry and effect of RNAi of their
*C. elegans* homologs on the suppression of gfp expression in eft-3(q145);
pgp-5p::gfp animals in response to *K. rhizophila*

| Total | Human Protein | Worm Gene | Description | Sequencing | RNAi on eft-3(q145); pgp-5::gfp, Transferred to | |
|---|---|---|---|---|---|---|
| | | | | | *E. coli* OP50 | *Kocuria* |
| 5 | 2-Sep | unc-59 | Filament-forming cytoskeletal GTPase | Verified | + | − |
| 5 | AMACR | C24A3.4 | alpha-methylacyl-CoA racemase | Verified | + | − |
| 5 | ABCF1 | F18E2.2 | ATP-binding cassette, sub-family F | | | |
| 5 | ACAD9 | acdh-12 | acyl-CoA dehydrogenase | Verified | + | − |
| 4 | FCHO2 | fcho-1 | FCH domain only 2 | Verified | + | + |
| 4 | PARVA | pat-6 | Parvin, alpha | Verified | + | |
| 4 | ELAC2 | hoe-1 | Zinc phosphodiesterase | Verified | + | − |
| 4 | SIRT3 | sir-2.1 | Sirtuin 3 | Verified | + | − |
| 4 | OSGEP | Y71H2AM.1 | O-sialoglycoprotein endopeptidase | Verified | + | − |
| 4 | TAT | tatn-1 | Tyrosine aminotransferase | Verified | + | − |
| 4 | PRKAB1 | F55F3.1 | Protein kinase, AMP-activated | Verified | + | − |
| 4 | PDK2 | ZK370.5 | Pyruvate dehydrogenase kinase | | | |
| 4 | MESDC2 | bmy-1 | Chaperone | | + | − |
| 7 | 7-Sep | unc-59 | Filament-forming cytoskeletal GTPase | Sequence verified | + | − |
| 4 | ITSN1 | itsn-1 | Adapter protein; endocytosis | Sequence verified | + | − |
| 4 | ARMC1 | K05C4.7 | Armadillo repeat containing 1 | Sequence verified | + | − |
| 4 | ITIH4 | No homolog | Inter-alpha-trypsin inhibitor heavy chain | | | |
| 3 | DNAJB11 | dnj-20 | DnaJ (Hsp40) homolog, subfamily B | No RNAi clone | | |
| 3 | 9-Sep | unc-61 | Filament-forming cytoskeletal GTPase | Sequence verified | + | − |
| 3 | 11-Sep | unc-61 | Filament-forming cytoskeletal GTPase | Sequence verified | + | − |
| 3 | ITPA | ZC395.7 | Inosine triphosphatase | Sequence verified | + | − |
| 3 | SLC9A3R1 | nrfl-1 | Solute carrier family 9 | Sequence verified | + | − |
| 3 | FABP1 | 1bp-5 | Fatty acid binding protein 1 | Sequence verified | + | + |
| 3 | PRKAG1 | aakg-1 | Protein kinase, AMP-activated | Sequence verified | + | − |
| 3 | DECR1 | F53C11.3 | 2,4-dienoyl CoA reductase 1, mitochondrial | No RNAi clone | | |
| 3 | DDX19A | ddx-19 | DEAD box polypeptide 19A | Sequence verified | + | − |
| 3 | GDI1 | gdi-1 | GDP dissociation inhibitor 1 | Sequence verified | + | − |
| 3 | MARS | mars-1 | methionyl-tRNA synthetase | No RNAi clone | | |
| 3 | FAM45A | No homolog | Family with sequence similarity 45 | | | |
| 3 | NAA15 | Y50D7A.4 | N(alpha)-acetyltransferase 15 | Sequence verified | + | − |
| 3 | GRB2 | sem-5 | Growth factor receptor-bound protein 2 | Sequence verified | + | − |
| 3 | CAPN2 | clp-1 | Calcium-regulated non-lysosomal protease | Sequence verified | + | − |
| 3 | CYFIP1 | gex-2 | Cytoplasmic FMR1 interacting protein 1 | Sequence verified | + | − |
| 3 | HADH | B0272.3 | hydroxyacyl-CoA dehydrogenase | Sequence verified | + | − |

TABLE 2-continued

List of proteins identified in Mass spectrometry and effect of RNAi of their
C. elegans homologs on the suppression of gfp expression in eft-3(q145);
pgp-5p::gfp animals in response to K. rhizophila

| Total | Human Protein | Worm Gene | Description | Sequencing | RNAi on eft-3(q145); pgp-5::gfp, Transferred to | |
|---|---|---|---|---|---|---|
| | | | | | E. coli OP50 | Kocuria |
| 3 | DDX46 | F53H1.1 | DEAD box; role in splicing | Sequence verified | + | – |
| 3 | PUF60 | rnp-6 | poly-U binding splicing factor | Sequence verified | + | – |
| 3 | AP3D1 | apd-3 | Adaptor; endocytosis | Sequence verified | + | – |
| 2 | API5 | No homolog | Antiapoptotic factor; role in protein assembly | Sequence verified | + | – |
| 2 | CRK | Y41D4B. 13 | V-crk sarcoma virus CT10 oncogene homolog | Sequence verified | + | – |

+ GFP ON;
– GFP OFF;
no entry = not tested

REFERENCES FOR EXAMPLES

Giuffrida, D. et al. Characterisation of the C50 carotenoids produced by strains of the cheese-ripening bacterium *Arthrobacter arilaitensis*. *International Dairy Journal* 55, 10-16 (2016).

Pilbrow, J., Sabherwal, M., Garama, D. & Carne, A. A novel fatty acid-binding protein-like carotenoid-binding protein from the gonad of the New Zealand sea urchin *Evechinus chloroticus*. *PLoS ONE* 9, e106465 (2014).

Monteiro-Vitorello, C. B. et al. The genome sequence of the gram-positive sugarcane pathogen *Leifsonia xyli* subsp. *xyli*. *Mol. Plant Microbe Interact.* 17, 827-836 (2004).

Morohoshi, T., Wang, W.-Z., Someya, N. & Ikeda, T. Genome sequence of *Microbacterium testaceum* StLB037, an N-acylhomoserine lactone-degrading bacterium isolated from potato leaves. *J Bacteriol* 193, 2072-2073 (2011).

Christopherson, M. R. et al. The genome sequences of *Cellulomonas fimi* and "Cellvibrio gilvus" reveal the cellulolytic strategies of two facultative anaerobes, transfer of 'Cellvibrio gilvus' to the genus *Cellulomonas*, and proposal of *Cellulomonas gilvus* sp. nov. *PLoS ONE* 8, e53954 (2013).

Ivanova, N. et al. Complete genome sequence of *Sanguibacter keddieii* type strain (ST-74). *Stand Genomic Sci* 1, 110-118 (2009).

Pukall, R. et al. Complete genome sequence of *Jonesia denitrificans* type strain (Prevot 55134). *Stand Genomic Sci* 1, 262-269 (2009).

Monnet, C. et al. The *Arthrobacter arilaitensis* Rel 17 genome sequence reveals its genetic adaptation to the surface of cheese. *PLoS ONE* 5, e15489 (2010).

Kalinowski, J. et al. The complete *Corynebacterium glutamicum* ATCC 13032 genome sequence and its impact on the production of L-aspartate-derived amino acids and vitamins. *J. Biotechnol.* 104, 5-25 (2003).

Nishio, Y. et al. Comparative complete genome sequence analysis of the amino acid replacements responsible for the thermostability of *Corynebacterium efficiens*. *Genome Res.* 13, 1572-1579 (2003).

Sims, D. et al. Complete genome sequence of *Kytococcus sedentarius* type strain (541). *Stand Genomic Sci* 1, 12-20 (2009).

Land, M. et al. Complete genome sequence of *Beutenbergia cavernae* type strain (HKI 0122). *Stand Genomic Sci* 1, 21-28 (2009).

Lapidus, A. et al. Complete genome sequence of *Brachybacterium faecium* type strain (Schefferle 6-10). *Stand Genomic Sci* 1, 3-11 (2009).

Abt, B. et al. Complete genome sequence of *Cellulomonas flavigena* type strain (134). *Stand Genomic Sci* 3, 15-25 (2010).

Liaaen-Jensen, S., Hertzberg, S., Weeks, O. B. & Schwieter, U. Bacterial carotenoids XXVII. C50-carotenoids. 3. Structure determination of dehydrogenans-P439. *Acta Chem Scand* 22, 1171-1186 (1968).

Fukuoka, S., Ajiki, Y., Ohga, T., Kawanami, Y. & Izumori, K. Production of dihydroxy C50-carotenoid by Aureobacterium sp. FERM P-18698. *Biosci. Biotechnol. Biochem.* 68, 2646-2648 (2004).

Arpin, N., Fiasson, J. L., Norgård, S., Borch, G. & Liaaen-Jensen, S. Bacterial carotenoids, XLVI. C50-Carotenoids, 14. C50-Carotenoids from *Arthrobacter glacialis*. *Acta Chem. Scand., B, Org. Chem. Biochem.* 29, 921-926 (1975).

Sutthiwong, N. & Dufossé, L. Production of carotenoids by *Arthrobacter arilaitensis* strains isolated from smear-ripened cheeses. *FEMS Microbiol. Lett.* 360, 174-181 (2014).

Weeks, O. B., Montes, A. R. & Andrewes, A. G. Structure of the principal carotenoid pigment of *Cellulomonas biazotea*. *J Bacteriol* 141, 1272-1278 (1980).

Krubasik, P. et al. Detailed biosynthetic pathway to decaprenoxanthin diglucoside in *Corynebacterium glutamicum* and identification of novel intermediates. *Arch. Microbiol.* 176, 217-223 (2001).

Melo, J. A. & Ruvkun, G. Inactivation of conserved *C. elegans* genes engages pathogen- and xenobiotic-associated defenses. *Cell* 149, 452-466 (2012).

Dunbar, T. L. T., Yan, Z. Z., Balla, K. M. K., Smelkinson, M. G. M. & Troemel, E. R. E. *C. elegans* detects pathogen-induced translational inhibition to activate immune signaling. *Cell Host Microbe* 11, 375-386 (2012).

Govindan, J. A. et al. Lipid signalling couples translational surveillance to systemic detoxification in *Caenorhabditis elegans. Nat Cell Biol* 17, 1294-1303 (2015).

Bérdy, J. Bioactive microbial metabolites. *J. Antibiot.* 58, 1-26 (2005).

Félix, M.-A. & Braendle, C. The natural history of *Caenorhabditis elegans. Curr. Biol.* 20, R965-9 (2010).

Takarada, H. et al. Complete genome sequence of the soil actinomycete *Kocuria rhizophila. J Bacteriol* 190, 4139-4146 (2008).

Klassen, J. L. Phylogenetic and evolutionary patterns in microbial carotenoid biosynthesis are revealed by comparative genomics. *PLoS ONE* 5, e11257 (2010).

Krubasik, P., Kobayashi, M. & Sandmann, G. Expression and functional analysis of a gene cluster involved in the synthesis of decaprenoxanthin reveals the mechanisms for C50 carotenoid formation. *Eur. J. Biochem.* 268, 3702-3708 (2001).

Krubasik, P. et al. Detailed biosynthetic pathway to decaprenoxanthin diglucoside in *Corynebacterium glutamicum* and identification of novel intermediates. *Arch. Microbiol.* 176, 217-223 (2001).

Norgård, S., Aasen, A. J. & Liaaen-Jensen, S. Bacterial carotenoids. 32. C50-carotenoids 6. Carotenoids from *Corynebacterium poinsettiae* including four new C50-diols. *Acta Chem Scand* 24, 2183-2197 (1970).

Tao, L., Yao, H. & Cheng, Q. Genes from a Dietzia sp. for synthesis of C40 and C50 beta-cyclic carotenoids. *Gene* 386, 90-97 (2007).

Netzer, R. et al. Biosynthetic pathway for γ-cyclic sarcinaxanthin in *Micrococcus luteus*: heterologous expression and evidence for diverse and multiple catalytic functions of C(50) carotenoid cyclases. *J Bacteriol* 192, 5688-5699 (2010).

Heider, S. A. E., Peters-Wendisch, P. & Wendisch, V. F. Carotenoid biosynthesis and overproduction in *Corynebacterium glutamicum. BMC Microbiol.* 12, 198 (2012).

Monnet, C. et al. The *Arthrobacter arilaitensis* Rel 17 genome sequence reveals its genetic adaptation to the surface of cheese. *PLoS ONE* 5, e15489 (2010).

Giuffrida, D. et al. Characterisation of the C50 carotenoids produced by strains of the cheese-ripening bacterium *Arthrobacter arilaitensis. International Dairy Journal* 55, 10-16 (2016).

Sutthiwong, N. & Dufossé, L. Production of carotenoids by *Arthrobacter arilaitensis* strains isolated from smear-ripened cheeses. *FEMS Microbiol. Lett.* 360, 174-181 (2014).

Yoneda, T. et al. Compartment-specific perturbation of protein handling activates genes encoding mitochondrial chaperones. *J. Cell. Sci.* 117, 4055-4066 (2004).

Calfon, M. et al. IRE1 couples endoplasmic reticulum load to secretory capacity by processing the XBP-1 mRNA. *Nature* 415, 92-96 (2002).

O'Rourke, D., Baban, D., Demidova, M., Mott, R. & Hodgkin, J. Genomic clusters, putative pathogen recognition molecules, and antimicrobial genes are induced by infection of *C. elegans* with *M. nematophilum. Genome Res.* 16, 1005-1016 (2006).

Troemel, E. R. et al. p38 MAPK regulates expression of immune response genes and contributes to longevity in *C. elegans. PLoS Genet* 2, e183 (2006).

Bolz, D. D., Tenor, J. L. & Aballay, A. A conserved PMK-1/p38 MAPK is required in *Caenorhabditis elegans* tissue-specific immune response to *Yersinia pestis* infection. *J Biol Chem* 285, 10832-10840 (2010).

Edge, R., McGarvey, D. J. & Truscott, T. G. The carotenoids as anti-oxidants—a review. *J. Photochem. Photobiol. B, Biol.* 41, 189-200 (1997).

Xu, M., Choi, E.-Y. & Paik, Y.-K. Mutation of the lbp-5 gene alters metabolic output in *Caenorhabditis elegans. BMB Rep* 47, 15-20 (2014).

Autio, K. J. et al. Role of AMACR (α-methylacyl-CoA racemase) and MFE-1 (peroxisomal multifunctional enzyme-1) in bile acid synthesis in mice. *Biochem J* 461, 125-135 (2014).

Grant, B. D. & Sato, M. Intracellular trafficking. *WormBook* 1-9 (2006). doi:10.1895/wormbook.1.77.1

OTHER EMBODIMENTS

It is to be understood that while embodiments of the invention have been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A therapeutic composition formulated for oral delivery comprising:

a genetically engineered microbe that introduces a carotenogenic modification to synthesize an increased level of a C50 carotenoid compound relative to the level synthesized before the genetic engineering, the C50 carotenoid compound, and a pharmaceutically acceptable carrier, wherein the microbe and the C50 carotenoid compound are each in a therapeutically effective amount to reduce nausea, vomiting, food aversion, and/or loss of appetite;

wherein the C50 carotenoid compound synthesized by the genetically engineered microbe is at least 20% w/w of the therapeutic composition, and wherein the therapeutic composition is a tablet, troche, gummy, or gel.

2. The therapeutic composition of claim 1, wherein the microbe is a cultured microbe.

3. The therapeutic composition of claim 1, wherein the C50 carotenoid compound is purified.

4. The therapeutic composition of claim 1, wherein the C50 carotenoid compound is selected from the group consisting of decaprenoxanthin, C50-astaxanthin, C50-β-carotene, C50-carotene (n=3) (16,16-diisopentenylphytoene), C50-zeaxanthin, C50-caloxanthin, C50-nostoxanthin, sarcinaxanthin, sarprenoxanthin, acyclic C50 carotenoid bacterioruberin, C50-canthaxanthin, C50-lycopene, C50-phytoene, and combinations thereof.

5. The therapeutic composition of claim 4, wherein the C50 carotenoid compound is decaprenoxanthin.

6. The therapeutic composition of claim 1, wherein the microbe is living or viable.

7. The therapeutic composition of claim 1, wherein the microbe has been killed.

8. The therapeutic composition of claim 1, wherein the microbe is selected from the group consisting of *Kocuria rhizophila, Corynebacterium glutamicum, Arthrobacter arilaitensis*, and combinations thereof.

* * * * *

SEQUENCE LISTING

```
<160> NUMBER OF SEQ ID NOS: 21

<210> SEQ ID NO 1
<211> LENGTH: 530
<212> TYPE: PRT
<213> ORGANISM: Arthrobacter arilaitensis

<400> SEQUENCE: 1

Met Asn His Gln Asp Gln Glu Val Val Val Ile Gly Gly Gly Phe Ser
1               5                   10                  15

Gly Leu Ala Ser Ala Gly Leu Leu Ala Ala Arg Gly Cys Lys Val Thr
            20                  25                  30

Leu Ile Glu Gln Gln Glu His Pro Gly Gly Arg Ser Gly Arg Leu Glu
        35                  40                  45

Arg Glu Gly Phe Arg Phe Asp Thr Gly Pro Ser Trp Tyr Leu Met Pro
    50                  55                  60
```

```
Glu Val Phe Asp His Trp Phe Arg Leu Met Gly Thr Ser Thr Ala Glu
65                  70                  75                  80

Gln Leu Asp Leu Arg Glu Leu Pro Thr Gly Tyr Arg Val Phe Phe Gln
                85                  90                  95

Asn Arg Gln Ala Pro Ala Asp Phe Gly Ile Gly Ala Ala Ala Ser Asp
            100                 105                 110

Leu Phe Glu Thr Leu Glu Pro Gly Ser Ala Pro Ala Leu Glu Arg Tyr
        115                 120                 125

Leu Arg Thr Ala Lys Glu Gly Tyr Glu Leu Ala Leu Glu His Phe Leu
    130                 135                 140

Tyr Asp Asp Phe His Ser Leu Lys Ser Leu Leu Asp Pro Arg Ile Leu
145                 150                 155                 160

Arg Arg Ala Pro Gln Leu Ala Lys Leu Leu Ser Thr Ser Leu Gln Ser
                165                 170                 175

His Val Ala Arg Arg Phe Ala Ser Asn Glu Ile Arg Gln Val Leu Gly
            180                 185                 190

Tyr Pro Ala Val Phe Leu Gly Ser Ser Pro Glu Lys Thr Pro Ala Leu
        195                 200                 205

Tyr Gln Leu Met Ser His Leu Asp Leu Ala Asp Gly Val Lys Tyr Pro
    210                 215                 220

Met Gly Gly Phe Ala Ala Val Ala Asp Ala Met Ala Gln Leu Ala Arg
225                 230                 235                 240

Lys His Gly Ala Gln Ile Gln Leu Gly Ala Thr Ala Thr Ala Ile Glu
                245                 250                 255

Thr Ser Thr Gly Lys Asn Leu Ala Val Ser Ala Val Arg Trp Ile Asp
            260                 265                 270

Ala Asn Gly Thr Leu His Arg Thr Pro Ala Thr Lys Val Ile Gly Ala
            275                 280                 285

Ala Asp Val Arg His Leu Glu Gly Glu Leu Leu Pro Glu Ser Leu Gln
    290                 295                 300

Thr His Thr Ala Lys Ser Phe Ala Arg Lys Asp Pro Gly Pro Ser Ala
305                 310                 315                 320

Val Leu Leu Cys Leu Gly Ile Lys Gly Lys Leu Pro Gln Leu Glu His
                325                 330                 335

His Asn Leu Leu Phe Thr Glu Asp Trp Ser Glu Asn Phe Ser Arg Ile
            340                 345                 350

Arg Gln Gly Arg Glu Leu Glu Pro Glu Thr Ser Ile Tyr Val Cys Lys
        355                 360                 365

Pro Ser Ala Thr Asp Pro Gly Thr Ala Pro Glu Gly Cys Glu Asn Leu
370                 375                 380

Phe Ile Leu Val Pro Ala Pro Ala Leu Pro Glu Trp Gly Ile Gly Ala
385                 390                 395                 400

Ala Asp Gly Gln Gly Asp Ala Ala Val Glu Ala Val Ala Glu Ala Ala
            405                 410                 415

Ile Asp Gln Leu Ser Ala Trp Ala Arg Ile Asp Asp Leu Arg Glu Arg
            420                 425                 430

Ile Val Val Arg Gln Ser Ile Gly Pro Gly Asp Phe Ala Gln Gln Tyr
        435                 440                 445

Gly Ala Tyr Arg Gly Gly Ala Leu Gly Leu Ala His Thr Leu Gly Gln
    450                 455                 460

Ser Ala Met Leu Arg Pro Gly Asn Arg Ser Ala Lys Val Glu Gly Leu
465                 470                 475                 480
```

-continued

```
Tyr Tyr Ala Gly Ser Thr Val Arg Pro Gly Ile Gly Val Pro Met Cys
              485             490             495

Leu Ile Ser Gly Glu Leu Ala Ala Lys Ala Val Leu Gly Ile Lys Asp
              500             505             510

Ala Gly Pro Met Pro Glu Asn Arg Ser Val Met Arg Ala Gln Glu Ala
          515             520             525

Gly Ala
    530

<210> SEQ ID NO 2
<211> LENGTH: 621
<212> TYPE: PRT
<213> ORGANISM: Kocuria rhizophila

<400> SEQUENCE: 2

Met Thr Asp Gly Asn Arg Thr Thr Arg His Pro Thr Arg Pro Glu Asn
1               5               10              15

Ala His Arg Gly Ser Pro Asp Gly Gly Ala Pro Arg Thr Val Val Val
              20              25              30

Gly Gly Gly Phe Ala Gly Leu Ala Thr Ala Gly Leu Leu Ala Arg Asp
          35              40              45

Gly His Arg Val Thr Leu Leu Glu Gln Arg Asp Thr Leu Gly Gly Arg
    50              55              60

Ser Gly Arg Trp Ser Ala Glu Gly Phe Thr Phe Asp Thr Gly Pro Ser
65              70              75              80

Trp Tyr Leu Met Pro Glu Val Ile Asp Arg Trp Phe Thr Leu Met Gly
              85              90              95

Ser Ser Ala Asp Glu Gln Leu Asp Leu Arg Arg Leu Asp Pro Gly Tyr
              100             105             110

Arg Thr Phe Phe Glu Gln His Leu Asp Glu Pro Pro Thr Asp Val Arg
          115             120             125

Ala Gly His Ala Glu Glu Leu Phe Glu Arg Leu Asp Pro Gly Ser Ser
    130             135             140

Glu Ala Leu Arg Ala Tyr Leu Gly Ser Gly Ala Glu Val Tyr Asp Leu
145             150             155             160

Ala Lys Lys His Phe Leu Tyr Thr Asn Phe Ser Arg Pro Thr Asp Leu
              165             170             175

Ala Arg Ala Glu Val Leu Arg Asn Leu Pro Arg Leu Gly Gly Leu Leu
              180             185             190

Ser Thr Ser Met Gln Arg Tyr Val Ala Ala Arg Phe Arg Asp Pro Arg
          195             200             205

Gln Arg Gln Ile Leu Gly Tyr Pro Ala Val Phe Leu Gly Ala Ser Pro
    210             215             220

Asp Thr Ala Pro Ala Met Tyr His Leu Met Ser His Leu Asp Leu Thr
225             230             235             240

Asp Gly Val Gln Tyr Pro Val Gly Gly Phe Ala Ala Leu Val Asp Ala
              245             250             255

Met Glu Arg Leu Val Arg Ala Ala Gly Val Glu Ile Val Thr Gly Ala
              260             265             270

Glu Val Thr Gly Ile Glu Val Ala Pro Ala Pro Ala Ser Leu Arg Ser
          275             280             285

Arg Val Gly Ala Ala Arg Ala Arg Arg Ser Ala Gly Ser Val Thr
    290             295             300

Gly Val Thr Trp Arg Ala Ala Ala Pro Glu Glu Gly Val Arg Ala Gly
305             310             315             320
```

-continued

```
Gln Asp Gly Ala Ala Gly Ala Pro Gly Ala Arg Gly Ala Val Arg Asp
                325             330             335

Ala Asp Gly Pro Gly Gly Val Val Glu Gly Pro Gly Val Val Ala Glu
            340             345             350

Gly Arg Gly Thr Arg Thr Asp Ala Ser Ala Glu Ala Arg Gly Ala Gly
            355             360             365

Thr Asp Ala Pro Ala Gly Gln Pro Gly Asp Gly Glu Glu Arg Thr Val
    370             375             380

Thr Ala Asp Val Val Ile Gly Ala Ala Asp Leu His His Leu Gln Thr
385             390             395             400

Arg Leu Leu Pro Asp Asp Phe Arg Ala Pro Glu Ser Arg Trp Thr His
            405             410             415

Arg Asp Pro Gly Pro Ser Gly Val Leu Val Cys Leu Gly Val Arg Gly
            420             425             430

Lys Leu Pro Gln Leu Val His His Asn Leu Leu Phe Thr Ala Asp Trp
            435             440             445

Asp Asp Asn Phe Gly Arg Ile Ala Asp Gly Thr Pro Leu Ala Glu Gln
    450             455             460

Thr Ser Ile Tyr Val Ser Met Thr Ser Ala Thr Asp Pro Gly Thr Ala
465             470             475             480

Pro Glu Gly Asp Glu Asn Leu Phe Ile Leu Val Pro Ser Pro Ala Val
            485             490             495

Pro Glu Trp Gly Arg Gly Gly Val Arg Thr Pro Asp Thr Asp Glu Pro
            500             505             510

Gly Ser Pro Gln Val Glu Arg Val Ala Asp Ala Ala Ile Ala Gln Leu
            515             520             525

Ala Arg Trp Ala Glu Ile Pro Asp Leu Ala Glu Arg Ile Val Val Arg
            530             535             540

Arg Thr Tyr Gly Pro Gly Asp Phe Glu Ala Gln Phe Asn Ala Trp Arg
545             550             555             560

Gly Ser Met Leu Gly Pro Gly His Thr Leu Arg Gln Ser Ala Leu Phe
            565             570             575

Arg Pro Gly Val Thr Asp Pro Gly Ile Glu Gly Leu Tyr Tyr Ala Gly
            580             585             590

Ser Ser Val Arg Pro Gly Ile Gly Val Pro Met Cys Leu Ile Ser Ser
            595             600             605

Glu Val Val Arg Asp Ala Val Arg Glu Arg Gly Gly Arg
    610             615             620
```

```
<210> SEQ ID NO 3
<211> LENGTH: 566
<212> TYPE: PRT
<213> ORGANISM: Micrococcus luteus

<400> SEQUENCE: 3
```

```
Met Ser Ala Arg Asp Thr Ala Leu Gly Pro Arg Thr Val Val Val Gly
1               5               10              15

Gly Gly Phe Ala Gly Leu Ala Thr Ala Gly Leu Leu Ala Arg Asp Gly
            20              25              30

His Arg Val Thr Leu Leu Glu Arg Gly Ala Val Leu Gly Gly Arg Ala
            35              40              45

Gly Arg Trp Ser Glu Ala Gly Phe Thr Phe Asp Thr Gly Pro Ser Trp
    50              55              60

Tyr Leu Met Pro Glu Val Ile Asp Arg Trp Phe Arg Leu Met Gly Thr
```

```
65              70              75              80

Ser Ala Ala Glu Arg Leu Asp Leu Arg Arg Leu Asp Pro Gly Tyr Arg
                85              90              95

Val Tyr Phe Glu Gly His Leu His Glu Pro Pro Val Asp Val Arg Thr
               100             105             110

Gly His Ala Glu Thr Leu Phe Glu Ser Leu Glu Pro Gly Ala Gly Arg
           115             120             125

Arg Leu Arg Ala Tyr Leu Asp Ser Ala Ser Arg Ile Tyr Gly Leu Ala
       130             135             140

Lys Glu His Phe Leu Tyr Thr Asp Phe Arg Arg Pro Ala Ala Leu Ala
145             150             155             160

His Pro Asp Val Leu Arg Ala Leu Pro Ala Leu Gly Pro Gln Leu Leu
               165             170             175

Gly Gly Leu Arg Ser His Val Ala Ala Arg Phe Gln Asp Pro Arg Leu
           180             185             190

Arg Gln Ile Leu Gly Tyr Pro Ala Val Phe Leu Gly Thr Ser Pro Asp
           195             200             205

Arg Ala Pro Ala Met Tyr His Leu Met Ser His Leu Asp Leu Ala Asp
       210             215             220

Gly Val Gln Tyr Pro Leu Gly Gly Phe Ala Ala Leu Val Asp Ala Met
225             230             235             240

Ala Glu Val Val Arg Glu Ala Gly Val Glu Ile Arg Thr Gly Val Glu
               245             250             255

Ala Thr Ala Val Glu Val Ala Asp Arg Pro Ala Pro Ala Gly Arg Leu
               260             265             270

Gly Arg Leu Ala Ala Arg Leu Pro Arg Pro Gly Ala Ala Arg Gly Asp
           275             280             285

Glu Gly Arg Arg Arg Arg Pro Gly Arg Val Thr Gly Val Ala Trp Arg
       290             295             300

Ser Asp Asp Gly Ala Ala Gly Arg Leu Asp Ala Asp Val Val Val Ala
305             310             315             320

Ala Ala Asp Leu His His Val Gln Thr Arg Leu Leu Pro Pro Gly Arg
           325             330             335

Arg Val Ala Glu Ser Thr Trp Asp Arg Arg Asp Pro Gly Pro Ser Gly
           340             345             350

Val Leu Val Cys Val Gly Val Arg Gly Ser Leu Pro Gln Leu Ala His
           355             360             365

His Thr Leu Leu Phe Thr Ala Asp Trp Glu Asp Asn Phe Gly Arg Ile
       370             375             380

Glu Arg Gly Glu Asp Leu Ala Ala Asp Thr Ser Ile Tyr Val Ser Arg
385             390             395             400

Thr Ser Ala Thr Asp Pro Gly Val Ala Pro Glu Gly Asp Glu Asn Leu
               405             410             415

Phe Ile Leu Val Pro Ala Pro Ala Glu Pro Gly Trp Gly Arg Gly Gly
           420             425             430

Ile Arg Val Arg Asp Gly Gln Gly Trp Arg Val Asp Arg Ala Gly Asp
           435             440             445

Ala Gln Val Glu Ala Val Ala Asp Arg Ala Leu Asp Gln Leu Ala Arg
       450             455             460

Trp Ala Gly Ile Pro Asp Leu Ala Glu Arg Ile Val Val Arg Arg Thr
465             470             475             480

Tyr Gly Pro Gly Asp Phe Ala Ala Asp Val His Ala Trp Arg Gly Ser
               485             490             495
```

-continued

---

```
Leu Leu Gly Pro Gly His Thr Leu Ala Gln Ser Ala Met Phe Arg Pro
            500                 505                 510

Ser Val Arg Asp Ala Asp Val Ala Gly Leu Met Tyr Ala Gly Ser Ser
            515                 520                 525

Val Arg Pro Gly Ile Gly Val Pro Met Cys Leu Ile Ser Ala Glu Val
            530                 535                 540

Val Arg Asp Glu Leu Arg His Asp Ala Arg Arg Ala Arg Pro Ala Gly
545                 550                 555                 560

Pro Gly Gly Ser Gly Thr
            565

<210> SEQ ID NO 4
<211> LENGTH: 548
<212> TYPE: PRT
<213> ORGANISM: Corynebacterium glutamicum

<400> SEQUENCE: 4

Met Lys Val Ser Thr Lys Thr Pro Arg Ser Ser Gly Thr Ala Val Val
1               5                   10                  15

Ile Gly Ala Gly Val Ala Gly Leu Ala Thr Ser Ala Leu Leu Ala Arg
            20                  25                  30

Asp Gly Trp Gln Val Thr Val Leu Glu Lys Asn Thr Asp Val Gly Gly
            35                  40                  45

Arg Ala Gly Ser Leu Glu Ile Ser Gly Phe Pro Gly Phe Arg Trp Asp
            50                  55                  60

Thr Gly Pro Ser Trp Tyr Leu Met Pro Glu Ala Phe Asp His Phe Phe
65                  70                  75                  80

Ala Leu Phe Gly Ala Cys Thr Ser Asp Tyr Leu Asp Leu Val Glu Leu
            85                  90                  95

Thr Pro Gly Tyr Arg Val Phe Ser Gly Thr His Asp Ala Val Asp Val
            100                 105                 110

Pro Thr Gly Arg Glu Glu Ala Ile Ala Leu Phe Glu Ser Ile Glu Pro
            115                 120                 125

Gly Ala Gly Ala Lys Leu Gly Asn Tyr Leu Asp Ser Ala Ala Asp Ala
            130                 135                 140

Tyr Asp Ile Ala Ile Asp Arg Phe Leu Tyr Asn Asn Phe Ser Thr Leu
145                 150                 155                 160

Gly Pro Leu Leu His Arg Asp Val Leu Thr Arg Ala Gly Arg Leu Phe
            165                 170                 175

Ser Leu Leu Thr Arg Ser Leu Gln Lys Tyr Val Asn Ser Gln Phe Ser
            180                 185                 190

Ser Pro Val Leu Arg Gln Ile Leu Thr Tyr Pro Ala Val Phe Leu Ser
            195                 200                 205

Ser Arg Pro Thr Thr Thr Pro Ser Met Tyr His Leu Met Ser His Thr
            210                 215                 220

Asp Leu Val Gln Gly Val Lys Tyr Pro Ile Gly Gly Phe Thr Ala Val
225                 230                 235                 240

Val Asn Ala Leu His Gln Leu Ala Leu Glu Asn Gly Val Glu Phe Gln
            245                 250                 255

Leu Asp Ser Glu Val Ile Ser Ile Asn Thr Ala Ser Ser Arg Gly Asn
            260                 265                 270

Thr Ser Ala Thr Gly Val Ser Leu Leu His Asn Arg Lys Val Gln Asn
            275                 280                 285

Leu Asp Ala Asp Leu Val Val Ser Ala Gly Asp Leu His His Thr Glu
```

-continued

```
            290                 295                 300
Asn Asn Leu Leu Pro Arg Glu Leu Arg Thr Tyr Pro Glu Arg Tyr Trp
305                 310                 315                 320

Ser Asn Arg Asn Pro Gly Ile Gly Ala Val Leu Ile Leu Leu Gly Val
                325                 330                 335

Lys Gly Glu Leu Pro Gln Leu Asp His His Asn Leu Phe Phe Ser Glu
                340                 345                 350

Asp Trp Thr Asp Asp Phe Ala Val Val Phe Asp Gly Pro Gln Leu Thr
            355                 360                 365

Arg Pro His Asn Ala Ser Asn Ser Ile Tyr Val Ser Lys Pro Ser Thr
            370                 375                 380

Ser Glu Asp Gly Val Ala Pro Ala Gly Tyr Glu Asn Leu Phe Val Leu
385                 390                 395                 400

Ile Pro Thr Lys Ala Ser Ser Ser Ile Gly His Gly Asp Ala Tyr Met
                405                 410                 415

Gln Ser Ala Ser Ala Ser Val Glu Thr Ile Ala Ser His Ala Ile Asn
                420                 425                 430

Gln Ile Ala Thr Gln Ala Gly Ile Pro Asp Leu Thr Asp Arg Ile Val
            435                 440                 445

Val Lys Arg Thr Ile Gly Pro Ala Asp Phe Glu His Arg Tyr His Ser
            450                 455                 460

Trp Val Gly Ser Ala Leu Gly Pro Ala His Thr Leu Arg Gln Ser Ala
465                 470                 475                 480

Phe Leu Arg Gly Arg Asn Ser Ser Arg Lys Val Asn Asn Leu Phe Tyr
                485                 490                 495

Ser Gly Ala Thr Thr Val Pro Gly Val Gly Ile Pro Met Cys Leu Ile
                500                 505                 510

Ser Ala Glu Asn Ile Ile Lys Arg Leu His Ala Asp Thr Ser Ala Gly
                515                 520                 525

Pro Leu Pro Glu Pro Leu Pro Pro Lys Thr Thr Pro Ser Gln Lys Thr
            530                 535                 540

Ser Tyr Asp His
545

<210> SEQ ID NO 5
<211> LENGTH: 518
<212> TYPE: PRT
<213> ORGANISM: Microbacterium testaceum

<400> SEQUENCE: 5

Met Ser Ala Gln Arg Ile Val Val Val Gly Gly Gly Ile Ala Gly Leu
1               5                   10                  15

Gly Thr Ala Ala Leu Leu Ala Asp Arg Gly His Asp Val His Leu Phe
                20                  25                  30

Glu Ala Arg Asp Ala Leu Gly Gly Arg Ala Gly Ser Trp Glu Lys Asp
            35                  40                  45

Gly Phe Arg Phe Asp Thr Gly Pro Ser Trp Tyr Leu Met Pro Glu Val
            50                  55                  60

Phe Asp His Phe Phe Arg Leu Leu Gly Thr Ser Ala Ala Glu Gln Leu
65                  70                  75                  80

Asp Leu Val Arg Leu Asp Pro Ala Tyr Arg Val Tyr Gly Pro Pro Gly
                85                  90                  95

Lys Gly Glu Pro Ile Asp Ile Val Ser Gly Arg Glu Ala Val Arg Ala
                100                 105                 110
```

-continued

```
Leu Phe Glu Lys His Glu Pro Gly Ser Gly Asp Asn Ile Asp Ala Tyr
        115                 120                 125

Leu Asp Ser Ala Lys Asp Ala Tyr Glu Leu Ser Thr Ser Lys Phe Leu
        130                 135                 140

Tyr Asp Pro Tyr Ser Ser Thr Lys Gly Leu Arg Asp Pro Ala Leu Val
145                 150                 155                 160

Lys Arg Leu Pro Thr Leu Ile Pro Leu Leu Thr Arg Thr Leu Trp Lys
                165                 170                 175

Arg Val Thr Ser Asp Phe Lys Asn Thr Arg Leu Gln Gln Ile Leu Ala
                180                 185                 190

Tyr Pro Ala Val Phe Leu Gly Gly Ser Pro Phe Glu Val Pro Ser Leu
                195                 200                 205

Tyr His Leu Met Ser His Leu Asp Leu Gly Asp Gly Val Leu Tyr Pro
        210                 215                 220

Lys Gly Gly Met Thr Glu Ile Ile Thr Ala Ile Glu Lys Leu Ala Arg
225                 230                 235                 240

Gly Arg Gly Val Thr Ile Glu Thr Ser Ala Pro Val Glu Ala Ile Ile
                245                 250                 255

Thr Glu Ser Gly Thr Ala Arg Gly Val Arg Leu Ala Asp Gly Arg Ile
                260                 265                 270

Phe Ala Ala Asp Ala Val Val Ser Gly Ala Asp Leu His His Thr Glu
        275                 280                 285

Asn Glu Leu Leu Glu Glu Lys Asp Arg Gln Tyr Pro Glu Lys Trp Trp
        290                 295                 300

Lys Asp Lys Val Pro Ser Pro Gly Ala Leu Leu Leu Leu Leu Gly Val
305                 310                 315                 320

Thr Gly Glu Leu Pro Gln Leu Thr His His Thr Leu Leu Phe Thr Asp
                325                 330                 335

Asp Trp His Thr Asn Phe Asp Ala Ile Phe Gly Glu Asn Lys Lys Ile
                340                 345                 350

Pro Asp Pro Ala Ser Ile Tyr Ile Cys Arg Pro Ser Ala Ser Asp Asp
                355                 360                 365

Ser Val Ala Pro Glu Gly His Glu Asn Leu Phe Val Leu Val Pro Val
        370                 375                 380

Pro Ala Asp Pro Asp Ser Gly Arg Gly Gly Val Ser Gly Ala Gly Asp
385                 390                 395                 400

Glu Arg Ile Glu Lys Ala Ala Asp Arg Val Ile Ala Gln Ile Gly Glu
                405                 410                 415

Trp Thr Gly Ile Pro Asp Leu Ala Glu Arg Ile Val Val Arg Lys Thr
                420                 425                 430

Ile Ala Pro Glu Asp Phe Lys Glu Asp Leu His Ala Trp His Gly Asn
        435                 440                 445

Ser Leu Gly Leu Ala His Thr Leu Asn Gln Ser Ala Ile Phe Arg Pro
        450                 455                 460

Lys Asn Arg Ser Arg Lys Val Asp Asn Leu Tyr Tyr Ala Gly Thr Ser
465                 470                 475                 480

Val Leu Pro Gly Ile Gly Leu Pro Met Cys Leu Ile Ser Ala Glu Leu
                485                 490                 495

Val Val Lys Arg Leu Thr Gly Asp Thr Thr Ala Gly Pro Leu Ala Glu
                500                 505                 510

Pro Ala Arg Ala Ala Val
                515
```

<210> SEQ ID NO 6
<211> LENGTH: 529
<212> TYPE: PRT
<213> ORGANISM: Leifsonia xyli

<400> SEQUENCE: 6

```
Met Thr Ala Pro Arg Ala Val Val Ile Gly Gly Gly Ile Ala Gly Leu
1               5                   10                  15

Ala Thr Ala Ala Leu Leu Ala Arg Asp Gly Arg Pro Val Thr Leu Leu
            20                  25                  30

Glu Gln His Gly Thr Leu Gly Gly Arg Ala Gly Arg Trp Glu Thr Ala
        35                  40                  45

Gly Phe Arg Phe Asp Thr Gly Pro Ser Trp Tyr Leu Met Pro Glu Val
    50                  55                  60

Phe Asp His Phe Phe Arg Leu Leu Gly Thr Ser Ala Ala Glu Gln Leu
65                  70                  75                  80

Asp Leu Val Thr Leu Asp Pro Gly Tyr Arg Val Phe Ala Glu Asp Gly
            85                  90                  95

Arg Arg Pro Leu Asp Ile Arg Ala Ala Gly Ala Ala Asn Arg Ala Leu
            100                 105                 110

Phe Glu Ser Val Glu Ser Gly Ala Gly Ala Ala Leu Asp Arg Tyr Leu
        115                 120                 125

Ala Gly Ala Arg Glu Thr Tyr Gly Leu Ala Val Asp Arg Phe Leu Tyr
    130                 135                 140

Ser Thr Phe Ala Ser Ile Arg Pro Leu Leu Ser Arg Glu Val Leu Ala
145                 150                 155                 160

Arg Thr Gly Arg Leu Ala Arg Leu Leu Leu Glu Pro Leu Asp Arg Tyr
            165                 170                 175

Ala Ala Arg Cys Val Arg Asp Thr Val Leu Arg Gln Ile Leu Gly Tyr
            180                 185                 190

Pro Ala Val Phe Leu Gly Thr Ser Pro Asp Arg Ala Pro Ser Leu Tyr
        195                 200                 205

His Leu Met Ser His Leu Asp Leu Asp Asp Gly Val Arg Tyr Pro Val
    210                 215                 220

Gly Gly Phe Ala Thr Leu Ile Asp Arg Ile Val Ala Phe Ala Arg Ala
225                 230                 235                 240

Ala Gly Ala Glu Leu Val Thr Asp Ala Arg Val Thr Gly Ile Arg Thr
            245                 250                 255

Gly Val Gly Gly Arg Arg Ala Ser Ala Phe Gly Val Asp Trp Val Asp
            260                 265                 270

Ala Glu Gly Arg Ser Arg His Lys His Ala Asp Ile Val Val Ser Ala
        275                 280                 285

Val Asp Arg Arg His Thr Glu Thr Gln Leu Leu Pro Pro Ala Leu Arg
    290                 295                 300

Ser Ser Asp Arg Glu Trp Lys Arg Arg Asp Pro Gly Pro Gly Ala Val
305                 310                 315                 320

Leu Ala Met Leu Gly Val Arg Gly Glu Leu Pro Gln Leu Thr His His
            325                 330                 335

Asn Leu Phe Phe Thr Thr Asp Trp Glu Ala Asn Phe Glu Arg Val Phe
            340                 345                 350

Gly Ala Asp Arg Gly Val Pro Asp Pro Ala Ser Leu Tyr Val Cys Lys
        355                 360                 365

Pro Ser Ala Thr Asp Pro Gly Val Ala Pro Pro Gly His Glu Asn Leu
    370                 375                 380
```

-continued

```
Phe Val Leu Val Pro Val Pro Ala Asp Thr Ser Ile Gly Ser Gly Gly
385             390             395             400

Ile Asp Gly Gly Gly Asp Arg Leu Val Glu Arg Thr Ala Asp Ala Ala
            405             410             415

Ile Ala Gln Val Ala Ala Trp Ala Gly Ile Pro Asp Leu Ala Asp Arg
        420             425             430

Val Val Val Arg Arg Thr Val Gly Pro Gly Asp Phe Ala Ala Ala Val
        435             440             445

Asn Ala Trp Ser Gly Gly Ala Leu Gly Pro Ala His Thr Leu Arg Gln
    450             455             460

Ser Ala Phe Leu Arg Pro Gly Asn Ala Ser Arg Arg Val Arg Gly Leu
465             470             475             480

Phe Phe Ala Gly Ala Thr Thr Ile Pro Gly Ile Gly Leu Pro Met Cys
            485             490             495

Leu Ile Ser Ala Glu Leu Ala Val Lys Arg Leu Arg Gly Asp Thr Ser
            500             505             510

Ala Gly Pro Leu Ala Glu Pro Leu Ala Pro Ala Arg Val Gly Pro Val
            515             520             525

Pro
```

```
<210> SEQ ID NO 7
<211> LENGTH: 304
<212> TYPE: PRT
<213> ORGANISM: Corynebacterium glutamicum

<400> SEQUENCE: 7

Met Thr His Gln Asn Ser Pro Leu Phe Leu Lys Ser Ala Leu Arg Leu
1               5               10              15

Tyr Asn Arg Ala Ser Phe Lys Ala Ser His Lys Val Ile Glu Glu Tyr
            20              25              30

Ser Thr Ser Phe Ser Leu Ser Thr Trp Leu Leu Ser Pro Arg Ile Arg
        35              40              45

Asn Asp Ile Arg Asn Leu Tyr Ala Val Val Arg Ile Ala Asp Glu Ile
    50              55              60

Val Asp Gly Thr Ala His Ala Ala Gly Cys Ser Thr Ala Lys Ile Glu
65              70              75              80

Glu Ile Leu Asp Ala Tyr Glu Ile Ala Val Leu Ala Ala Pro Gln Gln
            85              90              95

Arg Phe Asn Thr Asp Leu Val Leu Gln Ala Tyr Gly Glu Thr Ala Arg
            100             105             110

Arg Cys Asp Phe Glu Gln Glu His Val Ile Ala Phe Phe Ala Ser Met
        115             120             125

Arg Lys Asp Leu Lys Ala Asn Thr His Asp Pro Asp Ser Phe Thr Thr
    130             135             140

Tyr Val Tyr Gly Ser Ala Glu Val Ile Gly Leu Leu Cys Leu Ser Val
145             150             155             160

Phe Asn Gln Gly Arg Thr Ile Ser Lys Lys Arg Leu Glu Ile Met Gln
            165             170             175

Asn Gly Ala Arg Ser Leu Gly Ala Ala Phe Gln Lys Ile Asn Phe Leu
            180             185             190

Arg Asp Leu Ala Glu Asp Gln Gln Asn Leu Gly Arg Phe Tyr Phe Pro
        195             200             205

Lys Thr Ser Gln Gly Thr Leu Thr Lys Glu Gln Lys Glu Asp Leu Ile
    210             215             220
```

```
Ala Asp Ile Arg Gln Asp Leu Ala Ile Ala His Asp Ala Phe Pro Glu
225             230                 235                 240

Ile Pro Val Gln Ala Arg Ile Gly Val Ile Ser Ala Tyr Leu Leu Phe
            245                 250                 255

Gln Lys Leu Thr Asp Arg Ile Glu Ala Thr Pro Thr Ala Asp Leu Leu
            260                 265                 270

Arg Glu Arg Ile Arg Val Pro Leu His Ile Lys Leu Ser Thr Leu Ala
            275                 280                 285

Arg Ala Thr Met Lys Gly Leu Ser Met Ser Ile Tyr Arg Lys Asn Ser
            290                 295                 300
```

<210> SEQ ID NO 8
<211> LENGTH: 289
<212> TYPE: PRT
<213> ORGANISM: Microbacterium testaceum

<400> SEQUENCE: 8

```
Met Ser Val Gly Pro Thr Gly Leu Ala Leu Tyr Ser Arg Thr Ala Asp
1               5                   10                  15

Asp Ala Ala Ala Ala Val Ile His Arg Tyr Ser Thr Ser Phe Gly Leu
            20                  25                  30

Ala Ala Arg Leu Leu Gly Ala Arg Pro Arg Pro His Val Arg Asn Ile
            35                  40                  45

Tyr Ala Leu Val Arg Val Ala Asp Glu Ile Val Asp Gly Pro Ala His
    50                  55                  60

Asp Ala Gly Leu Thr Pro Glu Arg Glu Arg Ala Val Leu Asn Ala Leu
65                  70                  75                  80

Glu Asn Glu Val Met Asp Ala Ile Ala Thr Gly Phe Ser Ala Asn Leu
                85                  90                  95

Val Val His Ala Phe Ala Arg Thr Ala Arg Glu Cys Gly Ile Asp Ala
            100                 105                 110

Asp Leu Ile Ala Pro Phe Phe Ala Ser Met Arg Thr Asp Ile Asp Thr
            115                 120                 125

Ala Glu His Asp Asp Leu Ser His Asp Ala Tyr Val Tyr Gly Ser Ala
            130                 135                 140

Glu Val Val Gly Leu Met Cys Leu Gln Val Phe Leu Asn Ala Gly Met
145                 150                 155                 160

Ser Ala Pro Ala Arg Pro Ala Ala Asp Leu Val Asp Gly Ala Arg Arg
                165                 170                 175

Leu Gly Ala Ala Phe Gln Asp Val Asn Phe Leu Arg Asp Leu Ala Asp
            180                 185                 190

Asp Ala Asp Arg Leu Gly Arg Asp Tyr Leu Asp Gly Ala Ala Asp Asp
            195                 200                 205

Asp Arg Arg Thr Ala Val Leu Asp Arg Ile Asp Ala Asp Leu Ala Ala
            210                 215                 220

Ala Ala Ser Val Ile Pro His Leu Pro Pro Asp Cys Arg Ala Ala Val
225                 230                 235                 240

Thr Ala Ala His Asp Leu Phe Ala Glu Leu Ser Arg Arg Leu Arg Leu
                245                 250                 255

Ser Pro Ala Gly Ala Pro Arg Val Arg Val Pro Asp Gly Val Lys Ala
            260                 265                 270

Thr Leu Ala Ala Arg Ala Leu Leu Gly Arg Pro Pro Lys Gly Pro Arg
            275                 280                 285

Pro
```

```
<210> SEQ ID NO 9
<211> LENGTH: 298
<212> TYPE: PRT
<213> ORGANISM: Leifsonia xyli subsp. xyli

<400> SEQUENCE: 9

Met Thr Arg Thr Glu Thr Ala Ala Ala Ala Gly Pro Pro Thr Asp Leu
1               5                   10                  15

Ala Leu Tyr Thr Arg Ala Ala His Glu Ser Ala Ala Thr Ile Ile His
            20                  25                  30

Gln Tyr Ser Thr Ser Phe Gly Met Val Thr Arg Leu Leu Ala Pro Arg
        35                  40                  45

Val Arg Pro Arg Val Glu Asp Val Tyr Ala Leu Val Arg Ile Ala Asp
    50                  55                  60

Glu Ile Val Asp Gly Ala Ala Ala Glu Ala Gly Leu Asp Leu Ala Asp
65                  70                  75                  80

Gln Arg Ala Leu Leu Asp Ala Leu Glu Ala Asp Thr Glu Arg Ala Met
            85                  90                  95

Arg Thr Gly Tyr Ser Ala Asn Leu Val Val His Ser Phe Ala Ala Thr
            100                 105                 110

Ala Arg Asp Ser Gly Ile Gly Val Ala Leu Thr Arg Pro Phe Phe Ala
        115                 120                 125

Ser Met Arg Arg Asp Leu Ser Leu Val Asp Phe Thr Ala Asp Glu Leu
    130                 135                 140

Arg Glu Tyr Val Tyr Gly Ser Ala Glu Val Val Gly Leu Met Cys Leu
145                 150                 155                 160

Ala Val Phe Leu Thr Asp Ser Pro Val Ala Asp Asp Arg Arg Arg Arg
            165                 170                 175

Leu Glu Ala Gly Ala Arg Arg Leu Gly Ala Ala Phe Gln Lys Ile Asn
            180                 185                 190

Phe Leu Arg Asp Leu Ala Ala Asp Tyr Ala Gly Leu Gly Arg Ser Tyr
        195                 200                 205

Phe Pro Gly Ile Asp Pro Ala Arg Leu Thr Glu Arg Gln Lys Leu Ala
    210                 215                 220

Leu Val Val Asp Ile Asp Gly Asp Leu Gly Ala Ala Ala Asp Ala Ile
225                 230                 235                 240

Ala Glu Leu Pro Gly Asn Cys Arg Arg Ala Ile Val Ala Ala His Ala
            245                 250                 255

Leu Phe Ser Glu Leu Ser Asp Arg Ile Arg Ala Thr Pro Ala Arg Asp
            260                 265                 270

Leu Ile Val Arg Arg Val Ser Val Pro Met Arg Thr Lys Leu Ala Ile
        275                 280                 285

Leu Leu Arg Ala Thr Ala Gly Ile Leu Arg
    290                 295

<210> SEQ ID NO 10
<211> LENGTH: 314
<212> TYPE: PRT
<213> ORGANISM: Arthrobacter arilatensis

<400> SEQUENCE: 10

Met Thr Arg Glu Phe Ser Ser Thr Asp Thr Thr Gly Thr Ala Ala Leu
1               5                   10                  15

Glu His Tyr Ser Arg Ala Ala Ser Arg Ser Ala Arg Val Val Leu Gly
            20                  25                  30
```

```
Glu Tyr Ser Thr Ser Phe Ser Leu Ala Cys Arg Leu Leu Asp Ala Ser
        35                  40                  45

Ser Ala Gly His Ile Ala Asn Ile Tyr Ala Leu Val Arg Leu Ala Asp
    50                  55                  60

Glu Ile Val Asp Gly Val Ala Phe Gln Ala Gly Leu Asp Asp Pro Ala
65                  70                  75                  80

Ile Gly Ala Cys Leu Asp Glu Leu Glu Ala Glu Thr Leu Arg Ala Met
                85                  90                  95

Asp Arg Gly Tyr Ser Thr Asn Met Val Val His Ala Phe Ala Ile Thr
                100                 105                 110

Ala Arg Ala Thr Gly Ile Lys Ala Glu Leu Thr Thr Pro Phe Phe Ala
            115                 120                 125

Ser Met Arg Ala Asp Leu Ser Thr Gly Glu His Asp Ala Arg Ser Leu
    130                 135                 140

Gln Glu Tyr Ile Tyr Gly Ser Ala Glu Val Ile Gly Leu Met Cys Leu
145                 150                 155                 160

Gln Val Phe Ala Ala Met Pro Gly Ala Pro Gln Leu Asn Arg Ala Glu
                165                 170                 175

Glu Gln Arg Thr Lys Leu Ala Ala Arg Ser Leu Gly Ala Ala Phe Gln
            180                 185                 190

Lys Val Asn Phe Leu Arg Asp Leu Ala Gln Asp Ser Gln Glu Leu Gly
            195                 200                 205

Arg Thr Tyr Phe Pro Gly Met Asp Pro Glu Gly Phe Asp Glu Gln Gly
    210                 215                 220

Lys Ala Leu Leu Val Ala Gln Ile Asn Gln Asp Leu Ala Ala Ala Arg
225                 230                 235                 240

Ala Gly Leu Pro Tyr Leu Ala Pro Gln Ala Ala Arg Ala Val Cys Leu
                245                 250                 255

Ala His Asp Leu Phe Gln Glu Leu Asn Val Gln Leu Glu Lys Val Pro
                260                 265                 270

Ala Ala Ala Leu Leu Arg Thr Arg Ile Ser Val Ser Ala Pro Arg Lys
            275                 280                 285

Ala Met Ile Ala Leu Arg Val Leu Leu Gly Ala Gly Thr Pro Ser His
    290                 295                 300

His Lys Leu Arg Met Glu Val Ser Ser Arg
305                 310

<210> SEQ ID NO 11
<211> LENGTH: 303
<212> TYPE: PRT
<213> ORGANISM: Kocuria rhizophila

<400> SEQUENCE: 11

Met Arg Thr Pro Met Lys Leu Pro Ala Glu Arg Ala His Thr Pro Leu
1               5                   10                  15

Arg Leu Tyr Thr Gly Thr Ala Leu Ala Ser Ser Gly Val Val Ile Gly
                20                  25                  30

Glu Tyr Ser Thr Ser Phe Ser Leu Ala Cys Arg Thr Leu Pro Gly Pro
        35                  40                  45

Val Arg Arg Asp Ile Ala Gly Ile Tyr Ala Leu Val Arg Val Ala Asp
    50                  55                  60

Glu Ile Val Asp Gly Thr Ala Arg Ala Ala Gly Leu Asp Asp Arg Ala
65                  70                  75                  80

Val Arg Arg Ala Leu Asp Gly Tyr Glu Ala Ala Val Asp Arg Ala Leu
                85                  90                  95
```

```
Glu Thr Gly Phe Ser Thr Asp Leu Val Val His Gly Phe Ala Asp Val
                100                 105                 110

Ala Arg Arg His Gly Phe Gly Arg Glu Leu Thr Glu Pro Phe Phe Ala
            115                 120                 125

Ser Met Arg Ala Asp Leu Glu Val Ala Glu His Asp Gly Ala Ser Leu
        130                 135                 140

Glu Asp Tyr Ile Tyr Gly Ser Ala Glu Val Val Gly Leu Met Cys Leu
145                 150                 155                 160

Glu Val Phe Thr Asp Met Pro Gly Thr Arg Ala Gln Thr Pro Glu Gln
                165                 170                 175

Arg Glu Met Leu Arg Ser Thr Ala Arg Arg Leu Gly Ala Ala Phe Gln
            180                 185                 190

Lys Val Asn Phe Leu Arg Asp Leu Gly Ala Asp His Asp Gln Leu Gly
            195                 200                 205

Arg Thr Tyr Leu Pro Gly Ala Asp Pro Ala His Leu Thr Glu Asp Arg
        210                 215                 220

Lys Ala Ala Leu Leu Ala Asp Leu Asp Ala Asp Leu Asp Ala Ala Val
225                 230                 235                 240

Pro Gly Ile Leu Ala Leu Asp Arg Arg Ala Arg Arg Ala Val Ser Met
                245                 250                 255

Ala His Gly Leu Phe Thr Glu Leu Ala Arg Arg Ile Glu Arg Val Pro
            260                 265                 270

Ala Arg Glu Leu Ser Thr Arg Arg Val Ser Val Pro Thr Ala Val Lys
        275                 280                 285

Leu Gln Ile Ala Ala Arg Ala Ile Ala Asp Thr Glu Val Thr Ala
    290                 295                 300
```

```
<210> SEQ ID NO 12
<211> LENGTH: 298
<212> TYPE: PRT
<213> ORGANISM: Micrococcus luteus

<400> SEQUENCE: 12
```

```
Met Ala Ala Pro Thr Pro Ser Pro Ala Ala Leu Tyr Thr Arg Thr Ala
1               5                   10                  15

His Thr Ala Ala Ala Gln Val Ile Arg Arg Tyr Ser Thr Ser Phe Ser
            20                  25                  30

Trp Ala Cys Arg Thr Leu Pro Arg Gln Ala Arg Gln Asp Val Ala Thr
        35                  40                  45

Ile Tyr Ala Met Val Arg Val Ala Asp Glu Val Val Asp Gly Val Ala
    50                  55                  60

Val Ala Ala Gly Leu Asp Glu Ala Gly Val Arg Ala Ala Leu Asp Asp
65                  70                  75                  80

Tyr Glu Arg Ala Cys Glu Ala Ala Met Ala Ser Gly Phe Ala Thr Asp
                85                  90                  95

Pro Val Leu His Ala Phe Ala Asp Val Ala Arg Arg His Gly Ile Thr
            100                 105                 110

Pro Glu Leu Thr Arg Pro Phe Phe Ala Ser Met Arg Ala Asp Leu Gly
        115                 120                 125

Ile Arg Glu His Gly Ala Glu Ser Leu Asp Ala Tyr Ile His Gly Ser
    130                 135                 140

Ala Glu Val Val Gly Leu Met Cys Leu Gln Val Phe Leu Ser Leu Pro
145                 150                 155                 160

Gly Thr Arg Ala Arg Thr Pro Gly Gln Arg Gln Glu Leu Arg Ala Gln
```

-continued

```
                    165              170              175

Ala Ser Arg Leu Gly Ala Ala Phe Gln Lys Val Asn Phe Leu Arg Asp
            180              185              190

Leu Ala Ala Asp His His Glu Leu Gly Arg Thr Tyr Leu Pro Gly Ala
            195              200              205

Ala Pro Gly Val Leu Thr Glu Ala Arg Lys Ala Glu Leu Val Ala Glu
            210              215              220

Val Arg Ala Asp Leu Asp Ala Ala Leu Pro Gly Ile Arg Val Leu Asp
225              230              235              240

Pro Gly Ala Gly Arg Ala Val Ala Leu Ala His Gly Leu Phe Ala Ala
            245              250              255

Leu Val Asp Arg Ile Glu Ala Thr Pro Ala Ala Glu Leu Ala His Arg
            260              265              270

Arg Val Arg Val Pro Asp His Gln Lys Ala Arg Ile Ala Ala Arg Val
            275              280              285

Leu Ala Arg Gly Arg Arg Gly Gly Arg Arg
        290              295

<210> SEQ ID NO 13
<211> LENGTH: 287
<212> TYPE: PRT
<213> ORGANISM: Corynebacterium glutamicum

<400> SEQUENCE: 13

Met Met Glu Lys Ile Arg Leu Ile Leu Leu Ser Ser Arg Pro Ile Ser
1               5               10               15

Trp Ile Asn Thr Ala Tyr Pro Phe Gly Leu Ala Tyr Leu Leu Asn Ala
            20               25               30

Gly Glu Ile Asp Trp Leu Phe Trp Leu Gly Ile Val Phe Phe Leu Ile
            35               40               45

Pro Tyr Asn Ile Ala Met Tyr Gly Ile Asn Asp Val Phe Asp Tyr Glu
        50               55               60

Ser Asp Met Arg Asn Pro Arg Lys Gly Gly Val Glu Gly Ala Val Leu
65               70               75               80

Pro Lys Ser Ser His Ser Thr Leu Leu Trp Ala Ser Ala Ile Ser Thr
            85               90               95

Ile Pro Phe Leu Val Ile Leu Phe Ile Phe Gly Thr Trp Met Ser Ser
            100              105              110

Leu Trp Leu Thr Leu Ser Val Leu Ala Val Ile Ala Tyr Ser Ala Pro
            115              120              125

Lys Leu Arg Phe Lys Glu Arg Pro Phe Ile Asp Ala Leu Thr Ser Ser
        130              135              140

Thr His Phe Thr Ser Pro Ala Leu Ile Gly Ala Thr Ile Thr Gly Thr
145              150              155              160

Ser Pro Ser Ala Ala Met Trp Ile Ala Leu Gly Ser Phe Phe Leu Trp
            165              170              175

Gly Met Ala Ser Gln Ile Leu Gly Ala Val Gln Asp Val Asn Ala Asp
            180              185              190

Arg Glu Ala Asn Leu Ser Ser Ile Ala Thr Val Ile Gly Ala Arg Gly
        195              200              205

Ala Ile Arg Leu Ser Val Val Leu Tyr Leu Leu Ala Ala Val Leu Val
        210              215              220

Thr Thr Leu Pro Asn Pro Ala Trp Ile Ile Gly Ile Ala Ile Leu Thr
225              230              235              240
```

```
Tyr Val Phe Asn Ala Ala Arg Phe Trp Asn Ile Thr Asp Ala Ser Cys
            245                 250             255

Glu Gln Ala Asn Arg Ser Trp Lys Val Phe Leu Trp Leu Asn Tyr Phe
            260                 265             270

Val Gly Ala Val Ile Thr Ile Leu Leu Ile Ala Ile His Gln Ile
        275                 280             285
```

<210> SEQ ID NO 14
<211> LENGTH: 287
<212> TYPE: PRT
<213> ORGANISM: Arthrobacter arilaitensis

<400> SEQUENCE: 14

```
Met Ile Arg Gly Ile Val Ala Ser Ser Arg Pro Ile Ser Trp Val Asn
1               5                   10              15

Thr Ala Tyr Pro Phe Ala Ala Ala Tyr Leu Leu Ala Gly Gly Gly Val
            20                  25              30

Asp Trp Lys Phe Ile Leu Gly Thr Val Phe Phe Leu Phe Pro Tyr Asn
            35                  40              45

Leu Leu Met Tyr Gly Val Asn Asp Val Phe Asp Tyr Glu Ser Asp Met
        50                  55              60

Arg Asn Pro Arg Lys Gly Gly Ile Glu Gly Ala Val Leu Ser Lys Gln
65                  70                  75                  80

Ser His Lys Ala Leu Leu Ile Ala Cys Thr Val Cys Ser Leu Pro Phe
                85                  90                  95

Leu Ile Val Leu Ala Ala Gly Gly Asp Ala Ala Ser Asn Ile Thr Leu
            100                 105             110

Ala Val Ser Ile Phe Ala Val Leu Ala Tyr Ser Ala Pro Arg Leu Arg
        115                 120             125

Phe Lys Glu Arg Pro Gly Leu Asp Ser Leu Thr Ser Ala Val His Phe
        130                 135             140

Val Ser Pro Ala Val Tyr Gly Trp Val Leu Ala Gly Ser Ala Val Gln
145                 150                 155             160

Ala Glu Gln Trp Met Val Phe Leu Ala Phe Leu Leu Trp Gly Met Ala
            165                 170             175

Ser His Ala Leu Gly Ala Ile Gln Asp Ile Ile Pro Asp Arg Gln Gly
            180                 185             190

Gly Leu Gly Ser Ile Ala Thr Val Leu Ser Ala Arg Lys Thr Ile Tyr
        195                 200             205

Leu Val Leu Ala Cys Tyr Leu Leu Ala Gly Gly Leu Val Ala Val Gly
        210                 215             220

Val Ser Gly Ile Gly Arg Trp Ala Ala Val Leu Ser Leu Pro Tyr Val
225                 230                 235             240

Leu Asn Val Leu Pro His Leu Gly Ile Ser Asp Ala Ser Ser Gly Thr
            245                 250             255

Val Asn Arg Gly Trp Lys Arg Phe Leu Trp Ile Asn Tyr Leu Cys Gly
            260                 265             270

Phe Leu Leu Thr Met Leu Leu Ile Phe Ser Ala Phe Phe Thr Tyr
        275                 280             285
```

<210> SEQ ID NO 15
<211> LENGTH: 298
<212> TYPE: PRT
<213> ORGANISM: Kocuria rhizophila

<400> SEQUENCE: 15

```
Met Pro Arg Arg Glu Val Asp Val Leu Thr Arg Leu Phe Trp Ala Ser
1               5                   10                  15

Arg Pro Leu Ser Trp Val Asn Thr Ala Tyr Pro Phe Thr Ala Ala Val
            20                  25                  30

Leu Leu Thr Gly Gly Leu Pro Trp Trp Leu Val Val Leu Gly Thr Val
            35                  40                  45

Phe Phe Leu Val Pro Tyr Asn Leu Ala Met Tyr Gly Ile Asn Asp Val
    50                  55                  60

Phe Asp Tyr Glu Ser Asp Leu Arg Asn Pro Arg Lys Gly Gly Val Glu
65                  70                  75                  80

Gly Ala Val Val Asp Arg Ala Ala Gln Arg Pro Val Leu Leu Ala Ser
                85                  90                  95

Cys Leu Val Pro Ala Pro Phe Val Leu Val Leu Gly Gly Tyr Ala Val
            100                 105                 110

Val Thr Gly Asn Trp Val Ser Ile Ala Val Leu Ala Val Ser Leu Phe
            115                 120                 125

Ala Val Val Ala Tyr Ser Trp Ala Gly Leu Arg Phe Lys Glu Arg Pro
        130                 135                 140

Phe Val Asp Ala Met Thr Ser Ala Thr His Phe Val Ser Pro Ala Val
145                 150                 155                 160

Tyr Gly Leu Thr Leu Ala Gly Ala Thr Phe Thr Pro Gly Leu Trp Ala
            165                 170                 175

Leu Leu Ile Gly Phe Phe Leu Trp Gly Met Ala Ser Gln Met Phe Gly
            180                 185                 190

Ala Val Gln Asp Val Val Pro Asp Arg Glu Gly Gly Leu Ala Ser Val
        195                 200                 205

Ala Thr Val Leu Gly Ala Arg Pro Thr Val Trp Val Ala Ala Leu Leu
    210                 215                 220

Tyr Ala Leu Ala Gly Gly Leu Met Val Phe Thr Glu Trp Pro Gly Gln
225                 230                 235                 240

Leu Ala Ala Leu Leu Ala Val Pro Tyr Leu Leu Asn Val Leu Arg Phe
            245                 250                 255

Ser Gly Val Thr Asp Thr Asp Ser Gly Arg Ala Asn Ala Gly Trp Lys
            260                 265                 270

Thr Phe Leu Trp Leu Asn Tyr Leu Thr Gly Phe Leu Val Thr Met Leu
            275                 280                 285

Leu Ile Trp Trp Ala Ala Met Arg Pro Val
    290                 295
```

```
<210> SEQ ID NO 16
<211> LENGTH: 294
<212> TYPE: PRT
<213> ORGANISM: Micrococcus luteus

<400> SEQUENCE: 16
```

```
Met Ile Arg Thr Leu Phe Trp Val Ser Arg Pro Val Ser Trp Val Asn
1               5                   10                  15

Thr Ala Tyr Pro Phe Ala Ala Ala Ala Ile Leu Thr Gly Gly Leu Pro
            20                  25                  30

Ala Trp Leu Val Val Leu Gly Val Val Phe Phe Leu Val Pro Tyr Asn
            35                  40                  45

Leu Ala Met Tyr Gly Ile Asn Asp Val Phe Asp Phe Ala Ser Asp Leu
    50                  55                  60

Arg Asn Pro Arg Lys Gly Gly Val Glu Gly Ser Val Leu Gly Asp Pro
65                  70                  75                  80
```

-continued

```
Ala Val Arg Arg Arg Val Leu Ala Trp Ser Val Leu Leu Pro Val Pro
            85                  90                  95

Phe Val Ala Val Leu Ala Gly Trp Ser Ala Val Arg Gly Glu Trp Ala
            100                 105                 110

Ala Val Leu Val Leu Ala Val Ser Leu Phe Ala Val Val Ala Tyr Ser
            115                 120                 125

Trp Ala Gly Leu Arg Phe Lys Glu Arg Pro Phe Leu Asp Ala Ala Thr
        130                 135                 140

Ser Ala Thr His Phe Val Ser Pro Ala Val Tyr Gly Leu Ala Leu Ala
145                 150                 155                 160

Gly Ala Thr Pro Thr Pro Ala Leu Ala Ala Leu Leu Gly Ala Phe Phe
                165                 170                 175

Leu Trp Gly Met Ala Ser Gln Met Phe Gly Ala Val Gln Asp Val Val
            180                 185                 190

Pro Asp Arg Glu Gly Gly Leu Ala Ser Val Ala Thr Val Leu Gly Ala
            195                 200                 205

Arg Arg Thr Val Leu Leu Ala Ala Gly Leu Tyr Ala Ala Ala Gly Leu
        210                 215                 220

Leu Leu Leu Ala Thr Asp Pro Pro Gly Pro Leu Ala Ala Leu Leu Ala
225                 230                 235                 240

Val Pro Tyr Val Val Asn Thr Leu Arg Phe Arg Arg Ile Thr Asp Ala
                245                 250                 255

Thr Ser Gly Ala Ala His Arg Gly Trp Gln Leu Phe Leu Pro Leu Asn
            260                 265                 270

Tyr Val Thr Gly Phe Leu Val Thr Leu Leu Leu Ile Gly Trp Ala Leu
            275                 280                 285

Thr Arg Gly Ala Ala Ala
        290
```

```
<210> SEQ ID NO 17
<211> LENGTH: 297
<212> TYPE: PRT
<213> ORGANISM: Microbacterium testaceum

<400> SEQUENCE: 17

Met Thr Ala Pro Ala Ala Leu Thr Pro Gly Arg Val Leu Arg Glu Leu
1               5                   10                  15

Phe Val Ser Ser Arg Pro Val Ser Trp Ile Asn Thr Ala Phe Pro Phe
            20                  25                  30

Ala Ala Ala Tyr Leu Leu Thr Thr Arg Gln Ile Asp Ala Thr Leu Ile
            35                  40                  45

Val Gly Ile Leu Phe Phe Leu Val Pro Tyr Asn Leu Ala Met Tyr Gly
        50                  55                  60

Val Asn Asp Val Phe Asp Tyr Glu Ser Asp Leu Arg Asn Pro Arg Lys
65                  70                  75                  80

Gly Gly Thr His Gly Ala Val Leu Asp Lys Arg Met His Pro Ile Thr
                85                  90                  95

Leu Trp Ala Ser Val Leu Ser Cys Leu Pro Phe Val Val Tyr Leu Val
            100                 105                 110

Val Val Gly Ser Pro Leu Ser Trp Leu Val Leu Ala Leu Ser Leu Phe
            115                 120                 125

Phe Val Val Phe Tyr Ser Ala Pro Pro Leu Arg Leu Lys Glu Arg Pro
        130                 135                 140

Phe Ala Asp Ser Val Thr Ser Ser Ile His Phe Phe Ser Pro Ala Val
```

-continued

```
145              150               155                 160

Tyr Gly Leu Val Leu Ala Gly Ala Val Trp Thr Trp Gln Leu Val Phe
                165               170               175

Val Phe Val Ala Phe Ala Leu Trp Gly Ile Ala Ser His Ala Phe Gly
                180               185               190

Ala Val Gln Asp Val Glu Ala Asp Arg Ala Ala Asp Ile Ser Ser Ile
                195               200               205

Ala Thr Ala Arg Gly Ala Arg Trp Thr Val Arg Phe Ala Leu Val Ala
        210               215               220

Tyr Ala Leu Ala Gly Val Ala Met Leu Phe Thr Ala Trp Pro Gly Pro
225               230               235               240

Leu Ala Gly Val Leu Val Ile Pro Tyr Leu Val Val Cys Trp Pro Tyr
                245               250               255

Arg Asn Val Thr Asp Ala Glu Ser Asp Arg Ala Thr Ala Gly Trp Asn
                260               265               270

Arg Phe Leu Trp Leu Asn Gln Ile Ala Gly Phe Gly Thr Thr Met Leu
                275               280               285

Leu Ile Trp Trp Trp Leu Leu Thr Ala
        290               295

<210> SEQ ID NO 18
<211> LENGTH: 298
<212> TYPE: PRT
<213> ORGANISM: Clavibacter michiganensis

<400> SEQUENCE: 18

Met Ser Asp Val Arg Ala Arg Pro Gly Ala Ala Glu Met Leu Arg Thr
1               5                 10                15

Val Ala Leu Ser Ser Arg Pro Leu Ser Trp Val Asn Thr Ala Phe Pro
                20                25                30

Phe Ala Ala Ala Tyr Leu Thr Val Thr Arg Glu Leu Asp Leu Thr Ala
        35                40                45

Val Leu Gly Thr Leu Tyr Phe Leu Ile Pro Tyr Asn Leu Ala Met Tyr
        50                55                60

Gly Ile Asn Asp Val Phe Asp Tyr Glu Ser Asp Met Arg Asn Pro Arg
65                70                75                80

Lys Gly Gly Val Glu Gly Ala Val Leu Ala Arg Ala Met His Arg Pro
                85                90                95

Val Leu Leu Ala Val Leu Val Thr Asn Val Pro Phe Leu Val Tyr Leu
                100               105               110

Val Ile Val Gly Ser Ala Ala Ser Ile Ala Val Leu Ala Val Ser Val
        115               120               125

Phe Ala Val Ile Ala Tyr Ser Leu Lys Gly Leu Arg Phe Lys Glu Arg
        130               135               140

Pro Val Leu Asp Ser Leu Thr Ser Ser Thr His Phe Thr Ser Pro Ala
145               150               155               160

Val Tyr Gly Ile Val Leu Ala Gly Gly Ala Phe Thr Pro Ala Leu Trp
                165               170               175

Ala Ile Leu Ala Ala Phe Phe Leu Trp Gly Val Ala Ser His Ala Phe
                180               185               190

Gly Ala Val Gln Asp Ile Val Ala Asp Arg Glu Gly Gly Ile Ser Ser
                195               200               205

Ile Ala Thr Val Leu Gly Gly Ala Val Thr Val Arg Ile Ala Val Leu
        210               215               220
```

-continued

```
Ala Tyr Ala Ala Ala Gly Val Ala Met Leu Phe Thr Gly Leu Pro Gly
225                 230                 235                 240

Ile Ile Ala Ala Val Leu Val Ile Pro Tyr Ile Leu Ser Thr Ala Pro
                245                 250                 255

Phe Trp Ser Ile Arg Asp Glu Asp Ala Gly Ala Ala Asn Arg Gly Trp
                260                 265                 270

Arg Arg Phe Leu Gly Leu Asn Phe Leu Ser Gly Phe Val Val Thr Met
                275                 280                 285

Leu Leu Ile Ala Tyr Trp Leu Thr Thr Ala
    290                 295

<210> SEQ ID NO 19
<211> LENGTH: 291
<212> TYPE: PRT
<213> ORGANISM: Leifsonia xyli

<400> SEQUENCE: 19

Met Ile Val Thr Ala Pro Pro Leu Phe Arg Gln Leu Phe Leu Ala Ser
1               5                   10                  15

Arg Pro Leu Ser Trp Ile Asn Thr Ala Tyr Pro Phe Ala Ala Ala Tyr
                20                  25                  30

Leu Leu Thr Ala Arg Glu Ala Asp Ile Val Phe Ile Val Gly Thr Leu
                35                  40                  45

Phe Phe Leu Val Pro Tyr Asn Leu Thr Met Tyr Gly Val Asn Asp Val
    50                  55                  60

Phe Asp Tyr Ala Ser Asp Leu Arg Asn Pro Arg Lys Gly Gly Val Glu
65                  70                  75                  80

Gly Ala Leu Leu Asp Pro Gly Thr His Arg Arg Thr Leu Val Ala Ala
                85                  90                  95

Ala Ala Thr Ser Leu Pro Phe Leu Val Phe Leu Ala Leu Ala Gly Pro
                100                 105                 110

Pro Leu Ser Trp Ala Val Leu Ala Gly Ser Leu Phe Phe Val Leu Ala
                115                 120                 125

Tyr Ser Val Arg Gly Leu Arg Phe Lys Lys Val Pro Phe Leu Asp Ser
    130                 135                 140

Ala Thr Ser Ser Ile His Phe Val Ser Pro Ala Leu Tyr Gly Leu Val
145                 150                 155                 160

Leu Ala Gly Ala Thr Phe Thr Pro Gly Leu Trp Leu Val Leu Phe Ala
                165                 170                 175

Phe Phe Leu Trp Gly Val Gly Ser His Ala Phe Gly Ala Val Gln Asp
                180                 185                 190

Val Ala Pro Asp Arg Glu Ala Gly Ile Ala Ser Val Ala Thr Val Leu
                195                 200                 205

Gly Ala Ala Arg Thr Val Arg Phe Ala Ile Ala Ala Trp Ala Leu Ala
    210                 215                 220

Ala Leu Ala Ala Leu Ala Ile Pro Trp Pro Gly Pro Leu Val Ala Met
225                 230                 235                 240

Leu Ala Leu Pro Tyr Ile Thr Val Ala Ala Pro Phe Trp Ser Val Pro
                245                 250                 255

Asp Asp Arg Ala Ser Ala Ala Asn Arg Gly Trp Leu Arg Phe Leu Gly
                260                 265                 270

Ile Asn Tyr Ala Cys Gly Cys Leu Leu Thr Leu Leu Leu Ile Gly Tyr
                275                 280                 285

Ala Leu Arg
    290
```

```
<210> SEQ ID NO 20
<211> LENGTH: 340
<212> TYPE: PRT
<213> ORGANISM: Caenorhabditis elegans

<400> SEQUENCE: 20

Met Tyr Arg Phe Leu Ser Gly Ile Lys Val Val Glu Ile Ala Gly Leu
1               5                   10                  15

Ala Pro Val Pro His Cys Gly Met Met Leu Ala Asp Phe Gly Ala Asp
            20                  25                  30

Val Thr Val Ile Asp Lys Lys Asn Pro Ala Ile Glu Gln Arg Leu Asn
        35                  40                  45

Arg Gly Lys Thr Met Lys Gln Leu Asp Leu Lys Asn Pro Glu Asp Ile
    50                  55                  60

Lys Lys Val Arg Asp Leu Cys Gln Thr Ser Asp Val Leu Leu Asp Pro
65                  70                  75                  80

Tyr Arg Pro Gly Thr Leu Glu Lys Met Gly Leu Asp Pro Ser Thr Leu
                85                  90                  95

Trp Asn Asn Asn Lys Gly Leu Ile Ile Cys Lys Ile Ser Gly Tyr Gly
            100                 105                 110

Gln Thr Gly Arg Met Ser Gln Glu Thr Gly His Asp Ile Asn Tyr Val
        115                 120                 125

Ala Leu Ser Gly Met Leu Pro Thr Phe Ser Gly Val Asn Ala Thr Arg
        130                 135                 140

Pro Trp Pro Pro Ala Asn Met Leu Ala Asp Phe Ala Gly Gly Gly Leu
145                 150                 155                 160

Ser Ala Ala Phe Gly Ile Leu Ser Ala Ile Tyr Ala Arg Ser His Asn
                165                 170                 175

Gly Gly Lys Gly Cys Leu Leu Asp Cys Ser Met Thr Glu Gly Val Ala
            180                 185                 190

Tyr Leu Ser Ser Phe Val Gln His Tyr Tyr Asp Gln Pro Asn Leu Phe
            195                 200                 205

Thr Asp Lys Tyr Ala Leu Phe Ser Gly Glu Cys Pro Ile Tyr Arg Thr
        210                 215                 220

Tyr Lys Thr Lys Asp Asp Lys Phe Val Ala Val Gly Ala Val Glu Pro
225                 230                 235                 240

Lys Phe Tyr Gln Asn Leu Phe Lys Leu Leu Asn Val Asp Gly Arg Asp
                245                 250                 255

Leu Phe Val Asn Pro Gly Lys Ile Thr Glu Asp Leu Glu Ser Arg Phe
            260                 265                 270

Leu Gln Lys Thr Arg Asp Lys Trp Ala Asn Ile Phe Lys Gly Gln Glu
            275                 280                 285

Cys Cys Val Thr Pro Val Leu Asp Ile His Glu Val Gly Ser Tyr Gly
        290                 295                 300

Gln His Val Asp Arg Asn Ser Phe Thr Lys Thr Ser Ser Asn Trp Ile
305                 310                 315                 320

Ala Asn Pro Ser Pro Arg Val Trp Thr Gln Asp Glu Leu Ala Ala Leu
                325                 330                 335

Ser Ser Lys Lys
            340

<210> SEQ ID NO 21
<211> LENGTH: 343
<212> TYPE: PRT
```

-continued

<213> ORGANISM: Caenorhabditis elegans

<400> SEQUENCE: 21

```
Met Ser Arg Leu Leu Ser Gly Ile Lys Val Val Glu Leu Gly Gly Leu
1               5                   10                  15

Ala Pro Val Pro Phe Cys Gly Met Ile Leu Ala Asp Phe Gly Ala Asp
                20                  25                  30

Val Thr Val Ile Asp Lys Lys Asn Pro Thr Val Glu Gln Arg Met Asn
            35                  40                  45

Arg Gly Lys Ser Met Lys Glu Phe Asp Leu Arg Lys Ser Glu Asp Ile
        50                  55                  60

Lys Lys Val Arg Asp Leu Cys Arg Thr Ser Asp Val Leu Leu Asp Pro
65                  70                  75                  80

Tyr Arg Pro Gly Thr Leu Glu Lys Met Gly Leu Asp Pro Leu Ser Leu
                85                  90                  95

Trp Asn Asp Asn Lys Gly Leu Ile Ile Cys Arg Ile Ser Gly Tyr Gly
                100                 105                 110

Gln Thr Gly Arg Met Ser Gln Glu Ala Gly His Asp Ile Asn Tyr Val
            115                 120                 125

Ala Met Ser Gly Met Leu Pro Thr Phe Ala Gly Ala Glu Ala Ser Arg
            130                 135                 140

Pro Trp Pro Pro Val Asn Met Leu Ala Asp Phe Ala Gly Gly Gly Leu
145                 150                 155                 160

Ser Ala Ala Phe Gly Ile Val Ser Ala Ile His Ala Arg Thr His Asn
                165                 170                 175

Gly Gly Gln Gly Cys Val Leu Asp Cys Ser Met Thr Glu Gly Val Ala
            180                 185                 190

Tyr Leu Ala Ser Phe Val Gln Tyr Tyr Tyr Glu Gln Ser His Leu Phe
            195                 200                 205

Thr Asp Lys Tyr Ala Ala Phe Thr Gly Glu Cys Pro Ile Tyr Arg Thr
        210                 215                 220

Tyr Lys Thr Lys Asp Gly Lys Phe Met Ala Val Gly Pro Leu Glu Pro
225                 230                 235                 240

Lys Phe His Gln Lys Met Phe Gln Val Leu Gly Val Asn Gly Asp Asp
                245                 250                 255

Leu Phe Ser Glu Pro Glu Arg Ile Thr Lys Val Leu Glu Glu Thr Phe
                260                 265                 270

Leu Gln Lys Thr Arg Asp Glu Trp Ser Ser Ile Phe Glu Gly Gln Asp
            275                 280                 285

Cys Cys Val Thr Pro Val Leu Asp Ile His Glu Val Gly Thr Tyr Gly
            290                 295                 300

Gln His Val Asp Arg Gln Asn Phe Thr Lys Asn Asp Lys Phe Gly Ser
305                 310                 315                 320

Thr Trp Ile Ala Lys Pro Ser Pro Arg Val Lys Thr Pro Glu Glu Leu
                325                 330                 335

Phe Ala Ala Arg Ser Lys Leu
                340
```